(12) United States Patent
Ogle

(10) Patent No.: US 11,617,865 B2
(45) Date of Patent: Apr. 4, 2023

(54) SUCTION CATHETER SYSTEMS WITH DESIGNS ALLOWING RAPID CLEARING OF CLOTS

(71) Applicant: MIVI Neuroscience, Inc., Eden Prairie, MN (US)

(72) Inventor: Matthew F. Ogle, Edina, MN (US)

(73) Assignee: MIVI Neuroscience, Inc., Eden Prairie, MN (US)

(*) Notice: Subject to any disclaimer, the term of this patent is extended or adjusted under 35 U.S.C. 154(b) by 403 days.

(21) Appl. No.: 16/751,484

(22) Filed: Jan. 24, 2020

(65) Prior Publication Data

US 2021/0228844 A1    Jul. 29, 2021

(51) Int. Cl.
*A61M 25/09* (2006.01)
*A61M 25/01* (2006.01)
(Continued)

(52) U.S. Cl.
CPC .......... *A61M 25/09* (2013.01); *A61M 1/0023* (2013.01); *A61M 25/0075* (2013.01);
(Continued)

(58) Field of Classification Search
CPC .............. A61M 16/0833; A61M 25/09; A61M 25/09041; A61M 25/01; A61B 17/221;
(Continued)

(56) References Cited

U.S. PATENT DOCUMENTS 2,730,101 A    1/1956 Hoffman
3,949,757 A    4/1976 Sabel
(Continued)

FOREIGN PATENT DOCUMENTS

CN    204158457 U    2/2015
CN    104758029 A    7/2015
(Continued)

OTHER PUBLICATIONS

Endovascular Today, "First Stroke Patients Treated With Insera's Clear Cyclical Aspiration System", www.evtoday.com/news/first-stroke-patients-treated-with-inseras-clear-cyclical-aspiration-system, (Oct. 7, 2019).
Feldman, "Transcatheter Aspiration of a Thrombus in an Aortocoronary Saphenous Vein Graft," American Journal of Cardiology, 60(4):379-380 (1987).
(Continued)

*Primary Examiner* — Scott J Medway
(74) *Attorney, Agent, or Firm* — Christensen Fonder Dardi; Andrew H. Auderieth; Peter S. Dardi

(57) ABSTRACT

A suction catheter system is described with a suction extension interfaced with a guide catheter to form a continuous suction lumen extending through a portion of the guide catheter and through the suction extension. The suction extension can be positioned by tracking the suction nozzle through a vessel while moving a proximal portion of the suction extension within the lumen of the guide catheter. The suction extension can comprise a connecting section with a non-circular cross section for interfacing with the inner lumen of an engagement section of the guide catheter. Proximal fittings attached to the guide catheter can facilitate safe removal of the catheter system from the patient by allowing for the removal of some or all of a tubular extension of the suction extension from the guide catheter behind a hemostatic seal. The fittings can include a docking manifold that can dock the connection suction of the suction extension to allow removal of the suction extension from hemostatic isolation and clearing of clots from the suction extension without further fittings such that the cleared suction extension can be efficiently reinserted for additional use.

23 Claims, 19 Drawing Sheets

(51) Int. Cl.
*A61M 25/00* (2006.01)
*A61M 1/00* (2006.01)
*A61M 39/06* (2006.01)

(52) U.S. Cl.
CPC ........ *A61M 25/0122* (2013.01); *A61M 39/06* (2013.01); *A61M 2025/091* (2013.01); *A61M 2039/062* (2013.01)

(58) Field of Classification Search
CPC .............. A61B 17/22; A61B 2217/005; A61B 2017/22079; A61B 2017/22038; A61B 2017/22084; A61B 17/12109
See application file for complete search history.

(56) References Cited

U.S. PATENT DOCUMENTS

| | | |
|---|---|---|
| 3,996,938 A | 12/1976 | Clark, III |
| 4,020,829 A | 5/1977 | Willson et al. |
| 4,033,331 A | 7/1977 | Guss et al. |
| 4,174,715 A | 11/1979 | Hasson |
| 4,610,662 A | 9/1986 | Weikl et al. |
| 4,619,263 A | 10/1986 | Frisbie et al. |
| 4,676,249 A | 6/1987 | Arenas et al. |
| 4,723,549 A | 2/1988 | Wholey et al. |
| 4,728,319 A | 3/1988 | Masch |
| 4,739,768 A | 4/1988 | Engelson |
| 4,784,636 A | 11/1988 | Rydell |
| 4,794,928 A | 1/1989 | Kletschka |
| 4,795,434 A | 1/1989 | Kujawski |
| 4,798,012 A | 1/1989 | Pasquier |
| 4,799,496 A | 1/1989 | Hargreaves et al. |
| 4,834,709 A | 5/1989 | Banning et al. |
| 4,863,431 A | 9/1989 | Vaillancourt |
| 4,873,978 A | 10/1989 | Ginsburg |
| 4,873,979 A | 10/1989 | Ginsburg |
| 4,883,460 A | 11/1989 | Zanetti |
| 4,887,613 A | 12/1989 | Farr et al. |
| 4,900,303 A | 2/1990 | Lemelson |
| 4,921,484 A | 5/1990 | Hillstead |
| 4,994,067 A | 2/1991 | Summers |
| 4,998,919 A | 3/1991 | Schnepp-Pesch et al. |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,108,419 A | 4/1992 | Reger et al. |
| 5,152,277 A | 10/1992 | Honda et al. |
| 5,161,534 A | 11/1992 | Berthaume |
| 5,163,906 A | 11/1992 | Ahmadi |
| 5,185,004 A | 2/1993 | Lashinski |
| 5,188,621 A | 2/1993 | Samson |
| 5,200,248 A | 4/1993 | Thompson et al. |
| 5,211,651 A | 5/1993 | Reger et al. |
| 5,219,332 A | 6/1993 | Nelson et al. |
| 5,308,318 A | 5/1994 | Plassche, Jr. |
| 5,312,338 A | 5/1994 | Nelson et al. |
| 5,325,868 A | 7/1994 | Kimmelstiel |
| 5,334,160 A | 8/1994 | Ellis |
| 5,352,197 A | 10/1994 | Hammersmark et al. |
| 5,364,358 A | 11/1994 | Hweitt et al. |
| 5,392,778 A | 2/1995 | Horzewski |
| 5,395,383 A | 3/1995 | Adams et al. |
| 5,413,575 A | 5/1995 | Haenggi |
| 5,423,331 A | 6/1995 | Wysham |
| 5,438,993 A | 8/1995 | Lynch et al. |
| 5,465,716 A | 11/1995 | Avitall |
| 5,485,667 A | 1/1996 | Kleshinski |
| 5,490,859 A | 2/1996 | Mische et al. |
| 5,501,694 A | 3/1996 | Resseman et al. |
| 5,527,292 A | 6/1996 | Adams et al. |
| 5,533,967 A | 7/1996 | Imran |
| 5,546,958 A | 8/1996 | Thorud et al. |
| 5,549,626 A | 8/1996 | Miller et al. |
| 5,571,122 A | 11/1996 | Kelly et al. |
| 5,578,009 A | 11/1996 | Kraus et al. |
| 5,599,307 A | 2/1997 | Bacher et al. |
| 5,720,764 A | 2/1998 | Naderlinger |
| 5,766,191 A | 6/1998 | Trerotola |
| 5,776,142 A | 7/1998 | Gunderson |
| 5,810,874 A | 9/1998 | Lefebvre |
| 5,814,064 A | 9/1998 | Daniel et al. |
| 5,817,101 A | 10/1998 | Fiedler |
| 5,836,868 A | 11/1998 | Resseman et al. |
| 5,838,645 A | 11/1998 | Hirokane et al. |
| 5,843,002 A | 12/1998 | Pecor et al. |
| 5,843,051 A | 12/1998 | Adams et al. |
| 5,851,189 A | 12/1998 | Forber |
| 5,882,329 A | 3/1999 | Patterson et al. |
| 5,897,567 A | 4/1999 | Resseman et al. |
| 5,899,890 A | 5/1999 | Chiang et al. |
| 5,910,154 A | 6/1999 | Tsugita et al. |
| 5,911,725 A | 6/1999 | Boury |
| 5,911,734 A | 6/1999 | Tsugita et al. |
| 5,928,260 A | 7/1999 | Chin et al. |
| 5,935,139 A | 8/1999 | Bates |
| 5,941,869 A | 8/1999 | Patterson et al. |
| 5,972,019 A | 10/1999 | Engelson et al. |
| 5,997,557 A | 12/1999 | Barbut et al. |
| 6,010,522 A | 1/2000 | Barbut et al. |
| 6,022,336 A | 2/2000 | Zando-Azizi et al. |
| 6,030,349 A | 2/2000 | Wilson et al. |
| 6,030,369 A | 2/2000 | Engelson et al. |
| 6,066,149 A | 5/2000 | Samson et al. |
| 6,106,530 A | 8/2000 | Harada |
| 6,117,141 A | 9/2000 | Ouchi |
| 6,155,991 A | 10/2000 | Muni et al. |
| 6,142,987 A | 11/2000 | Tsugita |
| 6,146,396 A | 11/2000 | Konya et al. |
| 6,156,005 A | 12/2000 | Théron |
| 6,159,195 A | 12/2000 | Ha et al. |
| 6,159,230 A | 12/2000 | Samuels |
| 6,168,579 B1 | 1/2001 | Tsugita |
| 6,203,561 B1 | 3/2001 | Ramee et al. |
| 6,206,868 B1 | 3/2001 | Parodi |
| 6,221,049 B1 | 4/2001 | Selmon et al. |
| 6,238,402 B1 | 5/2001 | Sullivan, III et al. |
| 6,238,412 B1 | 5/2001 | Dubrul et al. |
| 6,240,231 B1 | 5/2001 | Ferra et al. |
| 6,258,115 B1 | 7/2001 | Dubrul |
| 6,270,477 B1 | 8/2001 | Bagaoisan et al. |
| 6,277,139 B1 | 8/2001 | Levinson et al. |
| 6,306,163 B1 | 10/2001 | Fitz |
| 6,346,116 B1 | 2/2002 | Brooks et al. |
| 6,361,545 B1 | 3/2002 | Macoviak et al. |
| 6,364,894 B1 | 4/2002 | Healy et al. |
| 6,368,338 B1 | 4/2002 | Konya et al. |
| 6,391,044 B1 | 5/2002 | Yadav et al. |
| 6,454,741 B1 | 9/2002 | Muni et al. |
| 6,454,775 B1 | 9/2002 | Demarais et al. |
| 6,485,466 B2 | 11/2002 | Hamilton |
| 6,485,500 B1 | 11/2002 | Kokish et al. |
| 6,485,501 B1 | 11/2002 | Green |
| 6,511,470 B1 | 1/2003 | Hamilton |
| 6,511,471 B2 | 1/2003 | Rosenman et al. |
| 6,514,261 B1 | 2/2003 | Randall et al. |
| 6,514,273 B1 | 2/2003 | Voss et al. |
| 6,537,295 B2 | 3/2003 | Petersen |
| 6,540,768 B1 | 4/2003 | Diaz et al. |
| 6,551,302 B1 | 4/2003 | Rosinko et al. |
| 6,558,405 B1 | 5/2003 | McInnes |
| 6,569,148 B2 | 5/2003 | Bagaoisan et al. |
| 6,579,484 B1 | 6/2003 | Tiernan et al. |
| 6,589,262 B1 | 7/2003 | Honebrink et al. |
| 6,596,011 B2 | 7/2003 | Johnson et al. |
| 6,610,077 B1 | 8/2003 | Hancock et al. |
| 6,616,681 B2 | 9/2003 | Hanson et al. |
| 6,620,148 B1 | 9/2003 | Tsugita |
| 6,695,858 B1 | 2/2004 | Dubrul et al. |
| 6,695,865 B2 | 2/2004 | Boyle et al. |
| 6,702,834 B1 | 3/2004 | Boylan et al. |
| 6,773,448 B2 | 8/2004 | Kusleika et al. |
| 6,805,684 B2 | 10/2004 | Bonnette et al. |

(56) References Cited

U.S. PATENT DOCUMENTS

| | | |
|---|---|---|
| 6,805,692 B2 | 10/2004 | Muni et al. |
| 6,824,553 B1 | 11/2004 | Samson et al. |
| 6,866,669 B2 | 3/2005 | Buzzard et al. |
| 6,878,151 B2 | 4/2005 | Carrison et al. |
| 6,879,854 B2 | 4/2005 | Windheuser et al. |
| 6,911,036 B2 | 6/2005 | Douk et al. |
| 6,945,956 B2 | 9/2005 | Waldheuser et al. |
| 6,949,104 B2 | 9/2005 | Griffs et al. |
| 6,951,570 B2 | 10/2005 | Linder et al. |
| 6,958,059 B2 | 10/2005 | Zando-Azizi |
| 6,969,395 B2 | 11/2005 | Eskuri |
| 6,991,642 B2 | 1/2006 | Petersen |
| 7,052,500 B2 | 5/2006 | Bashiri et al. |
| 7,056,328 B2 | 6/2006 | Arnott |
| 7,115,134 B2 | 10/2006 | Chambers |
| 7,115,138 B2 | 10/2006 | Renati et al. |
| 7,166,120 B2 | 1/2007 | Kusleika |
| 7,220,271 B2 | 5/2007 | Clubb et al. |
| 7,229,431 B2 | 6/2007 | Houser et al. |
| 7,229,463 B2 | 6/2007 | Sutton et al. |
| 7,229,464 B2 | 6/2007 | Hanson et al. |
| 7,232,452 B2 | 6/2007 | Adams et al. |
| 7,285,126 B2 | 10/2007 | Sepetka et al. |
| 7,309,334 B2 | 12/2007 | von Hoffmann |
| 7,329,278 B2 | 2/2008 | Seguin et al. |
| 7,374,564 B2 | 5/2008 | Brown |
| 7,449,010 B1 | 11/2008 | Hayase et al. |
| 7,476,232 B2 | 1/2009 | Deal |
| 7,549,974 B2 | 6/2009 | Nayak |
| 7,625,207 B2 | 12/2009 | Hershey et al. |
| 7,736,355 B2 | 6/2010 | Itou et al. |
| 7,842,055 B2 | 11/2010 | Pintor et al. |
| 7,879,062 B2 | 2/2011 | Galdonik et al. |
| 7,938,820 B2 | 5/2011 | Webster et al. |
| 8,021,351 B2 | 9/2011 | Boldenow et al. |
| 8,048,032 B2 | 11/2011 | Root et al. |
| 8,092,483 B2 | 1/2012 | Galdonik et al. |
| 8,231,600 B2 | 7/2012 | von Hoffmann |
| 8,308,712 B2 | 11/2012 | Provost et al. |
| 8,419,786 B2 | 4/2013 | Cottone, Jr. et al. |
| 8,465,456 B2 | 6/2013 | Stivland |
| 8,764,813 B2 | 6/2014 | Jantzen et al. |
| 8,795,305 B2 | 8/2014 | Martin et al. |
| 8,814,892 B2 | 8/2014 | Galdonik et al. |
| 8,932,286 B2 | 1/2015 | Terry et al. |
| 9,199,057 B2 | 12/2015 | Nielsen |
| 9,433,427 B2 | 9/2016 | Look et al. |
| 9,532,792 B2 | 1/2017 | Galdonik et al. |
| 9,662,129 B2 | 5/2017 | Galdonik et al. |
| 9,993,613 B2 | 6/2018 | Wang et al. |
| 10,213,582 B2 | 2/2019 | Garrison et al. |
| 10,251,739 B2 | 4/2019 | Janardhan et al. |
| 10,390,926 B2 | 8/2019 | Janardhan et al. |
| 10,463,386 B2 | 11/2019 | Ogle |
| 10,478,535 B2 | 11/2019 | Ogle |
| 10,518,066 B2 | 12/2019 | Pokorney et al. |
| 10,722,253 B2 | 7/2020 | Deville et al. |
| 2001/0031980 A1 | 10/2001 | Wensel et al. |
| 2001/0044600 A1 | 11/2001 | Elkins |
| 2001/0044632 A1 | 11/2001 | Daniel et al. |
| 2001/0051811 A1 | 12/2001 | Bonnette et al. |
| 2002/0035347 A1 | 3/2002 | Bagaoisan et al. |
| 2002/0055747 A1 | 5/2002 | Cano et al. |
| 2002/0062133 A1 | 5/2002 | Gilson et al. |
| 2002/0095174 A1 | 7/2002 | Tsugita et al. |
| 2002/0111648 A1 | 8/2002 | Kusleika et al. |
| 2002/0123765 A1 | 9/2002 | Sepetka et al. |
| 2002/0133111 A1 | 9/2002 | Shadduck |
| 2002/0143362 A1 | 10/2002 | Mackoviak et al. |
| 2002/0151927 A1 | 10/2002 | Douk et al. |
| 2002/0165574 A1 | 11/2002 | Ressemann et al. |
| 2002/0169472 A1 | 11/2002 | Douk et al. |
| 2002/0183782 A1 | 12/2002 | Tsugita et al. |
| 2003/0023263 A1 | 1/2003 | Krolik et al. |
| 2003/0065353 A1 | 4/2003 | Horzewski et al. |
| 2003/0120208 A1 | 6/2003 | Houser et al. |
| 2003/0135232 A1 | 7/2003 | Douk et al. |
| 2003/0191492 A1 | 10/2003 | Gellman et al. |
| 2004/0006344 A1 | 1/2004 | Nguyen et al. |
| 2004/0006365 A1 | 1/2004 | Brady et al. |
| 2004/0015151 A1 | 1/2004 | Chambers |
| 2004/0153118 A1 | 8/2004 | Clubb et al. |
| 2004/0220611 A1 | 11/2004 | Ogle |
| 2004/0254602 A1 | 12/2004 | Lehe et al. |
| 2005/0004553 A1 | 1/2005 | Douk et al. |
| 2005/0021075 A1 | 1/2005 | Bonnette et al. |
| 2005/0021152 A1 | 1/2005 | Ogle et al. |
| 2005/0075661 A1 | 4/2005 | Levine et al. |
| 2005/0085847 A1 | 4/2005 | Galdonik et al. |
| 2005/0107738 A1 | 5/2005 | Slater et al. |
| 2005/0154344 A1 | 7/2005 | Chang |
| 2005/0209631 A1 | 9/2005 | Galdonik et al. |
| 2005/0228479 A1 | 10/2005 | Pavcnik et al. |
| 2005/0245894 A1 | 11/2005 | Zando-Azizi |
| 2005/0277976 A1 | 12/2005 | Galdonik et al. |
| 2006/0030876 A1 | 2/2006 | Peacock, III et al. |
| 2006/0047301 A1 | 3/2006 | Ogle |
| 2006/0129091 A1 | 6/2006 | Bonnette et al. |
| 2006/0195137 A1 | 8/2006 | Sepetka et al. |
| 2006/0200047 A1 | 9/2006 | Galdonik et al. |
| 2006/0200191 A1 | 9/2006 | Zando-Azizi |
| 2007/0005002 A1 | 1/2007 | Millman et al. |
| 2007/0060908 A1 | 3/2007 | Webster et al. |
| 2007/0060911 A1 | 3/2007 | Webster et al. |
| 2007/0060944 A1 | 3/2007 | Boldennow et al. |
| 2007/0135733 A1 | 6/2007 | Soukup et al. |
| 2007/0135832 A1 | 6/2007 | Wholey |
| 2007/0185501 A1 | 8/2007 | Martin et al. |
| 2007/0197956 A1 | 8/2007 | Le et al. |
| 2007/0227543 A1 | 10/2007 | Peichel |
| 2007/0250040 A1 | 10/2007 | Provost et al. |
| 2007/0250096 A1 | 10/2007 | Yamane et al. |
| 2007/0260115 A1 | 11/2007 | Brock et al. |
| 2007/0287956 A1 | 12/2007 | Tal |
| 2008/0086110 A1 | 4/2008 | Galdonik et al. |
| 2008/0109088 A1 | 5/2008 | Galdonik et al. |
| 2008/0172066 A9 | 7/2008 | Galdonik et al. |
| 2009/0076319 A1 | 3/2009 | Muyari |
| 2009/0131970 A1 | 5/2009 | Chanduszko et al. |
| 2010/0021105 A1 | 8/2010 | Luther |
| 2010/0204672 A1 | 8/2010 | Lockhart et al. |
| 2010/0280451 A1 | 11/2010 | Teeslink et al. |
| 2011/0093000 A1 | 4/2011 | Ogle et al. |
| 2011/0172678 A1 | 7/2011 | Behl et al. |
| 2012/0123466 A1 | 5/2012 | Porter et al. |
| 2012/0253313 A1 | 10/2012 | Galdonik et al. |
| 2013/0184742 A1 | 7/2013 | Ganesan et al. |
| 2013/0225937 A1 | 8/2013 | Schaffer et al. |
| 2013/0317409 A1 | 11/2013 | Cully et al. |
| 2014/0018773 A1 | 1/2014 | Wang et al. |
| 2014/0114335 A1 | 4/2014 | Banko |
| 2014/0117397 A1 | 5/2014 | Saeki et al. |
| 2014/0155980 A1 | 6/2014 | Turjman et al. |
| 2014/0249508 A1 | 9/2014 | Wang et al. |
| 2014/0276537 A1 | 9/2014 | Kruse |
| 2015/0018937 A1 | 1/2015 | Lagodzki et al. |
| 2015/0173782 A1 | 6/2015 | Garrison et al. |
| 2015/0209066 A1 | 6/2015 | Dahm et al. |
| 2015/0216650 A1 | 8/2015 | Shaltis |
| 2015/0282821 A1 | 10/2015 | Look et al. |
| 2015/0327919 A1 | 11/2015 | Clopp et al. |
| 2016/0066931 A1 | 3/2016 | Kugler et al. |
| 2016/0143616 A1* | 5/2016 | Okubo ............... A61M 39/10 600/467 |
| 2016/0166754 A1 | 6/2016 | Kassab et al. |
| 2016/0199620 A1 | 7/2016 | Pokorney et al. |
| 2016/0220741 A1 | 8/2016 | Garrison et al. |
| 2016/0270806 A1 | 9/2016 | Wallace |
| 2017/0056032 A1 | 3/2017 | Look et al. |
| 2017/0056061 A1 | 3/2017 | Ogle et al. |
| 2017/0143938 A1 | 5/2017 | Ogle et al. |
| 2017/0181760 A1 | 6/2017 | Look et al. |
| 2017/0203036 A1 | 7/2017 | Mazlish et al. |
| 2017/0231647 A1 | 8/2017 | Saunders et al. |

(56) References Cited

U.S. PATENT DOCUMENTS

| | | | |
|---|---|---|---|
| 2017/0239447 A1 | 8/2017 | Yang et al. | |
| 2017/0252051 A1 | 9/2017 | Wan et al. | |
| 2017/0252057 A1 | 9/2017 | Bonnette et al. | |
| 2017/0290600 A1 | 10/2017 | Ulm, III | |
| 2017/0303942 A1 | 10/2017 | Greenhalgh et al. | |
| 2017/0303948 A1 | 10/2017 | Wallace et al. | |
| 2017/0333060 A1 | 11/2017 | Panian | |
| 2017/0333237 A1 | 11/2017 | Walzman | |
| 2017/0354427 A1 | 12/2017 | Bonnette et al. | |
| 2018/0008295 A1 | 1/2018 | Ulm, III | |
| 2018/0064453 A1 | 3/2018 | Garrison et al. | |
| 2018/0161541 A1 | 6/2018 | Haldis et al. | |
| 2018/0339130 A1 | 11/2018 | Ogle | |
| 2019/0117891 A1 | 4/2019 | Carothers et al. | |
| 2019/0183517 A1* | 6/2019 | Ogle | A61M 1/71 |

FOREIGN PATENT DOCUMENTS

| | | |
|---|---|---|
| EP | 0117940 A2 | 9/1984 |
| EP | 1226795 A2 | 7/2002 |
| GB | 2020557 A | 11/1979 |
| WO | 95-05209 A1 | 2/1995 |
| WO | 98-38930 A1 | 9/1998 |
| WO | 00-16705 A1 | 3/2000 |
| WO | 02-055146 A1 | 7/2002 |
| WO | 02-085092 A2 | 10/2002 |
| WO | 2010-014777 A1 | 2/2010 |
| WO | 2017-091554 A1 | 6/2017 |

OTHER PUBLICATIONS

Good et al., "Hydrodynamics in Acute Ischemic Stroke Catheters Under Static and Cyclic Aspiration Conditions," Cardiovascular Engineering and Technology, vol. 11 (6), Dec. 2020, 689-698.

Penumbra, Inc., "Penumbra, Inc. Completes Pivotal Stroke Trial of Intracranial Revascularization" Press Release (2007).

Penumbra, Inc., "The Penumbra Pivotal Stroke Trial: Safety and Effectiveness of a New Generation of Mechanical Devices for Clot Removal in Intracranial Large Vessel Occlusive Disease," Stroke, 40:2761-2768 (2009).

Penumbra, Inc., "The Penumbra System®: Continuous Aspiration Thrombectomy (CAT)," Marketing Brochure © 2010 (6 pages).

Penumbra, Inc., "5Max™: Direct Aspiration™ Enables Choice," Marketing brochure © 2013 (6 pages).

Reeder et al., "Aspiration Thrombectomy for Removal of Coronary Thrombosis," American Journal of Cardiology, 70:107-110 (Jul. 1, 1992) (Abstract only).

Simon et al., "Exploring the efficacy of cyclic vs static aspiration in a cerebral thrombectomy model: an initial proof of concept study", Trauma Surgery & Acute Careopen, vol. 6 No. 9, (2013).

Webb et al., "Retrieval and Analysis of Particulate Debris After Saphenous Vein Graft Intervention," Journal of the American College of Cardiology, 34(2);468-475 (1999).

Yoo et al., "The Penumbra Stroke System: a technical review," Journal of NeuroInterventional Surgery, 4:199-205 (2012).

Abstracts from the 2007 International Stroke Conference, Stroke, 38(2):453-607 (2007).

\* cited by examiner

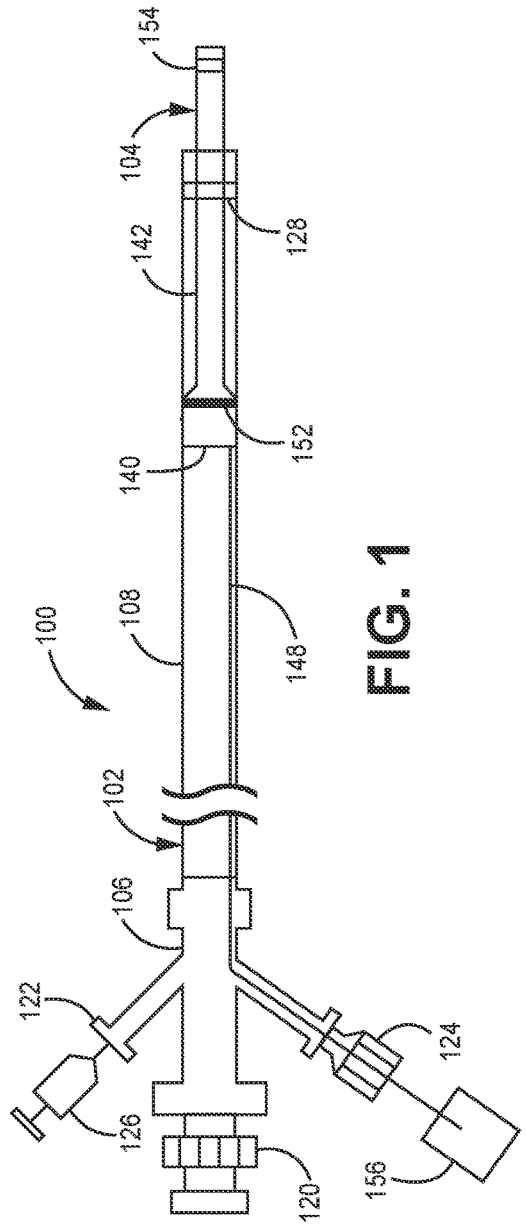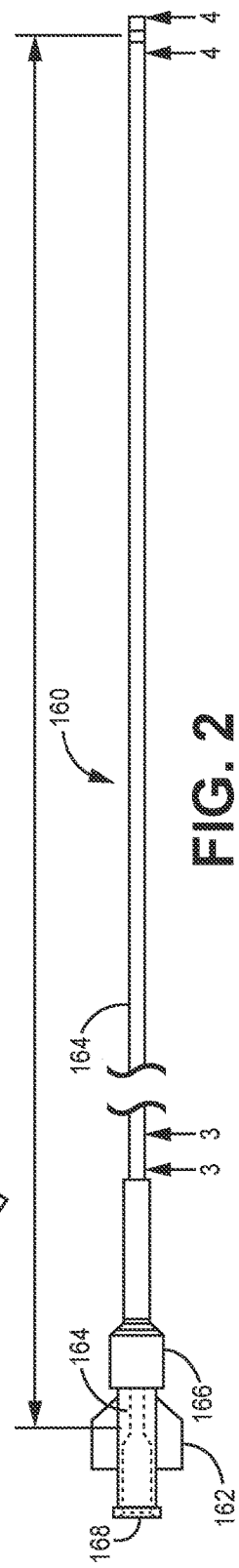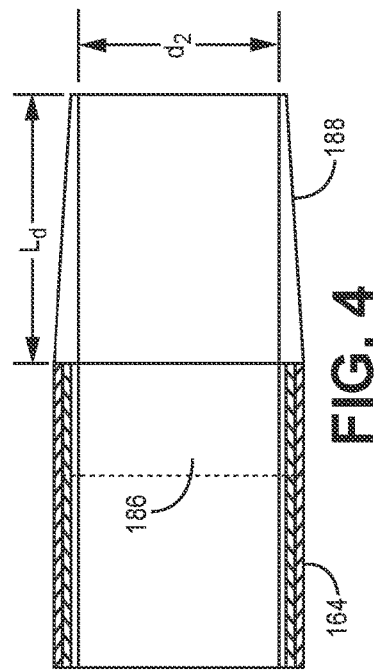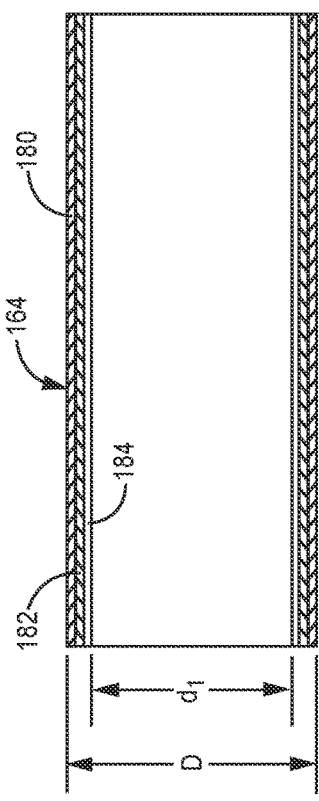

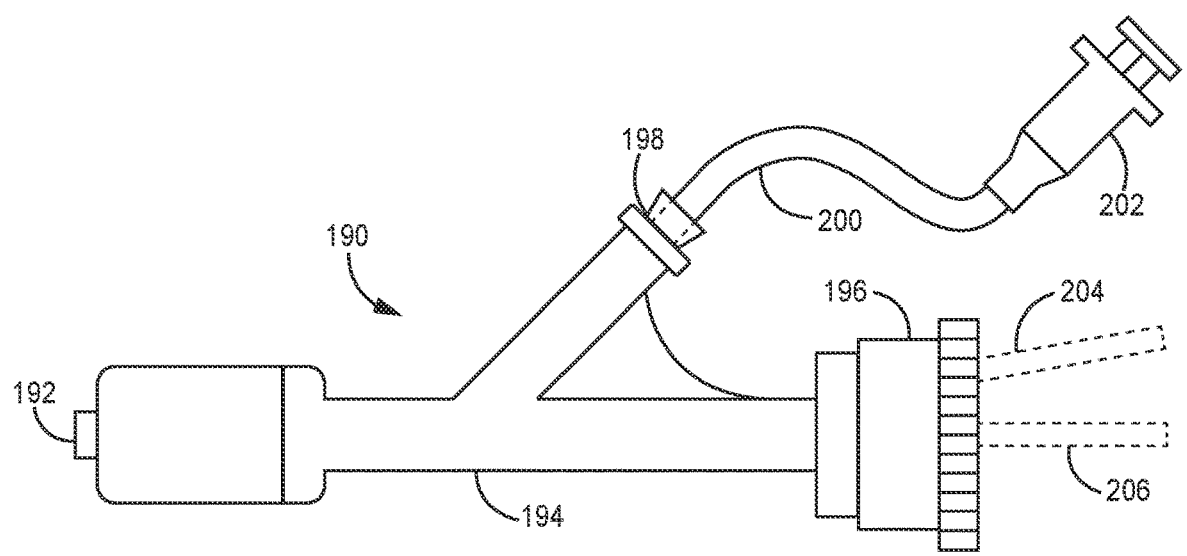
FIG. 5
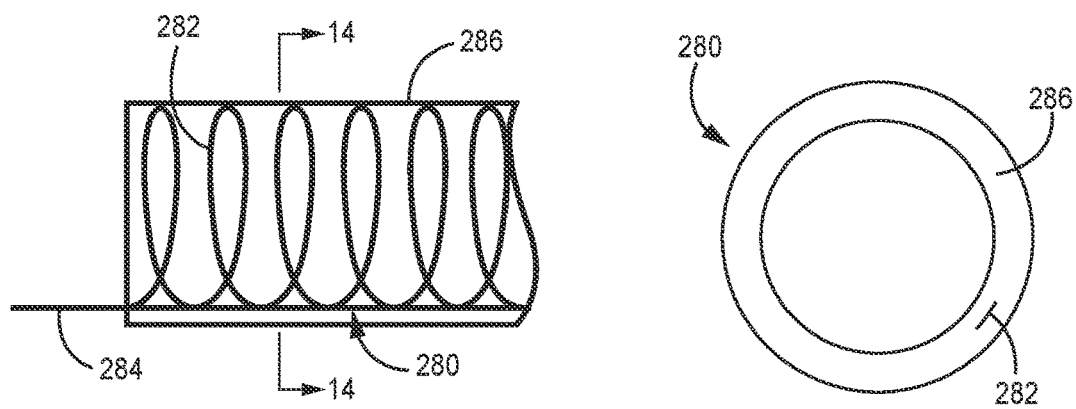
FIG. 13
FIG. 14
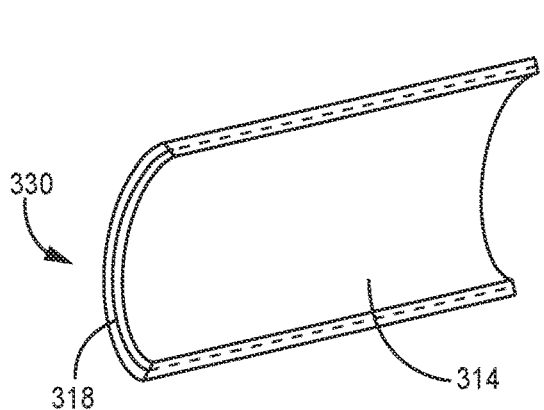
FIG. 17
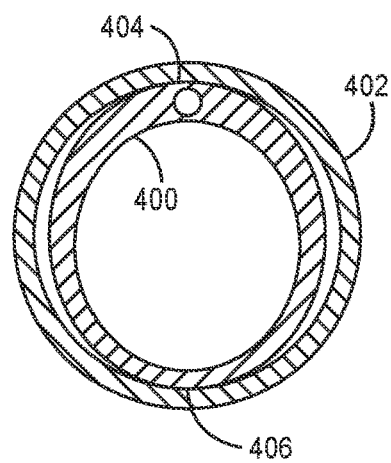
FIG. 21

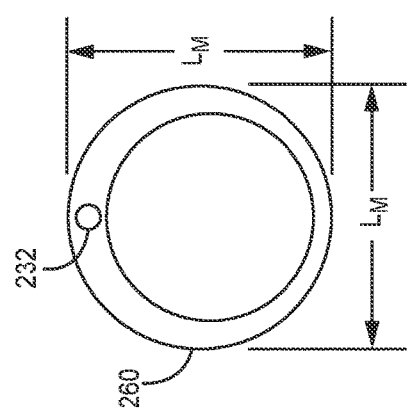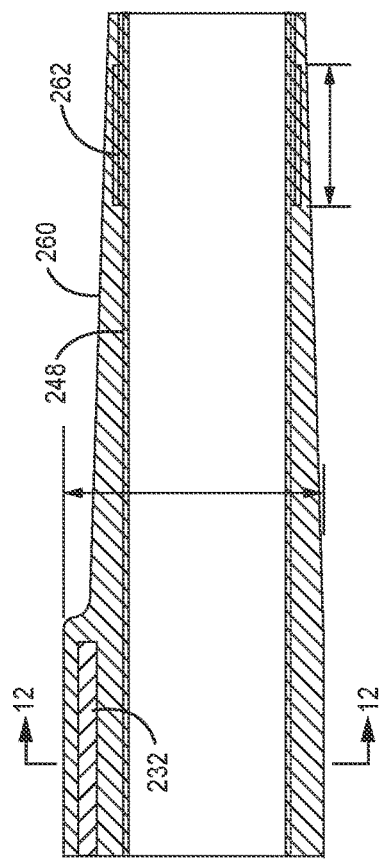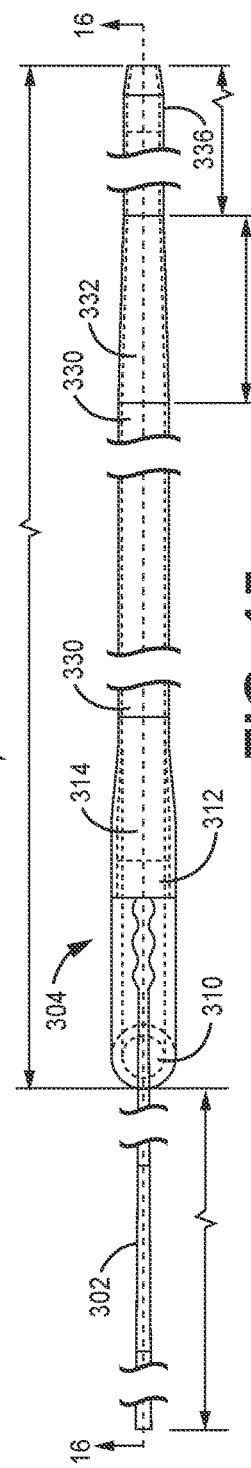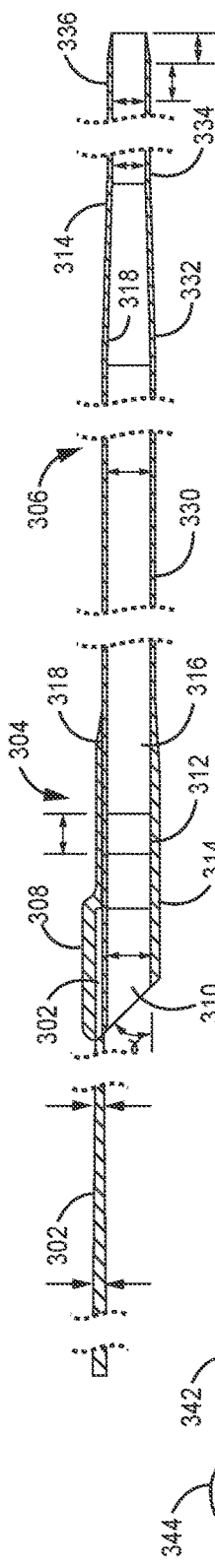

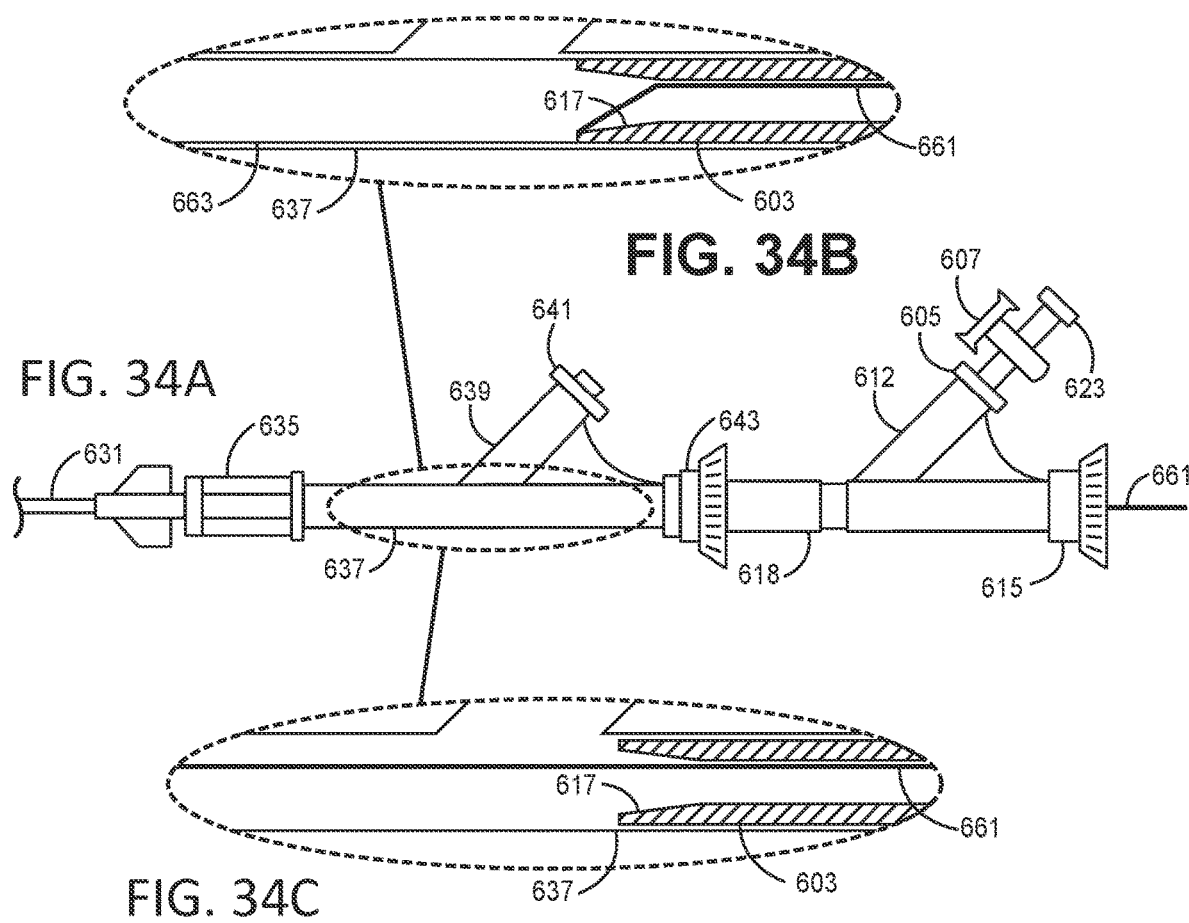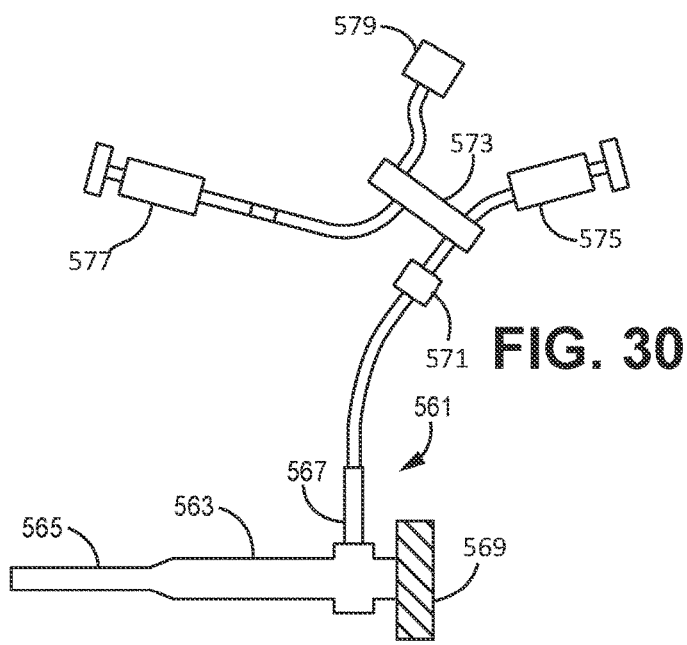

SUCTION CATHETER SYSTEMS WITH DESIGNS ALLOWING RAPID CLEARING OF CLOTS

FIELD OF THE INVENTION

The invention relates to aspiration catheter systems designed with fittings designed for efficient and safe operation of the aspiration treatment for use in bodily vessels with tortuous paths, such as cerebral arteries. In particular, the invention relates to suction catheter systems comprising a guide catheter and a suction extension slidably disposed within the guide catheter and to fittings allowing for efficient evaluation of the processing and reuse of the suction extension.

BACKGROUND OF THE INVENTION

Procedures in blood vessels of the brain are gaining use as an approach for ameliorating acute stroke events or other interventions in blood vessels in the brain. Blood vessels in the brain follow particularly tortuous paths which can increase the difficulty of reaching target locations in these vessels. Other vessels in a patient can also follow winding paths that increase the difficulty of reaching target locations.

Aspiration catheters have found use with respect to removal of clots from vessels. Furthermore, a significant reason for ischemic injury during percutaneous procedures can be generation of emboli that block smaller distal vessels. Aspiration catheters used alone or with embolic protection device can be effective to capture emboli generated during procedures. The delivery of effective devices to the small blood vessels of the brain to remove clots and/or to capture emboli remains challenging.

Ischemic strokes can be caused by clots within a cerebral artery. The clots block blood flow, and the blocked blood flow can deprive brain tissue of its blood supply. The clots can be thrombus that forms locally or an embolus that migrated from another location to the place of vessel obstruction. To reduce the effects of the cut off in blood supply to the tissue, time is an important factor. In particular, it is desirable to restore blood flow in as short of a period of time as possible. The cerebral artery system is a highly branched system of blood vessels connected to the interior carotid arteries. The cerebral arteries are also very circuitous. Medical treatment devices should be able to navigate along the circuitous route posed by the cerebral arteries for placement into the cerebral arteries.

SUMMARY OF THE INVENTION

In a first aspect, the invention pertains to a suction catheter system comprising a guide catheter, a suction extension catheter, proximal fittings, and a second branched manifold. The guide catheter generally comprises a tubular shaft with a central lumen having a proximal end and a distal opening. The suction extension catheter generally comprises a connecting section with a central lumen, a tubular extension comprising a tube that is connected with the connecting section and extends from the connecting section in a distal direction to form a continuous lumen through the central lumen of the connecting section through the tube of the tubular extension, and a control structure comprising an elongated structure extending from the connecting section in a proximal direction. The connecting section of the suction extension generally is configured to slide within at least a portion of the central lumen of the guide catheter to change the relative position of the connecting section within the central lumen and provide for at least a portion of tubular extension to extend outward from the distal opening of the tubular shaft at appropriate configurations of the connecting section. The proximal fittings can be connected to the proximal end of the guide catheter, and the proximal fittings can comprise a first fitting element with a tubular body having a distal connector connected to the proximal end of the guide catheter and a first hemostatic valve wherein the suction extension is configured to pass through the first hemostatic valve. A docking branched manifold can comprise an input tubular segment connected with at least one Y-branch having a valve and terminating with a connector, and a second branch having a hemostatic valve. The input tubular segment generally comprises a docking structure to engage the proximal end of the connection section of the suction extension at a position distal to the Y-branch to form a continuous fluid channel from the central lumen into the docking branched manifold. At least a portion of the input tubular segment may be configured for insertion through and securing within the first hemostatic valve.

In a further aspect, the invention pertains to a method for using a suction catheter system for removal of thrombus from the vasculature of a patient. For performance of the method, the suction catheter system can comprise a guide catheter having a lumen, a suction extension catheter having a tubular portion with a distal opening and a control structure, proximal fittings connected at the proximal end of the guide catheter with a first fitting element having a first hemostatic valve configured to provide access into the lumen of the first fitting element, and a docking branched manifold comprising a distal portion that can insert partially through the first hemostatic valve with a hemostatic seal, a first branch with a second hemostatic valve, and a second branch connected to a flush fluid source. In some embodiments, with the proximal end of the suction extension catheter within the lumen of the guide catheter, a suction lumen extends from the negative pressure device to a distal opening of a tubular section of the suction catheter extension, and the proximal end of the tubular section of the suction catheter extension can dock in the distal portion of the second manifold to form a fluid channel form the second branch through the suction extension catheter. The method can comprise aspirating fluid from the vasculature of a patient into the distal opening of the suction extension catheter, withdrawing the tubular portion of the suction extension catheter using the control structure to dock the proximal end of the tubular portion in the distal section of the docking branched manifold, removing the docking branched manifold and the suction extension catheter from the proximal fitting through the first hemostatic valve, and flushing the suction extension catheter to remove debris from the suction extension catheter.

In another aspect, the invention pertains to a suction catheter system comprising a guide catheter, a suction extension catheter, and proximal fittings. The guide catheter generally comprises a tubular shaft with a central lumen having a proximal end and a distal opening. The suction extension catheter generally comprises a connecting section with a central lumen, a tubular extension comprising a tube that is connected with the connecting section and extends from the connecting section in a distal direction to form a continuous lumen through the central lumen of the connecting section through the tube of the tubular extension, and a control structure comprising an elongated structure extending from the connecting section in a proximal direction and a knob at or near the proximal end of elongated structure configured to manipulate the control structure. The connecting section generally is configured to slide within at least a portion of the central lumen of the guide catheter to change the relative position of the connecting section within the central lumen and provide for at least a portion of the tubular extension to extend outward from the distal opening of the tubular shaft at appropriate configurations of the connecting section. The proximal fittings can be connected to the proximal end of the guide catheter, and the proximal fittings generally comprise a first fitting element. In some embodiments, the handle has a diameter that is larger than the connecting section so the tubular extension, the connecting section and the control structure distal to the handle can pass through a valve that does not allow passage of the handle and a length between a distal opening of the suction extension catheter and the handle defines a distance preventing the connecting section from exiting a distal opening of the guide catheter. In some embodiments, the first fitting element provides a length between the first hemostatic valve and the proximal end of the tubular shaft of the guide catheter that is at least as long as the length of the tubular extension of the suction extension

BRIEF DESCRIPTION OF THE DRAWINGS

FIG. 1 is a side view of a suction catheter system comprising a guide catheter with a suction extension with the guide catheter shown as transparent to allow visualization of structure within the guide catheter.

FIG. 2 is a side view of an embodiment of a guide catheter extending from a luer fitting to a distal tip.

FIG. 3 is a fragmentary sectional view of a portion of the guide catheter of FIG. 2 between points 3-3 in FIG. 2 with the cross section taken along a plane through the central axis of the catheter.

FIG. 4 is a fragmentary sectional view of a portion of the guide catheter of FIG. 2 between points 4-4 in FIG. 2 with the cross section taken along a plane through the central axis of the catheter.

FIG. 5 is a side view of a branched hemostatic valve fitting suitable for connection with the luer fitting of the guide catheter of FIG. 2.

FIG. 11 is a fragmentary sectional view of the catheter of FIG. 11 taken along an orthogonal view indicated by line 11-11 of FIG. 9.

FIG. 12 is a sectional end view of the catheter of FIG. 6 taken along line 12-12 of FIG. 8.

FIG. 13 is a fragmentary side view of an alternative embodiment of a suction extension with the expanded insert showing the attachment of a control wire to the proximal portion using a coiled end portion of the control wire.

FIG. 14 is a sectional view taken along line 14-14 of FIG. 13.

FIG. 15 is a top view of an alternative embodiment of a suction extension in which a tubular extension has two tubular sections with different diameters connected by a taper section.

FIG. 16 is a sectional view of the alternative embodiment of the suction extension shown in FIG. 15, in which the section is taken along line 16-16 of FIG. 15.

FIG. 16A is an alternative embodiment of the proximal end of the control structure in which a handle is attached to the control structure and the end of the control structure is twisted to restrict the movement of the handle relative to its position on the control structure.

FIG. 17 is a cut-away portion of a catheter wall showing some features of its construction.

FIG. 21 is a sectional end view of a connecting section of a suction extension interfacing with engagement section of a guide catheter with a non-circular cross section.

FIG. 30 is a side view of a first embodiment of a docking branched manifold with a branching fluid delivery channel.

FIG. 34A is a side view of the fitting components connected to the guide catheter as shown in FIG. 31A with a loaded suction extension in which the control structure of the suction extension is shown exiting the proximal end of the fittings.

FIG. 34B is a fragmentary sectional view of a portion of the first fitting element and the docking branched manifold of FIG. 34A where the section is taken through a central axis of the lumen, in which the suction extension is in a docked position engaging the docking branched manifold.

FIG. 34C is a fragmentary sectional view of a portion of the first fitting element and the docking branched manifolds of FIG. 34A as shown in FIG. 34B except that the suction extension is in an un-docked position.

DETAILED DESCRIPTION OF THE INVENTION

Figure 6:
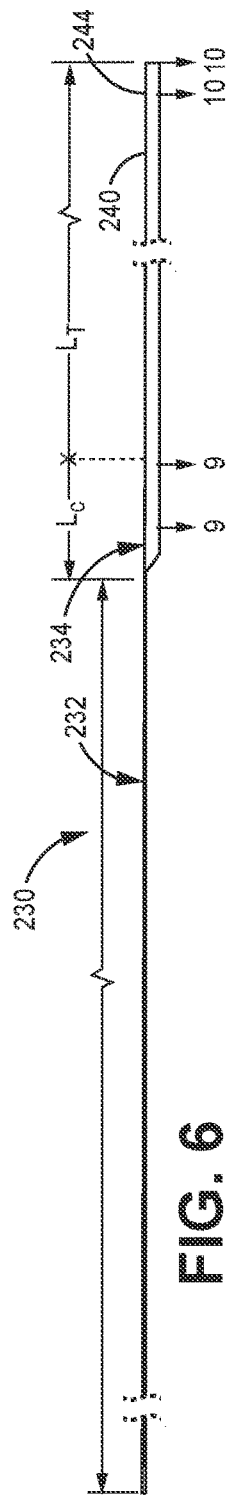
FIG. 6 is a side view of an embodiment of a section extension.

A suction catheter system can include a guide catheter adapted with a suction extension having a narrower distal tube that can provide suction with a high flow rate. This two piece system provides an advantage of strong suction ability, while also providing some flexibility with respect to efficient performance of the procedure while leaving the guide catheter in position. Fitting designs are described that provide for removal of the suction extension for quick clearing of debris from the suction extension to allow reinsertion of the suction extension while maintaining the guide catheter in position. Specifically, a fitting element can engage the proximal opening of the suction extension at a docking structure to provide for clearing of the suction extension. In additional or alternative embodiments, proximal fittings can be provided to allow withdrawal of the tubular portion (tubular extension) of the suction extension from the guide catheter without bringing the tubular extension of the suction extension through a hemostatic valve. Methods are described in which a docking fitting docked at the end of the suction extension provide for contact with the fitting while providing for blowing debris from the suction extension, such that the cleared suction extension can then be reinserted through a hemostatic valve and reinserted for the application of additional suction. In a significant number of procedures, the suction nozzle can be cleared one or more times to reopen the clogged vessel. Efficient cleaning of the suction extension can significantly facilitate the procedure.

In some embodiments, the suction extension has a connecting section that has an asymmetric circumference interfacing with the inner surface of the guide catheter with contact at two locations to provide an effective fluid seal while providing for translation of the suction extension within the guide catheter. In alternative or additional embodiments, the guide catheter can have a distal portion of a tubular element that has a narrower diameter that effectively limits the movement of the suction extension in a distal direction. Methods are described for the use of the suction catheter system such that the tubular extension of the suction extension that provides part of the aspiration lumen remains in a sealed configuration with respect to the guide catheter lumen, in some embodiments, for the entire period in which the guide catheter is within a patient Improved processing can be guided through the use of real time line pressure measurements with a pressure transducer associated with appropriate back end tools. Suction catheters can be used advantageously for the removal of thrombus and emboli from bodily vessels, such as arteries. Some vessels can have a narrow diameter, and treatment locations can be downstream along a circuitous path, and for such vessels there are constraints on the catheter structures able to reach the treatment locations in the vessel.

The designs described herein comprise a slidable suction extension that can be adapted for use in conjunction with a corresponding guide catheter, which forms a significant portion of the overall suction lumen when suction extension is deployed from the distal end of the guide catheter. In improved embodiments herein, fittings positioned at the proximal end of the catheter system can be designed to improve the medical procedures to allow for more efficient performance of the revascularization of blocked vessels. Improved efficiencies can reduce time that the patient has catheters in their vasculature and decrease health care professional time devoted to the procedure. While the suction catheter system can be used in any suitable vessels of the body, the system can be particularly desirable in cerebral blood vessels, such as for the treatment of acute stroke. The suction catheter system can be effectively used as a standalone suction catheter for thrombus removal. Furthermore, the suction catheter system can be effective as a component of a thrombectomy treatment system or other medical system to provide suction with the use of other medical devices, such as a clot engagement device, to disrupt thrombus and/or a filter structure that can catch emboli generated in the procedure as well as to be used to pull toward the suction catheter system. The treatment system can be effectively designed for stroke treatment.

Less invasive procedures, which are commonly referred to in the art as minimally invasive procedures, are desirable in the medical context when appropriate to reduce patient recovery times and in many cases to improve outcomes. In particular, less invasive procedures are commonly performed in the vasculature using catheter based system for reaching remote locations in a selected blood vessel for the performance of various treatment processes. These procedures can also be referred to as percutaneous procedures or transluminal procedures, in contrast with open surgical procedures, to emphasize the delivery through a vessel lumen. The discussion herein focuses on treatment of ischemic stroke since the devices can be particularly effective to treat these clinically important conditions, although the devices can be used in other procedures both in the vasculature and other bodily vessels. Patients include humans and can include other mammals, such as pet animals and farm animals. The terms proximal and distal are used in their conventional sense in the art, i.e., proximal refers to closer to the point of entry into the patient along the path in the vasculature or other vessel and distal refers to farther from the point of entry along the path in the vasculature.

A slidable suction extension generally comprises a connecting section that engages the inner wall of the guide catheter to make a suitably tight fit. The connecting section generally links a control structure, such as a control wire, extending in a proximal direction from the connecting section, and a tubular extension that extends from the control structure in a distal direction. The control structure generally extends outside of the patient to provide for positioning the suction extension with its distal tip near a treatment location in a blood vessel. The tubular extension, which may have an optional curved tip, can be tracked well over a guidewire to reach difficult to reach locations in a vessel.

Since thrombus can be held at the distal tip of the suction extension during the application of suction to remove the clot form the vessel, it can be desirable to withdraw a tubular extension of the suction extension into the guide catheter with the application of suction to reduce the chance of embolization of thrombus and loss of emboli that can travel upstream in the vessels. To further reduce the risk of embolization, it can be desirable to fully remove the tubular extension from the guide catheter with the application of suction prior to removal of the guide catheter from the patient. In a significant fraction of procedures, it can be useful to clear the suction extension and reinsert the suction extension for the removal of additional thrombus for the vessel. To achieve the best outcomes, it can be effective to repeat the suction process, two, three or possibly more times.

Desirable proximal fittings at the back end of the catheter system are described that allow for the removal of the tubular extension from the guide catheter without passing the tubular extension of the suction extension through a hemostatic valve. Since the proximal end of the tubular extension generally is open, passage of the proximal end of the tubular extension through a hemostatic valve can expose the interior lumen of the tubular extension and potentially of the guide catheter to the ambient environment, which may or may not be desirable. Additional fitting elements can allow removal of the suction extension through a hemostatic valve for clearing of the catheter while maintaining the fitting on the suction extension at all times, so that the suction extension can be rapidly redeployed. A docking fitting can comprise a distal docking structure that allows for docking the proximal end of the suction extension into the docking structure in an effective fluid tight seal for removal together out from the hemostatic valve. As noted above, this clearing of the suction extension can be repeated more than once.

The proximal fittings provide for the hemostatic isolation of the interior of devices that are exposed to the interior of the blood vessels. A guide catheter then forms an integral component of the aspiration system that provides for introduction of additional components, including but not limited to the suction extension. The fitting can then provide for hemostatic introduction of such other components while also providing for connections to negative pressure devices, such as pumps or syringes, and possibly delivery ports for introduction of contrast dye, medications or other desirable fluids. IV contrast dye fluids are well known in the art. Medications can be delivered in a suitable liquid form. These fitting then provide for the relative movement of the suction nozzle within the guide catheter and out form the guide catheter as well as the other functions.

The control structure for the suction extension can be a wire-like element as described further below. For desirably simple designs of the guide catheter and the suction extension, it can be possible to push the suction extension out the distal end of the guide catheter, which can make it difficult or impossible to retrieve the suction extension from the patient while leaving the guide catheter in place. Markings on the control structure can discourage this movement of the control structure, but a user may disregard the markings. To avoid this possibility, a handle or grip can be secured on the control structure. If appropriate based on the handle design, the control structure can be bent, twisted or otherwise distorted to render it difficult or impossible to remove the handle. The handle then can limit the distal extension of the suction extension within the guide catheter so that the suction extension cannot be extended out of the distal end of the guide catheter.

In some embodiments, suitable proximal fittings suitable for withdraw the tubular extension out from the guide catheter but within hemostatic isolation have a tubular portion of the fittings following a branch structure in which the tubular section has sufficient length to hold the suction extension within the isolated region behind a hemostatic valve but external to the tubular element of the guide catheter. Several suitable configurations are described below and other configurations can follow from the discussion of these embodiments. It can be noted that aspiration is generally applied from a separate branch of the fittings and that multiple branches can be provided in the overall manifold, which may or may not have separable components that are assembled for use. This isolation structure can provide for evaluation of the status of the nozzle prior to withdrawal from hemostatic isolation and can be used in combination with the fitting to provide for effective clearing of the suction extension outside of hemostatic isolation without disconnecting the suction extension for the appropriate fittings.

The measurement of the pressure in the proximal fittings can provide valuable information relative to the procedure. Potential structures for placement of the pressure sensor are discussed below. If the pressure is near zero in the proximal fittings, then the flow in the line to the pump is effectively unconstrained. It is observed that pressure with flow passing through the suction extension results in a measurable drop in pressure but still at a pressure significantly less than the pump pressure. If the suction extension is clogged with thrombus or if the suction extension is kinked, the measured pressure can approximate the pump pressure, which generally indicates that flow is essentially block within the catheter. Knowledge of the blockage can be used to significantly improve the procedure with respect to efficacy and safety. For example, if the blockage occurs early in the procedure, this may suggest kinking. Blockage later in the procedure can suggest blockage of the catheter with trapped thrombus, which generally instructs that contrast dye or other infusion liquids should not be delivered through the catheter since the pressure of delivery can thrust the thrombus, which had been blocking the catheter, deeper into the vasculature. A pressure transducer can be introduced in alternative ways. For example, a pressure transducer can be placed along the inner wall of a fitting of the manifold or on a tube connected to the fittings with a configuration to provide pressure measurements. The pressure sensor may or may not be sterile depending on the location.

For the treatment of strokes, treatment devices can be advanced through arteries to blood vessels of the brain. Blood vessels generally relevant for acute stroke treatment are downstream in the blood flow from the internal carotid arteries, and arteries generally branch and decrease in average diameter as the vessel proceeds in a downstream direction in the arterial vasculature. The body has a right internal carotid artery and a left internal carotid artery. For convenience, the blood vessels downstream from the internal carotid arteries are referred to herein as cerebral arteries. The cerebral arteries can be accessed with catheter based systems from, for example, a femoral artery in the groin, an artery in the arm, or the carotid artery in the neck using hemostatic procedures and appropriate fittings, such as those known in the art. The cerebral arteries are known to follow circuitous paths, and complications in tracking devices along the vessels also follows due to narrow diameters and branching of the vessels as well as potentially dangerous risks from damage to the blood vessel that can cause a hemorrhagic stroke condition. Nevertheless, it can be desirable to access tortuous narrow arteries for stroke treatment. The devices described herein are designed for advantageous use in these tortuous narrow cerebral vessels, but a person of ordinary skill in the art will recognize utility of these devices in other medical procedures.

The present suction catheter systems incorporate guide catheters adapted with a slidable suction extension suitable for cerebral procedures. In vascular procedures generally, a guide catheter can be used to facilitate the delivery of therapeutic devices while allowing for more rapid, accurate delivery with less risk to vessel walls through providing a protected channel leading most of the way to the treatment site. In the cerebral procedures, a guide catheter can be placed from exterior of the patient at the point of entry into the vasculature with the distal end of the guide catheter in a carotid artery or interior carotid artery. Thus, a guide catheter can provide a lumen to a location relatively near to a treatment site. In some embodiments, conventional guide catheters can be used to assemble the desired suction catheter systems, but in other embodiments, specific guide catheter designs are used to form the suction catheter system. The size of the guide catheter sets limits on the diameter of treatment structures delivered to the treatment site, but this is generally not a significant issue since extendable devices can be delivered in a lower profile configuration with subsequent deployments to an extended configuration and since the vessel sizes generally decrease in a distal direction from the guide catheter limiting the need for larger treatment devices. The suction devices described herein provide a suction extension that can protrude from the distal end of the guide catheter an adjustable amount through the positioning of a connecting section of the suction extension interfacing the suction extension with the interior walls of the lumen of the guide catheter. The connecting section can make a sufficiently tight seal with the guide catheter walls such that suction in the guide catheter lumen is transmitted along the lumen of the suction extension. Desirable degrees of suction can be obtained through the suction extension using suction applied at the proximal end of the guide catheter.

The suction extension generally comprises a connecting section, a control structure extending in a proximal direction from the connecting section, and a tubular extension extending in a distal direction from the connecting section. The suction extension generally interfaces with the guide catheter and can be designed to be positioned with its tip at a selected position distal to the guide catheter for the performance of a procedure at a selected location, such as near the location of thrombus occluding a cerebral vessel. Since the relative position of the treatment location and the distal end of the guide catheter generally vary for a specific medical situation, the degree in which the suction extension extends from the guide catheter can be adjusted through relative movement of the suction extension using the control structure, e.g. a control wire. The suction extension should move within the guide catheter lumen without the need for excessive force, which may be facilitated through the use of low friction polymers on one or both adjacent surfaces.

The connecting section of the suction extension provides for an interface with the inner wall of the guide catheter to prevent most or all flow around the connecting section that does not flow through the lumen of the suction extension while keeping at least a portion of the connecting section within the guide catheter and while providing for appropriately unproblematic sliding of the suction extension relative to the guide catheter within the patient's vasculature. Various embodiments of components forming such an interface are discussed in published U.S. patent application 2017/0143938A1 to Ogle et al. (hereinafter the '938 application), entitled "Catheter Systems for Applying Effective Suction in Remote Vessels and Thrombectomy Procedures Facilitated by Catheter Systems," incorporated herein by reference. A connecting section, referred to as a proximal portion in the '938 application, can have a non-cylindrical cross sectional shape. Such a non-cylindrical cross sectional shape can advantageously provide for contact with the guide catheter at two locations around the circumference along with a small clearance around the remaining section of the circumference of the connecting section. Contact with the inner lumen of the guide catheter applies some force on the connecting section that partially rounds out the circumference. This non-cylindrical shape for the connecting section allows for effective blockage of flow between the guide catheter wall and the connecting section while not inhibiting movement of the connecting section longitudinally to position the tip of the suction extension within the vasculature. The introduction of a non-cylindrical shape of a connection section is described in U.S. Pat. No. 10,478,535B2 to Ogle (hereinafter the '535 patent), entitled "Suction Catheter Systems for Applying Effective Aspiration in Remote Vessels, Especially Cerebral Arteries," incorporated herein by reference.

The non-circular cross sectional shape of the connecting section of the suction extension can generally be described as oval. The oval can be characterized at least in part by a major axis along the longer dimension of the oval and a minor axis along the shorter dimension of the oval orthogonal to the longer dimension. The connecting section can then contact or approach very closely to the inner surface of the engagement section of the guide catheter at two locations associated with the points along the circumference associated with the major axis. Correspondingly, the non-circular cross section can be characterized by an average radius, and the average radius can provide an overall very small clearance with the guide catheter while still providing for desirable function.

To form the non-circular cross section, a bump can be formed through the connection of a control wire along a surface of the connecting section along with extra polymer that provides for the desired shape along with reinforcing the control wire connection with the connecting section. Additional embodiments of the connecting section structure with an oval cross section are described below. Thus, the non-circular shape of the connecting section cross section can be designed for its interface with the guide catheter consistently with the overall structure of the suction extension.

Also, since it is desirable to prevent the connecting section of the suction extension from exiting from the distal end of the guide catheter, the suction extension and/or catheter can be designed to limit the distal movement of the suction extension. Several different designs of guide catheter and/or suction extension features are described in the '938 application and the '535 patent. To simplify the guide catheter structure and/or to provide for use of a conventional guide catheter design, it can be desirable to use a guide catheter without any specific structural features that limit the distal movement of the suction extension. But then movement of the suction extension should be limited through motion of the control structure. Instructions to the user based on marking on the control structure are prone to user error that allow for over extension of the connection section of the suction extension out past the distal end of the guide catheter. The elements added to the control structure described herein prevent the user from over extending the suction extension.

In comparison with a suction catheter delivered through the guide catheter in which the suction flow is confined to the suction catheter, a significant length of the suction catheter is replaced with a control element in the suction catheter systems herein. This replacement of a significant length of a suction catheter with a control element results in a device that can have less friction when the tip of the suction catheter is advanced in the patient's vasculature since a control wire or other control element can offers less resistance for its movement. The tip of the suction extension can be given a curved tip to facilitate tracking of the device over a guidewire. With the designs described herein, a suction extension for aspiration with a curved tip for tracking the tip over a guidewire can be effectively guided to difficult to reach locations with the use of a control wire or other control element moving the slide portion at or near the distal end of the suction extension, and the design provides for good suction ability without sacrificing the ability to reach difficult to reach vessels, such as within cerebral vessels. While the suction extension is moved, the guide catheter portion of the suction lumen can remain in place When suction is applied at or near the proximal end of the guide catheter with a suitable negative pressure device, fluid is sucked into a distal opening at the end of the suction extension. It has been found that strong suction can be transmitted through to the suction extension. A suction lumen extends from a negative pressure device, generally attached at a fitting associated with a proximal section, at or near the proximal end of the suction system through the guide catheter lumen to the suction extension and through the connecting section of the suction extension and the tubular extension of the suction extension to a distal opening. Suitable negative pressure devices include, for example, syringes, pumps or the like. The guide catheter can provide a large lumen as a significant section of the overall suction lumen. The effective suction lumen then can appear to have a large proximal section contributed by the guide catheter and a tapered distal section contributed by the suction extension, which can have one or more tapered segments.

The tubular extension of the suction extension has a lumen with a reduced diameter relative to the guide catheter lumen and good flexibility to provide for placement of its distal end into smaller vessels. The lumen of the tubular extension though is maintained at a sufficiently large diameter that provides for delivery of additional therapeutic devices through the lumen to the treatment location. The outer diameter at the tip of the suction extension generally is (diameter in mm=(Fr value)/3, Fr represents the French catheter scale) at least about 1.5 Fr less than the outer diameter of the distal section of the guide catheter. The smaller diameter of the tubular extension can provide access to desirable vessels, such as cerebral vessels.

It was previously discovered that good suction properties could be obtained with a suction catheter with a stepped down diameter in a distal section. Thus, for example, the majority of the length of the suction catheter can be 6 Fr outer diameter while a distal section may be 5 Fr outer diameter, which roughly corresponding decreases in the inner diameters. Such a catheter can provide access into vessels suitable for a 5 Fr catheter, but can provide significantly better suction than a suction catheter with a 5 Fr catheter body along its entire length. Commercial stepped down suction catheters, such as Mi-Axus™ catheters (MIVI Neuroscience, Inc.) and ACE™ 64 catheters (Penumbra, Inc.) are finding good clinical results. The step down suction catheters and their use for thrombectomy procedures in cerebral arteries are described in U.S. Pat. No. 9,532,792 B2 to Galdonik et al. (hereinafter the '792 patent), entitled "Aspiration Catheters for Thrombus Removal," incorporated herein by reference. While these catheters achieve better suction than catheters with constant diameters corresponding with the distal diameters, the present suction catheter systems with a sliding suction extension are found to provide better suction suggesting that the diameter over the majority of the suction lumen length contributes to a large extent to the suction provided at the distal opening of the suction lumen.

An initial part of a procedure using the devices described herein generally involves accessing the treatment location within the vasculature. Guidewires have been designed to facilitate access to difficult to reach locations. The term guidewire is used herein to refer broadly to wire structures that may or may not have internal structure are referred to as guidewires whether or not they are formed from a solid or woven metal, such as corewire-overtube integrated structures, coils or the like which may not have a closed inner lumen over at least a portion of the devices length.

In particular, with the devices described herein procedures can be performed to provide re-profusion in vessels that are blocked completely or partially with clots. Clots in cerebral arteries can cause strokes with corresponding serious consequences, and time generally is of the essence of treating these conditions. The suction extension with the guide catheter can be used to provide aspiration that can be useful to remove clots or fragments thereof. Thus, the suction extension combined with the guide catheter and negative pressure device can be used as stand-alone devices for thrombectomy procedures. However, the suction extension with aspiration can be effectively used as part of a treatment system comprising, for example, also a fiber based filter and/or other components to facilitate removal of a clot or portions thereof. The delivery catheter with the expandable tip is designed to facilitate access, so it is useful as a tool for the practice of various other procedures.

In some embodiments of the procedure, a guidewire can be placed at or near an occlusion and a guide catheter with a positionable suction extension can be placed in the vasculature upstream from the occlusion with the guidewire extending through the interior of the suction extension. If the suction catheter system is to be used alone, then the suction extension can be advanced using a control wire over the guidewire to a suitable position near the clot. Then, with or without removing the guidewire, suction can be initiated to suck the clot or a portion thereof into the distal opening or against the tip of the suction extension. Suction may or may not be continued as the suction extension and/or guide catheter are removed from the patient.

While suction with the suction extension can be effective as the only device for clot removal, additional treatment systems can combine other devices for use with the suction catheter system. In particular, a filter device can be used to provide both embolic protection as well as a tool to facilitate removal of the clot or portions thereof, which may involve direct engagement of the clot with the filter device. Fiber based filters/embolic protection systems have been developed that can be effectively used in the narrow vessels of interest. In particular, fiber-based filter systems with an appropriate actuation system can be used for delivery in a low profile configuration past an occlusion and deployed to provide protection from any clot fragments that may be released during the removal process.

During the removal process of the suction catheter system and potentially other components of the treatment system from the patient, aspiration generally is continued until risk for embolization of thrombus is sufficiently lowered. The suction extension may have thrombus within the lumen and/or trapped at the tip. The proximal end of a tubular section of the suction extension generally is open such that if the proximal end of the tubular extension is removed through a hemostatic valve, the suction lumen of the tubular extension can be exposed to the ambient environment. Since exposure of the lumen of the tubular extension still within the patient can be undesirable, fittings have been devised as described herein that allow parking of the tubular extension external to the guide catheter while still within isolated sections of the system external to the patient. Aspiration can be continued while the tubular extension is removed from the patient and parked in isolation from the ambient but external to the guide catheter.

In some procedures, it may be desirable to clear the tubular extension while it is removed from the patient. Once cleared, the tubular extension can be reintroduced into the patient to retrieve additional thrombi. In such procedures, a docking branched manifold can be configured to facilitate the rapid removal and cleaning of the tubular extension. It is desirable to return the extension catheter to the vascular before embolization of thrombus at the clot. The docking branched manifold generally has an input tubular segment and at least one Y-branch having a fitting connected at the end of one branch to a flow valve. The flow valve generally has at least a second port connected to a flush fluid source, although in some embodiments, the flow valve or additional flow valves can be used to control alternative fluid sources and/or an aspiration source. The docking branched manifold generally has a second branch having a hemostatic valve. The docking branched manifold has a tubular input at the distal end which includes a docking structure. The docking structure can pass through the hemostatic valve of the first branched manifold such that it can be positioned within the tubular segment of the first branched manifold.

The docking branched manifold generally can be used to flush the catheter using fluid from a fluid source, such as a syringe, pressurized vessel or a pump connected to a reservoir. The docking branched manifold can be equipped with a plurality of fluid sources, such as a contrast fluid source, a therapeutic agent fluid source, and/or a flush fluid source, such as buffered saline, although contrast fluid can also be used for flushing a clogged catheter. Also, aspiration can be delivered into the aspiration system from the docking branched manifold as an alternative or in addition to configuring aspiration to be delivered from the first fitting element, which may then optionally not include a manifold, such as shown in the figures described above. If the docking branched manifold is used to deliver a second fluid and/or aspiration as well as any further fluids, the docking branched manifold can comprise additional branches and/or additional branching along a second branch.

Generally, a control structure of the suction extension extending proximally can pass through a hemostatic valve with the valve closing around the control structure with an appropriate seal. Generally, the control structure can pass through both the hemostatic valve of the first branched manifold and the hemostatic valve of the second branched manifold so that it can be manipulated externally to the manifolds. The docking structure can slide over the control structure. In this configuration, the proximal end of the tubular extension can be drawn into a docked position with the docking structure. The docking structure may be configured to releasably retain the tubular extension. For example, the docking structure may use an interference fit to secure the tubular extension. In embodiments, the docking structure can include a narrowing of the internal walls of the tubular input portion. For example, an interior surface of the tubular input may taper inwards until the interior diameter of the tubular input is less than the outer diameter of the tubular extension. In alternative or additional embodiments, the docking structure may include a flange on an interior surface of the tubular input. In embodiments, the docking structure may include a material on the interior surface of the tubular input configured to create a frictional fit to secure the tubular extension. In embodiments, the docking structure may include a structure on the interior surface of the tubular input configured to interface with a corresponding structure on an exterior surface of the tubular extension. For example, the docking structure may include a detent on the interior surface of the tubular input configured to interface with an indent on the exterior surface of the tubular extension.

With the tubular extension docked in the docking structure, the docking manifold may be disengaged from the first manifold. The docking branched manifold can be separated along with the suction extension by opening the hemostatic valve on the first fitting element, pulling the docking branched manifold away from the first fitting element, and resealing the first hemostatic valve when the tubular extension is clear of the valve. When the tubular extension is outside of the first fitting element, thrombus trapped within may be cleared out from the tubular extension. Opening the source valve attached to the docking branched manifold permits fluid to flow through the tubular extension. Fluid may flush the thrombus and any other debris or material trapped within the tubular extension. Once the tubular extension is clear it may be returned to the patient. It may be desirable to re-sterilize any components that have been exposed to the environment before reintroducing them into the patient, although generally the suction extension is maintained in a sterile condition outside from the patient so that it can be returned to the vasculature without further sterilization. To reintroduce the tubular extension, the first hemostatic valve of the first fitting element should be opened thereby permitting the tubular extension and docking structure to enter the first fitting element. With the docking structure in place within the first fitting element, the hemostatic valve may be tightened. The control structure may be used to move the tubular extension out of the docking structure, into the guide catheter, and back to a desired position within the patient. In some instances, aspiration may remain on while the tubular extension is cleared. In other instances, it may be preferable to halt aspiration when the tubular extension is not deployed in the guide catheter.

Following the completion of the revascularization of the vessel, the catheters are removed from the patient. Depending on the particular fittings used, several alternative procedures can be used to safely remove the catheters. If the fittings have an isolation section to remove the suction extension within the hemostatic seal, with the tubular extension safely parked external to the guide catheter, the procedure can be completed, which generally involves termination of suction and confirmation that the blockage is resolved. At the end of the procedure, the guide catheter can be safely removed from the patient. If the fittings do not include an isolation section, the suction extension may or may not be removed through a hemostatic valve prior to removal of the guide catheter. If the suction extension is not removed through a hemostatic valve to isolate it from the guide catheter, the distal end of the suction extension is generally located safely within the guide catheter lumen when the guide catheter is removed, and aspiration may be continued during at least a portion of the procedure involving the removal of the guide catheter.

In some embodiments, throughout the part of the procedure in which aspiration is applied, the pressure in the proximal fittings can be monitored. If the pressure in the proximal fittings remains within an expected range, the physician performing the procedure can proceed based on that knowledge. If the pressure increases, the physician can take appropriate actions, such as removing the suction extension from the patient, generally without the delivery of fluid through the tubular extension.

The devices and corresponding processes described herein provide improved functionality for performing therapeutic procedures for the removal of clots from vessels. As noted herein, the devices can be used in various combinations within medical systems for percutaneous procedures. Improved procedures provide additional safety measures while providing practical steps for performance by the medical professional handling the devices.

Suction System with Sliding Suction Extension

Suction Systems are described that take advantage of good suction available with a suction catheter lumen having a larger proximal suction and a narrower diameter suction extension that uses the guide catheter lumen as a proximal suction lumen. A laterally slidable suction extension extends from a proximal section located within the guide lumen, and the suction extension can have a smaller distal diameter to provide access to narrow vessels while providing for delivery of other treatment structures and/or embolic protection structures as well as for a desirable level of suction for the removal of debris from the vessel. A control wire or other control structure can be attached to the suction extension to control sliding for providing selective lateral placement of the suction extension relative to a fixed guide catheter and a target treatment location. In some embodiments, the suction extension comprises a connecting section that interfaces with the guide catheter lumen with a non-cylindrical cross section to provide for contact at two parts along the circumference. This non-cylindrical interface can block flow between the exterior of the proximal portion of the suction extension and proximal locations in the interior of the guide catheter while allowing relatively easy sliding of the suction extension relative to the guide catheter. A specific guide catheter design can incorporate various tubular elements along its shaft to provide for desired flexibility and a narrower diameter distal tubular element can be used to retain the proximal section of the suction extension within the guide catheter lumen.

Referring to FIG. 1, suction system 100 comprises a suction adapted guide catheter 102 and a suction extension 104. The suction adapted guide catheter 102 comprises proximal section 106 and tubular shaft 108. Proximal section 106 generally is suitable for use also as a handle and generally can comprise a proximal fitting 120, a suction port 122 and an optional control wire port 124, as well as possibly other additional ports and/or fittings to provide desired functionality and access, in which all such ports and fittings can be arranged in a branch configuration or other suitable configuration. In general, proximal fitting 120 can comprise a suitable hemostatic valve, luer fitting or the like to provide for entry of a guidewire and/or structures delivered over the guidewire into the guide catheter lumen, such as alternative treatment structures and/or embolic protection devices.

In improved embodiments described herein, proximal fitting 120 can comprise a segment in which a tubular extension of suction extension 104 can be placed without extending into tubular shaft 108 of guide catheter 102 or through a hemostatic valve into the ambient environment. While desired features of fittings at the proximal end of the suction system 100 can be integral with proximal fitting 120, design flexibility can be achieved through embodiments of proximal fitting 120 comprising a connector, such as a Tuohy-Borst connector, and connection of fittings providing other desired features, such as a Y-branch, hemostatic valve, an extended tubular fitting to store the tubular extension of suction extension, etc. as fitting components that are attached for use to proximal fitting 120. Suitable fittings with additional functional features for incorporation with proximal fitting 120 are described in detail below in the treatment system section with an understanding that this disclosure below may be considered as integral portions of proximal fitting 120 rather than separate components.

For use with suction system 100, suitable embolic protection devices can be mounted on a guidewire, and/or other treatment structures can be used. Suitable treatment structures are described further below and can include, for example, fiber-based filters, stents, stent retrievers, atherectomy devices or the like. As shown in FIG. 1, a negative pressure device 126 is shown connected with suction port 122, and suitable negative pressure devices include, for example, syringes, pumps, such as peristaltic pumps, piston pumps or other suitable pumps, aspirator/venturi, or the like. Suitable pumps are available from Allied Healthcare Products, Inc., such as a Gomco™ brand pump, or a DRE DM-660™ pump.

In general, tubular shaft 108 can have an approximately constant diameter along its length, or some guide catheters can have sections with different diameters, generally with a smaller diameter section distal to a larger diameter section. In some embodiments described herein, a significant of the length of the tubular shaft has a constant diameter to make desired contact with a connecting section of the suction extension, which can be called an engagement section of the tubular shaft designed to engage the suction extension in a configuration suitable for the delivery of suction to a patient. Portions of the tubular shaft proximal to the engagement section can have a larger inner diameter and generally larger outer diameter relative to the engagement section. While a conventional guide catheter can be used in some embodiments for the suction catheter system, a specific design is described in detail below. A distal tubular portion of the tubular shaft can have a slightly narrower inner diameter to retain a portion of suction extension 104 within tubular shaft 108. Tubular shaft 108 can have one or more radiopaque marker bands to facilitate positioning of the tubular shaft within the patient as well as positioning the connecting section of the suction extension within the guide catheter lumen, and FIG. 1 shows a marker band 128 near the distal end of tubular shaft 108, although alternative positions can be used as desired. As described below, tubular shaft 108 can have coatings on the inner surface and/or the outer surface or portions thereof.

Suction extension 104 generally comprises a connecting section 140, tubular extension 142, and control structure 148, such as a control wire. All or a part of connecting section 140 can be configured to remain within the lumen of guide catheter 102. As shown in FIG. 1, connecting section 140 can comprise a radiopaque marker band 152, although connecting section may not have a marker band in some embodiments and in other embodiments can comprise a plurality of marker bands, and tubular extension 142 is shown with radiopaque marker band 154 near the distal tip of tubular extension 142, although again tubular extension 142 can comprise a plurality of radiopaque marker bands if desired. Control structure 148 can be a control wire or the like that connects with proximal portion 140 and in the assembled device extends exterior to the catheter, such as exiting through control wire port 124 or proximal fitting 120. Control structure 148 can be used to control positioning of connecting section 140 within the lumen of tubular shaft 108. Control structure 148 can comprise a control tool 156, such as a handle, slide or other the like that can anchor a control wire or other connecting element to facilitate movement of the control wire. In some embodiments, alternative structures such as a plurality of wires or cylindrical wire assembly can connect the proximal portion to the proximal end of the suction catheter system to provide a desired level of control with respect to positioning the proximal section.

As noted above, the connecting section of suction extension engages the inner lumen of the guide catheter with an appropriate interface to reduce or eliminate flow of blood between the connecting section of the suction extension while allowing for the user to translate the suction extension relative to the guide catheter to position the tip of the tubular extension. A desirable design with a connecting section of the suction extension having a non-circular cross section has been found to particularly meet these criteria. With material selection as described herein, a very small average clearance can also be used between the connecting section of the suction extension and the interior of the guide catheter. When assembled, the inner lumen of the guide catheter can contact the connecting section of the suction extension at two locations around the circumference, which can provide partial rounding the cross section of the connecting section. This two location contact configuration provides desirable confinement of the flow while allowing for sliding of the suction extension by the user with appropriate ease.

The non-circular cross section of the connecting section (or a portion thereof) of the suction extension generally can be roughly oval in shape. While not intending to be limited by this term, in some embodiments, the cross section can have one axis of symmetry resembling the cross section of a conventional egg. As described below, the oval shape can be generated through the attachment of a wire control structure to the proximal section, although other structural features can be used to introduce the oval shape, such as with approximately one axis of symmetry or two axes of symmetry, although the oval can be asymmetric. Generally, the oval cross section can be partially characterized by a major axis, e.g., the longer dimension along an axis of symmetry, and a minor axis, e.g., the longest line segment connecting the circumference perpendicular to the major axis. While the specification of the major axis and the minor axis does not fully specify the oval since the specific shape is not specified, the major and minor axes can provide significant information regarding the dimensions and relative shape of the oval, especially since the shapes are generally not far out of a circular shape. Also, an average clearance can be defined using the largest value of the circumference (C) of the oval cross section and converting to an equivalent circle to define an approximate average diameter ($D_a = C/\pi$).

An embodiment of a guide catheter is shown in FIGS. 2-4. Referring to FIG. 2, guide catheter 160 comprises a connector fitted hub 162 with a portion of a Tuohy-Borst connector, luer connector or the like, shaft 164 and strain relief support 166. In this embodiment, the proximal end of shaft 164 passes through strain relief support 166 to connector fitted hub 162, and the components can be secured together with adhesive. Also, female connector 168 is located at the proximal end of connector fitted hub 162 for connection to a male connector fitting on a proximal fitting, such as a branched connector, which may have a rotating hemostatic valve with one or more branches.

A sectional view of a portion of shaft 164 near the proximal end is shown in FIG. 3. Referring to the embodiment of FIG. 3, shaft 164 comprises a polymer tube 180 with an embedded stainless steel wire braid 182 and a lubricious liner 184, e.g., polytetrafluoroethylene (PTFE) or other fluoropolymer. FIG. 4 shows the distal end of shaft 164. As shown in FIG. 4, a radiopaque marker band 186 is embedded in the polymer tubing near the distal end of shaft 164. Also, a distal section 188 of tubing is placed at the distal end of shaft 164 with a slightly reduced inner diameter, as explained further below. As shown in FIGS. 3 and 4, the metal braid ends adjacent marker band 186 (or overlaps with the marker band and terminates after), and distal section 188 is free of metal braiding in this embodiment. As described further below, the composition of the polymer tubing included in the shaft can vary along the length of shaft 164, for example, to increase flexibility of the shaft toward the distal end of the shaft. In some embodiments, different adjacent sections of polymer tubing can be heat bonded together and further supported with an overarching metal braiding and/or coil reinforcing the majority of the shaft. In some embodiments, the majority of the shaft 164 can have a constant inner diameter, except for distal section 188, to provide for the application of suction through the suction extension positioned at any location within the guide catheter proximal to distal section 188. But in alternative embodiments, a proximal section of shaft 164 can have a larger diameter if desired since the proximal section of the guide catheter may not be used for positioning the connecting section of the suction extension for the application of suction. Appropriate markers on the control wire can be used to ensure that the suction extension is positioned properly for the application of suction.

A lubricious coating, for example, a hydrophilic coating, can be placed on the outer surface of shaft 164 or a portion thereof. Suitable hydrophilic coatings include, for example, polyvinyl alcohol, heparin based coatings, or the like. Hydrophylic coating solutions are commercially available, such as LUBRICENT® (Harland Medical Systems, MN, USA) or SERENE™ (Surmodics, Inc, MN, USA). Further description of the materials and manufacturing process are provided below.

The guide catheter can have an outer diameter (D) from about 5.5 Fr (1.667 mm diameter) to about 10 Fr (3.333 mm diameter), in further embodiments from about 6 Fr (1.833 mm diameter) to about 9 Fr (3 mm diameter), and in some embodiments from about 6.25 Fr (2 mm diameter) to about 8.5 Fr (2.833 mm diameter). The guide catheter measurement are generally referenced to the outer diameter, and the inner diameter is less than the outer diameter by twice the wall thickness. In general, the inner diameter of the main portion of shaft 164 ($d_1$) can range from about 0.8 mm to about 3.175 mm, in further embodiments from about 0.9 mm to about 2.85 mm and in additional embodiments from about 1.00 mm to about 2.7 mm. The reduction in inner diameter of distal section 188 ($d_2$) relative to the inner diameter of an engagement section of shaft 164 ($d_1$) can be from about 0.034 mm (0.00134 in) to about 0.25 mm (0.0098 in) and in further embodiments from about 0.05 mm (0.002 in) to about 0.20 mm (0.0079 in). The length of the guide catheter shaft can be from about 30 cm to about 150 cm, in further embodiments from about 35 cm to about 130 cm and in additional embodiments from about 40 cm to about 120 cm, and is generally selected to be suitable for the corresponding procedure. In some embodiments, distal section 188 can have a length ($L_d$) from about 1 mm to about 50 mm, in further embodiments from about 1.5 mm to about 25 mm, and in other embodiments from about 2 mm to about 20 mm. A person of ordinary skill in the art will recognize that additional ranges of dimensions within the explicit ranges above are contemplated and are within the present disclosure.

For use of the guide catheter of FIG. 2 to form analogous proximal fittings of FIG. 1, a Y-branch hemostatic valve connector 190 can be used, such as the embodiment shown in FIG. 5. Y-branch hemostatic valve connector 190 comprises a male connector 192, a Y-branch frame 194 with branching flow channels, rotating hemostatic valve 196, connector 198, tubing 200 connected to Y-branch frame 194 at connector 198, and suction device 202 connected to tubing 200. Male connector element 192 can be attached to female connector element 168 of FIG. 2. As schematically shown in FIG. 5, a control wire 204 and a guidewire 206 are both shown exiting hemostatic valve 196, and guidewire 206 can be used to guide therapeutic devices through a guide catheter through the hemostatic valve. Various branched hemostatic valve connectors are available from commercial suppliers, such as Merit Medical, UT, USA. More generally, a range of fittings can be attached to connector fitted hub 162 of guide catheter 160, and improved embodiments of fittings with a portion for placement of the tubular extension of the suction extension are described in more detail under the treatment systems section below.

An embodiment of a suction extension is shown in FIGS. 6-12. Referring to FIG. 6, suction extension 230 comprises a control wire 232, connecting section 234 and tubular extension 236. Connecting section 234 connects with control wire 232, which extends in a proximal direction from the connecting section, and tubular extension 236, which extends in a distal direction from the connecting section. In general, control wire 232 can be a solid wire, coil or the like that provides for transmission of pulling and pushing forces to connecting section 234, which correspondingly can move with the tubular extension 236 relative to a guide catheter in the assembled suction catheter system. Control wire 232 can have any reasonable cross sectional shape, which can be different at different locations along the length of the control wire. Also, the control wire can be tapered to a smaller circumference toward the distal end of the control wire. Generally, control wire 232 is made of biocompatible metal, such as stainless steel, titanium or the like, although other materials that have appropriate balance of rigidity and flexibility can be used in principle. In some embodiments, the control wire is a round metal wire with an average diameter along its length from about 0.010 inches (0.254 mm) to about 0.040 inches (1.01 mm) and in further embodiments from about 0.0125 inches (0.32 mm) to about 0.030 inches (0.76 mm). The length of control wire 232 is generally somewhat longer than the guide catheter so that the guide wire extends from the proximal end of the guide catheter, such as 5 cm or more longer than the guide catheter. A person or ordinary skill in the art will recognize that additional ranges within the explicit dimensional ranges above are contemplated and are within the present disclosure.

Connecting section 234 generally is distinguishable by a larger outer diameter than tubular extension 236, and tubular extension 236 extends from the connecting section 234 in a distal direction. In the embodiment of FIGS. 6-12, tubular extension 236 has an approximately constant outer and inner diameter, and a further embodiment is described below with a step down diameter along the tubular extension. Referring to a sectional view in FIG. 10, tubular extension comprises a polymer tube 240, a metal coil reinforcement 242 and a radiopaque marker band 244. Metal coil reinforcement 242 can comprise a flat metal wire, which can extend in some embodiments from roughly radiopaque marker band 244 to a radiopaque marker band in connecting section 234, described further below, although the metal coil reinforcement can extend over the marker bands. Polymer tube 240 can remain the same along the length of tubular extension 236, or the polymer can be changed as different positions along tubular extension 236, for example, getting more flexible in a distal direction. Different sections of polymer can be heat bonded during construction, and metal coil reinforcement 242 as well as optionally a polymer overlayer can further stabilize connected sections of polymer tubing. A tip 246 of tubular extension 236 distal to radiopaque marker band 244 can comprise polymer tubing 240 free of metal reinforcement. A low friction liner 248, such as PTFE or other fluoropolymer, can extend along the length of tubular extension 236 and/or connecting section 234, or portions thereof.

Figure 7:
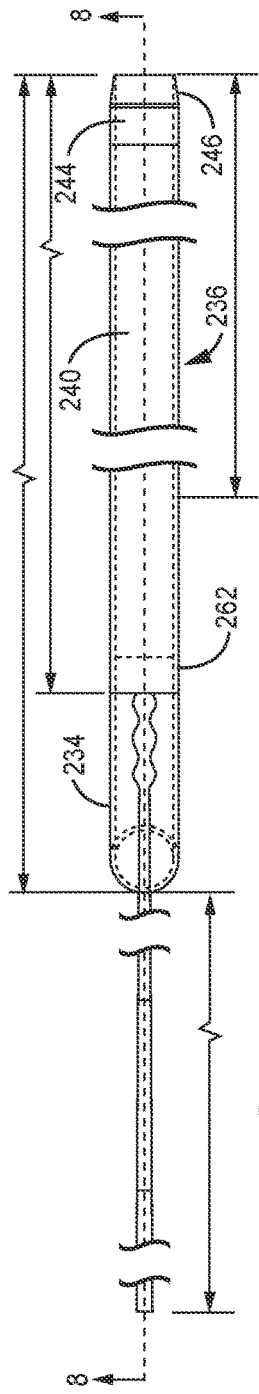
FIG. 7 is a top view of the suction extension of FIG. 6 with some hidden structure shown with dashed lines.
Figure 8:
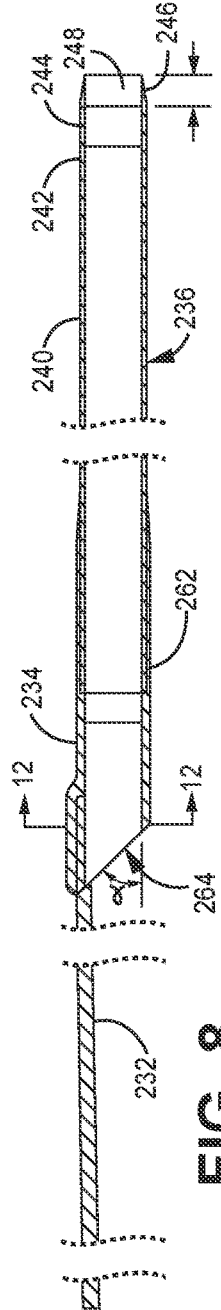
FIG. 8 is a sectional side view of the suction extension of FIG. 6 taken along line 8-8 of FIG. 7.
Figure 9:
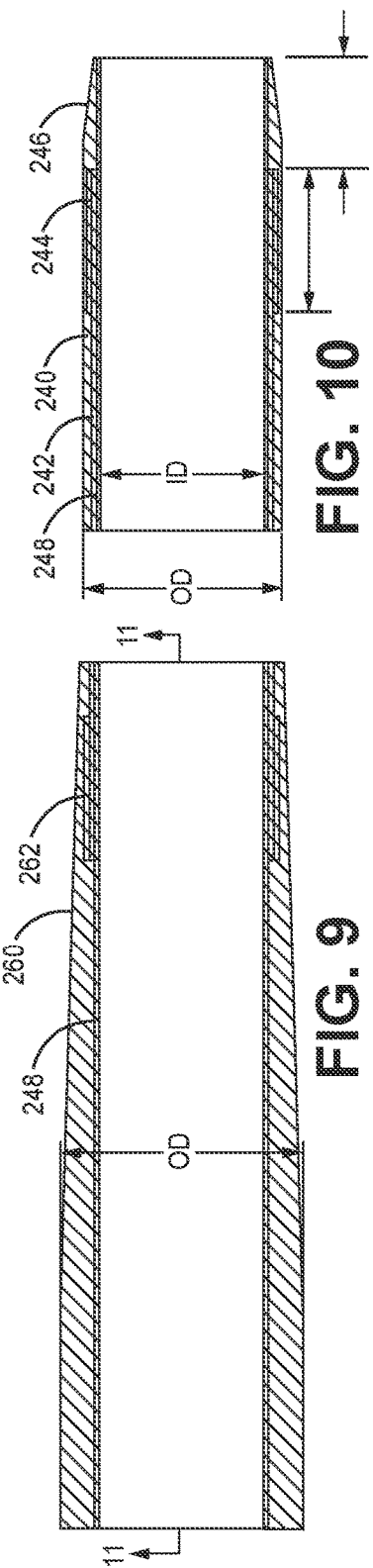
FIG. 9 is a fragmentary sectional view taken along line 9-9 of FIG. 6.
Figure 10:
FIG. 10 is a fragmentary sectional view taken along line 10-10 of FIG. 6.

The relationship of connecting section 234 with control wire 232 and tubular extension 236 are shown in FIGS. 6-8. Sectional views of portions of connecting section 234 are shown in FIGS. 9, 11 and 12 and show certain details of the structure. Connecting section 234 can comprise polymer tubing 260 and radiopaque marker band 262. Polymer tubing 260 has a proximal opening 264 that can be angled relative to a longitudinal axis of the polymer tubing to facilitate delivery of devices through the suction extension, although a right angle can be used if desired. The angle α is marked on FIG. 8 and can range from 25 degrees to about 85 degrees, in further embodiments from about 30 degrees to about 80 degrees, and in additional embodiments from about 33 degrees to about 75 degrees. A person of ordinary skill in the art will recognize that additional ranges of angles within the ranges above are contemplated and are in the present disclosure.

The interface of control wire 232 with connecting section 234 can serve the purpose of both securing the components together as well as helping to form the shape of connecting section 234, which can be selected to provide a desired interface with the interior of the guide catheter lumen. Specifically, the connection of the control wire with the connecting section can facilitate the formation of the oval cross section of the connecting section. In alternative embodiments, control wire 232 can terminate with a flat wire coil that is embedded into a polymer tube to substantially maintain the shape of the connecting section, as described in the '938 application and below. In additional or alternative embodiments, an oval shape of the connecting section can be introduced through the molding or other shaping of the polymer which may or may not be combined with a bump due to an embedded control wire. Suitable dimensions of the oval cross section and the processing to form the connecting section are described further below. Low friction liner 248 can extend through the inner lumen of connecting section 234, as shown in FIGS. 9 and 11, or in some embodiments a separate low friction liner can be included in connecting section 234 if desired.

Figure 22:
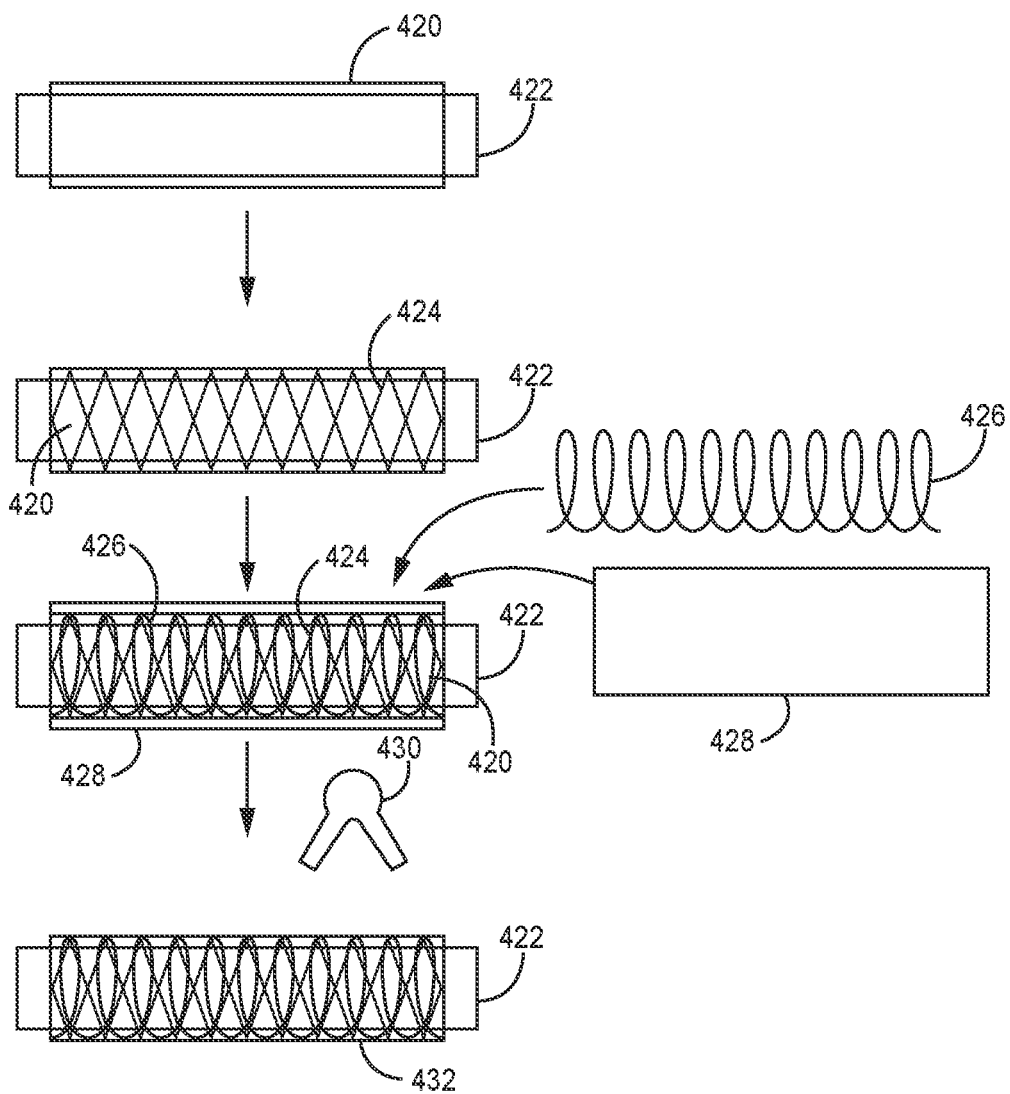
FIG. 22 is a series of side views depicting the construction of a catheter structure on a mandrel in which one or more steps are performed including application of a wire braiding, placement of a metal coil, application of a polymer over sheet and heating the polymer to embed the metal structures within the polymer.

Referring to FIGS. 8, 11 and 12, the distal end of control wire 232 is embedded in polymer associated with polymer tubing 260. Supplementing the polymer wall to secure control wire 232 alters the cross sectional shape that results in a major axis ($L_M$) greater than the minor axis ($L_m$), as can be seen clearly in FIG. 12. As noted above, the non-circular cross section is advantageous for the interface of the suction extension with the guide catheter. The cross section of an alternative embodiment of a connecting section 280 with a non-circular shape is shown in FIGS. 13 and 14. In this embodiment, a flattened metal coil 282 at the end of a control wire 284 is embedded in a polymer tube 286 with a noncircular cross section. The non-circular cross section is formed in this embodiment through forming the polymer with a thicker wall along one edge of the circumference, as can be seen in the sectional view of FIG. 14. A corresponding circular embodiment is shown in FIGS. 21 and 22 of the '938 application. The connecting section may or may not have an approximately constant outer diameter over its length, and the outer diameter may taper, e.g. a gradual taper, step-wise taper or combination thereof, over at least a portion of its length to roughly the outer diameter of the adjacent section of the tubular extension.

In some embodiments, the proximal end of connecting section is suitable for docking in a docking element of a fitting element to provide for removal of the suction extension from hemostatic isolation in association with the fitting element. Such a fitting docked with the suction extension can be used to clear clots from the suction extension in the docked position. Once cleared of clots, the suction extension can be reintroduced into the patient for further use to remove additional thrombus from the patient's vessel. Suitable fittings are described in detail below.

An alternative embodiment of a suction extension is shown in FIGS. 15 and 16. Suction extension 300 comprises control wire 302, connecting section 304 and tubular extension 306. Control wire 302 and connecting section 304 can be analogous to control wire 232 and connecting section 234, respectively, for the embodiment of FIGS. 6-12. Referring to FIG. 16, the distal end of control wire 302 is embedded in polymer within connecting section 304 forming a distension 308 along a surface of connecting section 304. A proximal opening 310 into the lumen of connecting section 304 forms an angle α with respect to the axis of connecting section 304. Connecting section 304 comprises a radiopaque marker band 312. The body of connecting section 304 is a polymer tube 314. Low friction liner 316, such as PTFE or other fluoropolymer, can extend along the lumen of connecting section 304 and/or tubular extension 306 or selected fractions thereof. Metal reinforcement, such as a flat metal wire coil, can reinforce polymer tube 314 or a fraction thereof. As shown in FIG. 16, flat metal wire coil 318 is embedded through the polymer tube 314 distal to radiopaque marker band 312 and extending to tubular extension 306. Furthermore, the asymmetric cross section shown in FIGS. 12 and 14 as well as the control wire attachment approaches of FIGS. 11 and 13 can apply also to the embodiment of FIGS. 15 and 16.

Referring to FIGS. 15 and 16, tubular extension 306 comprises a first tubular section 330, taper section 332 and second tubular section 334 having a smaller diameter than first tubular section 330. Taper section 332 tapers between the diameter of first tubular section 330 and the diameter of the second tubular section 334. Second tubular section 334 comprises a radiopaque marker band 336. Flat metal wire coil 318 extends from radiopaque marker band 336 to radiopaque marker band 312 within connecting section 304, embedded within a polymer tube. The end of second tubular section 334 distal to radiopaque marker band 336 can be free of metal reinforcement. As noted above, a low friction liner 316 can extend along lumen wall for the length of tubular extension 306 or a selected fraction thereof. The body of the first tubular section 330, taper section 332 and second tubular section 334 generally comprises a thermoplastic polymer tube. Sections of polymer tube can be heat bonded together and further supported by the embedded flat metal wire coil 318, optionally with heat shrink polymer film or the like covering the metal reinforcement. A fragmentary sectional view of first tubular section 330 is shown in FIG. 17 with flat metal wire coil 318 shown embedded in polymer tube 338, and cross sectional views of taper section 332 and second tubular section 334 would show similar construction. The composition of the polymer tube can vary along the length as desired to select a particular flexibility, generally more flexible toward the distal end of the device, and the polymer composition can be varied for the different section 330, 332, 334 and/or within the sections.

As shown in FIGS. 15 and 16, taper section 332 provides an approximately linear transition of diameters from the wider diameter of first tubular section 330 to the narrower diameter of second tubular section 334. In alternative embodiments, a taper section can have nonlinear changes in diameter if desired, but the change is generally monotonic. The taper section can be formed through an extrusion process or through conforming of a thermoplastic polymer to a mandrel shape or other suitable process approach known in the art.

A significant aspect of the suction extension is the narrower diameter suction tip relative to the guide catheter, and the step down diameter of the second tubular section of the embodiment of FIGS. 15 and 16 allow for further reach into narrow neurovascular vessels. The effective suction lumen then extends through the guide catheter into the connecting section of the suction extension and then into the tubular extension, which can have further step downs in diameter. The inner diameter of the connecting section may or may not be the same as the inner diameter of the first tubular section. The narrow diameter of the tubular extension provides for reach into small circuitous blood vessels and the use of the larger diameter proximal suction lumen improves the suction performance significantly without detracting from the ability to reach appropriate locations.

FIG. 16A shows an alternative embodiment of the suction extension in which the control structure has a handle at or near its proximal end. Referring to FIG. 16A, control structure/wire 340 has a handle 342 secured near its proximal end. Handle 342 may or may not comprises structure to provide for disengagement of the handle. A specific embodiment of a handle is described in detail below. Control structure/wire 340 has a twist 344 at its distal end to inhibit the removal of handle 342 from control structure 340. Twist 344 can refer to or be replaced with a bend, a knot, an anchor, or other structure or distortion that prevents or inhibits the removal of handle 342 from control structure 340.

To further provide for suction strength, the tubular extension itself can have different sections with stepped down diameters, such as shown in the embodiment of FIGS. 15 and 16. In general, the arteries progressively decrease in diameter so a section with a somewhat larger diameter may be desirable consistent with the reach of the suction tip into a selected narrow vessel. With respect to first tubular section, this section generally has an approximately constant diameter (generally inner diameter or outer diameter with an assumption of approximately constant wall thickness) that is generally from about 0.95D to about [d+0.1(D−d)], in further embodiments from about 0.925D to about [d+0.25(D−d)], and in some embodiments from about 0.9D to about [d+0.35(D−d)], where d is the diameter of second tubular section and D is the average diameter of the connecting section. The length of first tubular section can be from about 10% to about 90%, in further embodiments from about 20% to about 80% and in additional embodiments form about 30% to about 70% of the total length of tubular extension, e.g., the total length of first tubular section, second tubular section, and the optional transition section or just a single tubular section for corresponding embodiments ($L_T$ in FIG. 6). The connecting section can have a length ($L_C$ in FIG. 6) from about 4 mm to about 8 cm and in further embodiments from about 5 mm to about 6 cm. A person of ordinary skill in the art will recognize that additional ranges of dimensions and relative dimensions within the explicit ranges above are contemplated and are within the present disclosure. While FIGS. 15 and 16 show a tubular extension with one step down in diameter to a second tubular section, in other embodiments there can be additional constant diameter tubular sections further stepping down the diameter, which further divide the length of the entire tubular extension specified above. For example, there can be a further intermediate tubular section, two further intermediate tubular sections or more than two further intermediate tubular sections.

The tubular extension or distal tubular section of the tubular extension for embodiments with a plurality of tubular sections with different inner diameters can have an inner diameter from about 20 percent to about 90 percent of the inner diameter of the engagement section of the guide catheter, and in further embodiments from about 30 percent to about 85 percent and in additional embodiments from about 35 percent to about 80 percent of the inner diameter of the engagement section of the tubular shaft. For example, the distal tip of the tubular extension can have an inner diameter in a range from about 0.5 mm to about 1.9 mm, in further embodiments from about 0.6 mm to about 1.8 mm, and in other embodiments from about 0.65 mm to about 1.75 mm. The tubular extension can have a length from about 3 cm to about 60 cm, in some embodiments from about 5 cm to about 55 cm and in further embodiments from about 8 cm to about 50 cm. A person of ordinary skill in the art will recognize that additional ranges of dimensions within the explicit ranges above are contemplated and are within the present disclosure.

Figure 18:
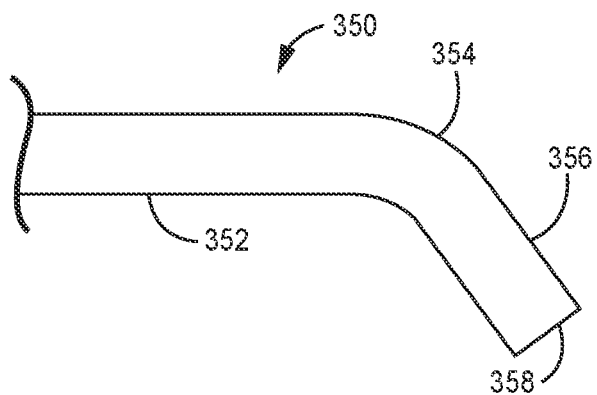
FIG. 18 is a fragmentary side view of a suction tip with a bend.
Figure 19:
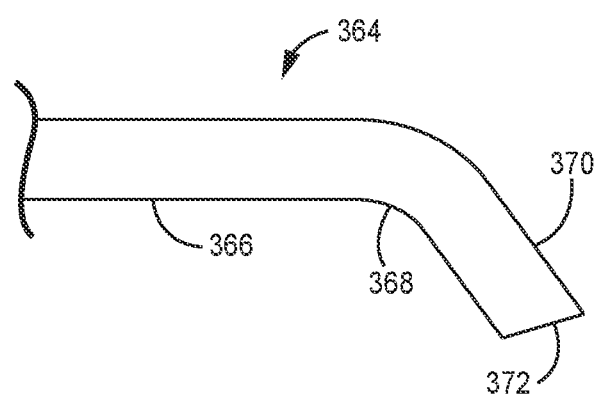
FIG. 19 is a fragmentary side view of a suction tip with a bend and an angled opening.

The distal tip of the tubular extension can be bent or curved in its natural unstressed configuration. It has been found generally that a bent tip catheter can facilitate tracking of the catheter over a guidewire without adversely altering the suction abilities. See, for example, U.S. Pat. No. 8,021,351 to Boldenow et al., entitled "Tracking Aspiration Catheter," incorporated herein by reference. Two general versions of a bent suction tip are shown in FIGS. 18 and 19. Referring to FIG. 18, suction tip 350 comprises a straight section 352, bend 354 and bent tip section 356 with a flat distal opening 358 approximately perpendicular to the axis of bent tip section 356. Referring to FIG. 19, suction tip 364 comprises a straight section 366, bend 368 and bent tip section 370 with an angled distal opening 372 at a nonperpendicular angle to the axis of bent tip section 370. Bent tip sections 356, 370 are generally cylindrical and can have approximately the same diameters as corresponding straight sections 352, 366. While two shapes of openings are shown in FIGS. 18 and 19, any reasonable shape of the opening generally can be used.

Figure 20:
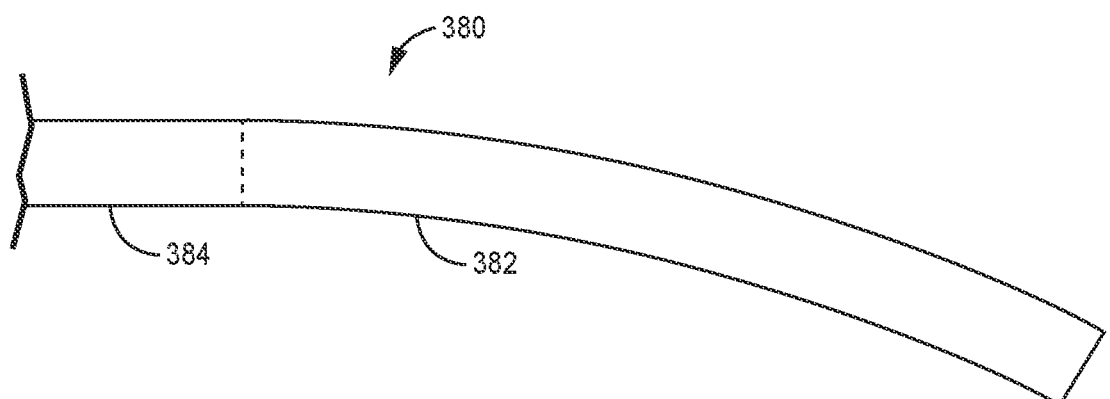
FIG. 20 is a fragmentary side view of a suction tip with a gentle curve.

A specific embodiment of a bent tip for a suction extension 380 is shown in FIG. 20. In this embodiment, the distal tip 382 is curved with no straight section at the distal end in this embodiment, although alternative embodiments can have short straight segment at the distal end. Distal tip 382 extends from a straight section 384 of suction extension 380. The arc of the curve is approximately circular, but other gentle arcs can be used, in which case the radius of curvature can be an average over the arc.

In this embodiment, the curvature of the tip is gradual so that the distal tip may not have a straight section. An angle γ can be defined based on the point of initial curvature and the natural position of the tip taken at the middle of the distal opening. In some embodiments, angle γ can be from about 5 degrees to about 21 degrees and in further embodiment from about 7 degrees to about 20 degrees. To achieve the gentle curvature, the radius of curvature generally is relatively large, and in some embodiments, the radius of curvature can be from about 21 mm to about 100 mm and in further embodiments from about 25 mm to about 75 mm. In some embodiments, a straight portion of the tip after the curve can have a length no more than about 1 cm, and in other embodiments from about 0.1 mm to about 6 mm and in further embodiments from about 0.5 mm to about 4 mm. In alternative embodiments, the curve consists of a gradual arc with no significant straight section distal to it, such that the curve or bend is specified by the angle and radius of curvature. A person of ordinary skill in the art will recognize that additional ranges of angles, radii and lengths within the explicit ranges above are contemplated and are within the present disclosure.

As noted above, the connecting section of the suction extension can have a non-circular, oval cross section, which can interface then with the inner surface in the lumen of the guide catheter to contact the inner surface at two locations along the circumference. The interface between the connecting section of the suction extension and the engagement section of the guide catheter reduces or eliminates any flow between surfaces so that essentially all of the suction flow passes through the lumen of the suction extension. At the same time, the suction extension can be positioned longitudinally within the engagement section to position the suction extension by a user through sliding the control structure. These various conditions can be balanced effectively to provide the desired functionality.

Referring to FIG. 21, a sectional view is shown of a connecting section 400 of a suction extension within an engagement portion 402 of a guide catheter. The non-cylindrical nature of the cross section of connecting section 400 is readily visible. Due to the interface between the elements, the oval shape of connecting section 400 can be distorted relative to its shape separated from the guide catheter, especially if the undistorted length of the major axis of the connecting section 400 is greater than the inner diameter of engagement portion 402. Connecting section 400 can contact the inner surface of the lumen of engagement section 402 at two contact locations 404, 406. The size of contact locations 404, 406 generally depends on the dimensions of the elements, the shape of connecting section 400 and the material properties. It is generally not necessary to precisely define the boundaries of the contact locations.

As noted above, the non-cylindrical connecting section can be characterized with the major axis, minor axis and an average diameter obtained from the circumference. Based on these parameters, it is possible to specify significant aspects of the interface between connecting section 400 and engagement portion 402 with a difference between the major axis and the minor axis, with a difference between the major axis of an unconstrained connecting section 400 and the inner diameter of engagement section 402, and with the difference between the inner diameter of engagement section 402 and the average diameter of connecting section 400. For example, the difference between the major axis and the minor axis can be from about 30 microns to about 160 microns and in further embodiments from about 50 microns to about 140 microns. In some embodiments, the tolerance measured as a difference between the diameter of the inner surface of engagement section 402 and the average diameter of the connecting section can be, for example, no more than about 4 thou (1 thou=1/1000 of an inch; 4 thou~102.6 microns), in further embodiments no more than about 3 thou (76.2 microns), in additional embodiments no more than about 1.75 thou (45 microns), in other embodiments from about 1 thou (25.4 microns) to about 1.75 thou (45 microns) and can be approximately zero within the measurement uncertainty. For embodiments in which the major axis of the connecting section separated from the guide catheter is larger than the guide catheter inner diameter, the difference between the major axis of unconstrained (i.e., separated from the guide catheter) connecting section 400 and the inner diameter of engagement section 402 can be from about 0 to about 250 microns, in further embodiments from about 15 microns to about 150 microns and in other embodiments from about 20 microns to about 100 microns. A person of ordinary skill in the art will recognize that additional ranges of dimensions differences within the explicit ranges above are contemplated and are within the present disclosure.

Catheter components can be formed from one or more biocompatible materials, including, for example, metals, such as stainless steel or alloys, e.g., Nitinol®, or polymers such as polyether-amide block co-polymer (PEBAX®), nylon (polyamides), polyolefins, polytetrafluoroethylene, polyesters, polyurethanes, polycarbonates, polysiloxanes (silicones), polycarbonate urethanes (e.g., ChronoFlex AR®), mixtures thereof, combinations thereof, or other suitable biocompatible polymers. Radio-opacity can be achieved with the addition of metal markers, such as platinum-iridium alloy, tantalum, tungsten, gold, platinum-tungsten alloy or mixtures thereof, such as wire or bands, or through radio-pacifiers, such as barium sulfate, bismuth trioxide, bismuth subcarbonate, powdered tungsten, powdered tantalum or the like, added to the polymer resin. Medical grade PEBAX is available commercially loaded with barium sulfate, as well as with ranges of Shore hardness values. Generally, different sections of aspiration catheter can be formed from different materials from other sections, and sections of aspiration catheter can comprise a plurality of materials at different locations and/or at a particular location. In addition, selected sections of the catheter can be formed with materials to introduce desired stiffness/flexibility for the particular section of the catheter. Similarly, fitting components can be formed form a suitable material, such as one or more metals and/or one or more polymers.

In some embodiments, the guide catheter, suction extension or appropriate portions thereof comprises a thermoplastic polymer, such as the polymers listed above, with embedded metal elements, which reinforces the polymer. The wire can be braided, coiled or otherwise placed over a polymer tubing liner with some tension to keep the wire in place over the tubing liner. In some embodiments, a polymer jacket, such as a heat shrink polymer, can then be placed over the top and heated to shrink and fuse the cover over the structure, and/or the polymer tube can be softened with heat to allow incorporation of the metal reinforcements. Upon heating to a temperature over the softening temperature and/or heat shrink temperature of the polymer and subsequent cooling, the reinforcing metal becomes embedded within the polymer. In appropriate embodiments, a liner and a jacket can be the same or different materials. Suitable wire includes, for example, flat stainless steel wire or the like. Wire diameters can range from about 0.00025 inch (0.00635 mm) to about 0.004 inch (0.1 mm) and in further embodiments from about 0.0005 inch (0.013 mm) to about 0.003 inch (0.075 mm). For appropriate embodiments, braid picks per inch can be from about 20 to about 250 picks per inch and in further embodiments from about 50 to about 150 picks per inch. For appropriate embodiments, coils can be single or multiple filament coils having, for example, pitches from about 0.005 inch (0.13 mm) to about 0.1 inch (2.54 mm) and in further embodiments form about 0.01 inch (0.26 mm) to about 0.050 inch (1.27 mm). A person of ordinary skill in the art will recognize that additional ranges within the explicit ranges below are conceived and are within the present disclosure. The wire adds additional mechanical strength while maintaining appropriate amounts of flexibility. The wire can provide some radio-opacity although radiopaque bands generally would provide a darker and distinguishable image relative to the wire. However, the image of the wire can provide further visualization of the catheter during the procedure.

To decrease the chance of accidental removal of the radiopaque band from the catheter and to decrease the chance of the radiopaque band catching onto other objects within the vessel, a metal reinforcing wire can be used to cover or enclose the radiopaque band with the metal wire subsequently being embedded within the polymer. In some embodiments, a polymer jacket can be placed over the metal wire, which is correspondingly covering the radiopaque band(s), and the heat bonding embeds the radiopaque marked band also. If desired, placement of the marker band under metal wire can prevent the band from being separated from the catheter in the event that the wall is kinked or collapsed. If collapse or kinking of the catheter wall occurs, the braid-wire over the surface of the band collapses down over the marker band to prevent it from separating from the structure.

Referring to FIG. 22, an example of a procedure for forming a section of reinforced catheter is shown. Polymer liner 420 is placed over mandrel 422. In the second sequential figure, metal braiding 424 has been placed over the polymer liner, and commercial braiding equipment can be used for this step. As shown in the third figure of the series, a metal coil 426 is placed over braided wire 424 and a polymer cover 428 is placed over the coil 426. A heat source 430 can be used to heat shrink polymer cover 428 to complete the reinforced catheter section 432, as shown in the fourth sequential figure of FIG. 22. Of course, in some embodiments, only a coil or only metal braiding can be used, and the procedure is correspondingly revised. Similarly and independently, a heat shrink cover may or may not be used, and again the procedure is correspondingly revised.

Treatment Systems

The suction system described herein can be used effectively to remove blood clots from the vasculature, including the vasculature of the brain to treat acute stroke conditions. In particular, the narrow tip catheter of the '792 patent have performed well in human clinical trials to restore blood flow in persons with an acute embolic stroke with good patient outcomes. The device described herein may be expected to provide even better suction while maintaining access capability into vessels challenging to navigate. Nevertheless, for some acute stoke conditions or other embolic events, it can be desirable to use the suction catheter systems described herein with other medical tools for performing the therapy. Furthermore, specific desirable embodiments of proximal fittings are described in this section that provide for improved procedures for use of the suction extension described herein. In particular, adaptations of the proximal fittings provide for removal of a tubular extension of the suction extension from the guide catheter without passage through a hemostatic valve. In some embodiments, the proximal fittings can further comprise an additional branched fitting with a proximal end that can dock the proximal end of the suction extension to provide for convenient removal from the isolated locations behind a hemostatic valve to provide for convenient clearing of thrombus blockage of the suction extension and reinsertion. The thrombus blockage can be cleared through a flush delivered from a branch of docking Y-connector with the suction extension docked for quick replacement of the suction extension for the additional removal of further blockage form the blood vessel in the patient. Also, the proximal fittings can be adapted with a pressure sensor that can provide valuable information about the status of the suction process. The availability of the pressure information can be used to improve aspects of the procedure to increase efficacy and to reduce potential risks to the patient.

Figure 23:
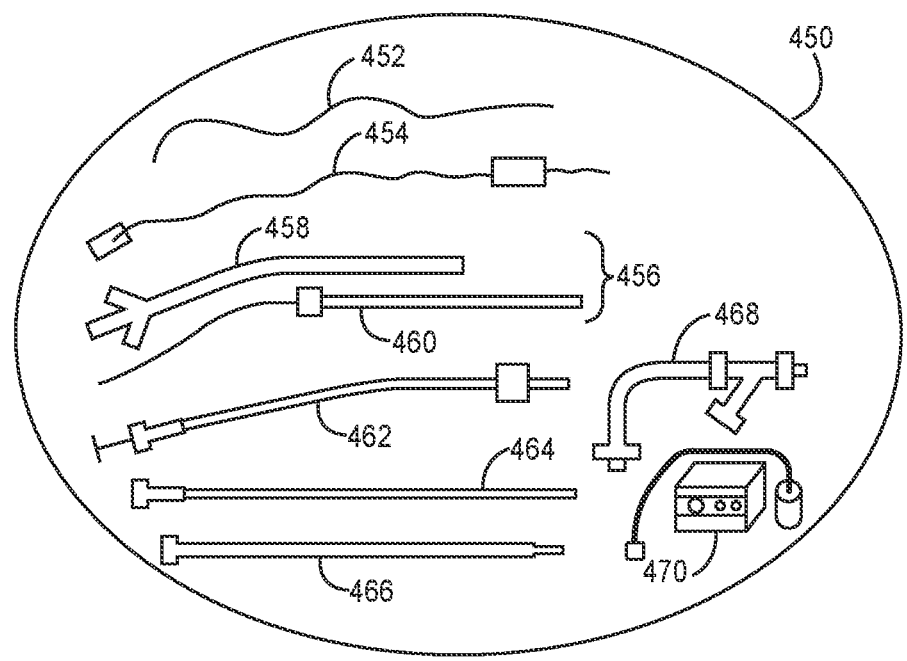
FIG. 23 is a schematic depiction of a collection of medical devices that can be used together or in selected sub-combinations for selected percutaneous procedures in bodily vessels including a suction system as described herein.

Referring to FIG. 23, a treatment system 450 is shown comprising a guidewire 452, embolic protection system 454, suction catheter system 456, shown with guide catheter 458 and suction extension 460 separated, a percutaneous medical device 462, a microcatheter 464, a delivery catheter 466, proximal fittings 468, and negative pressure device, e.g., pump or syringe, or the like, 470. Suitable components of proximal fittings 468 are described below. Not all embodiments of medical systems may have all of these components, and some medical system embodiments may have multiple components of each type, such as multiple distinct percutaneous medical devices. Suitable structures covering desirable embodiments for proximal fittings 468 are discussed in the following section.

Guidewires suitable for use in tortuous bodily vessels are described in published U.S. Pat. No. 10,518,066 to Pokorney et al., entitled "Medical Guidewires for Tortuous Vessels," incorporated herein by reference. In some embodiments, embolic protection system 454 can comprise a guide structure to provide for delivery of the device, and for these systems a separate guidewire may or may not be used. Suction catheter systems 456 are described in detail herein, and the various embodiments described herein can be adapted for use with the medical systems as well as for use as stand-alone devices. If desired for particularly challenging device delivery, the medical system can include a delivery catheter 466, as described in the '938 application.

Embolic protection devices with small filter longitudinal extent and designed for suitable manipulations to facilitate delivery in vessels have been developed that are suitable for use in the medical systems described herein. See, for example, U.S. Pat. No. 7,879,062B2 to Galdonik et al., entitled "Fiber Based Embolic Protection Device," and U.S. Pat. No. 8,092,483B2 to Galdonik et al., entitled "Steerable Device Having a Corewire Within a Tube and Combination with a Medical Device," both of which are incorporated herein by reference. Additional fiber-based filter devices particularly designed for delivery into tortuous vessels are described in U.S. Pat. No. 8,814,892B2 to Galdonik et al. (hereinafter the '892 patent), entitled "Embolectomy Devices and Method of Treatment of Acute Ischemic Stroke Condition," incorporated herein by reference. The '892 patent describes the use of the filter device as a clot engagement tool for use with an aspiration catheter. The '892 patent also envisions the use of supplementary structures to facilitate engagement of the clot. The DAISe™ clot removal system with a fiber based filter is under development by MIVI Nueroscience, Inc. The use of supplementary structures are also contemplated in procedures described herein.

Microcatheters have been designed to allow for access to small blood vessels, such as cerebral blood vessels, and cerebral microcatheters are available commercially, e.g. Prowler Select™ (Cordis Neurovascular Inc.) and Spinnaker Elite™ (Boston Scientific Co.). Of course the term microcatheter can cover a range of devices, and the present discussion can focus on catheters useful for the procedures described herein. In some embodiments, microcatheters can comprise a distal section that is narrower than a proximal section. However, in further embodiments, a microcatheter can have an approximately constant diameter along its length to facilitate delivery of other devices over the microcatheter. A narrow distal diameter allows for the catheter to navigate the tortuous vessels of the brain. The distal section can be highly flexible enough to navigate the vessels, but resilient enough to resist kinking. A microcatheter comprises at least one lumen. The microcatheter can then be used to deliver other treatment devices, aspiration, therapeutic agents, or other means of treating a condition. While microcatheters can have a selected size, in some embodiments, the microcatheters can have a distal outer diameter from about 1.0 Fr to about 3.5 Fr and in further embodiments from about 1.5 Fr to about 3 Fr, and a length from about 30 cm to about 200 cm and in further embodiments from about 45 cm to about 150 cm. A person of ordinary skill in the art will recognize that additional size ranges within the explicit ranges above are contemplated and are within the present disclosure.

With respect to percutaneous medical devices 762, suitable devices include, for example, clot engagement devices, angioplasty balloons, stent delivery devices, atherectomy devices, such as stent retrievers, and the like. Desirable thrombus engagement devices are described in U.S. Pat. No. 10,463,386 to Ogle et al., entitled "Thrombectomy Devices and Treatment of Acute Ischemic Stroke With Thrombus Engagement," incorporated herein by reference. Stents may be, for example, balloon extendable, self-extendable or extendable using any other reasonable mechanism. Also, balloon extendable stents can be crimped to the balloon for delivery to engage a clot in a blood vessel. Some balloon-stent structures are described further, for example, in U.S. Pat. No. 6,106,530, entitled "Stent Delivery Device;" U.S. Pat. No. 6,364,894, entitled "Method of Making an Angioplasty Balloon Catheter;" and U.S. Pat. No. 6,156,005, entitled "Ballon [sic] Catheter For Stent Implantation," each of which are incorporated herein by reference. Self-expanding stents are described further in U.S. Pat. No. 8,764,813 to Jantzen et al., entitled "Gradually Self-Expanding Stent" and U.S. Pat. No. 8,419,786 to Cottone, Jr. et al., entitled "Self-Expanding Stent," both of which are incorporated herein by reference. Stent retrievers are described, for example, in U.S. Pat. No. 8,795,305 to Martin et al., entitled "Retrieval systems and methods of use thereof," incorporated herein by reference.

Once the clot treatment process is completed, it has been found that it is advantageous to at least partially remove the tubular extension of the suction extension from the guide catheter before removing the guide catheter from the patient. If a portion of the tubular extension is removed through a hemostatic valve during this removal process, the isolation between the vasculature and the exterior of the patient can be lost since the proximal end of the tubular extension is not designed for closure. The loss of isolation between the exterior of the patient and the interior of the catheter system can result in an undesirable amount of bleeding as well as complicating the control of trapped thrombus associated with the nozzle In some embodiments, the fitting designs described here are intended to address these issues through the inclusion of a tubular storage area distal to a hemostatic valve and connected for access to the proximal end of the tubular extension. Several suitable designs are described herein. The loss of blood from this withdrawal of the tubular extension can be reduced or eliminated through the use of the docking branched manifold described herein. As noted in the discussion below, the fitting structures can be assembled for commercial elements or can be designed as a specific fitting particularly for the suction system and/or treatment systems described herein.

During procedures with the aspiration system, the tubular extension of the suction extension may be removed from the patient to clear a clot prior to reinsertion and further removal of thrombus. Clearing of the clot from the tubular extension generally involves removal from the guide catheter and out from a hemostatic valve. After the tubular extension is cleared of blockage, it is reinserted through the hemostatic valve back into the patient. The clearing of the clot generally involves the back flow of fluid from the proximal to distal ends. The fittings described herein allow for the docking of the connection section of the suction extension against a docking element in a docking Y-fitting for removal through the hemostatic valve. Once removed through the hemostatic valve, flush fluid can be delivered from one branch of the Y-fitting to flush the tubular extension without the need to provide further connections to the suction extension. The other branch of the Y generally comprises a hemostatic valve or the like through which the control structure passes, and the closed valve allows for the direction of the flush fluid through the suction extension.

The first fitting elements have been previously described in published U.S. patent application 2019/0183517 to Ogle, entitled "Suction Catheter Systems for Applying Effective Aspiration in Remote Vessels, Especially Cerebral Arteries," incorporated herein by reference. The first fitting elements herein can be essentially the extent of the proximal fittings, but in the desirable embodiments herein, the proximal fittings further comprise a docking branched manifold. With the use of a docking branched manifold, the fittings can include further options for location of providing aspiration and/or delivery of perfusion liquids, ach as contrast dye or therapeutic compounds. Thus, while the earlier described proximal fittings can carry over to the first fitting element for engagement with a docking branched manifold, the first fitting elements can be designed, if desired, with less or different branching if certain functions are performed using the docking branched manifold. Thus, some of the embodiments described herein can be correspondingly simplified in some embodiments.

Figure 24A:
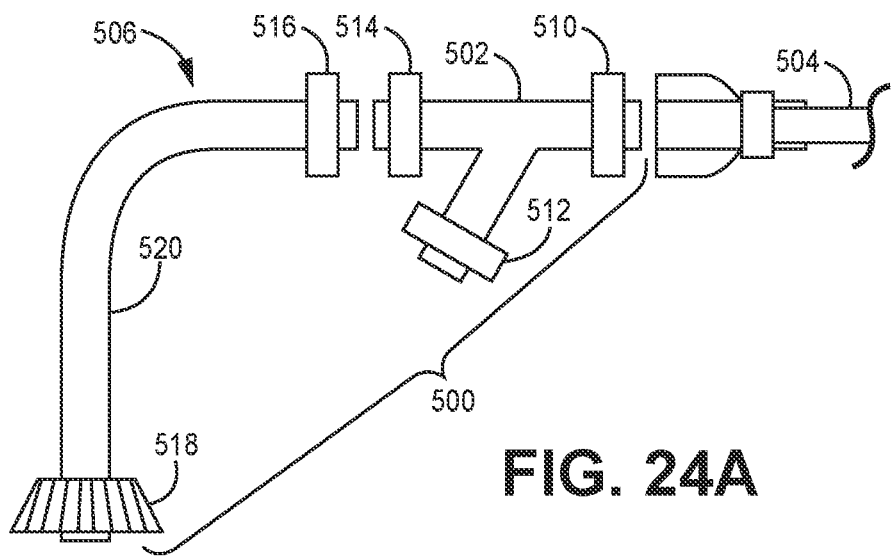
FIG. 24A is a fragmentary side view of proximal fittings shown with two separated components adjacent a guide catheter in which the two components are a Y-branch manifold and an extended hemostatic fitting.
Figure 24B:
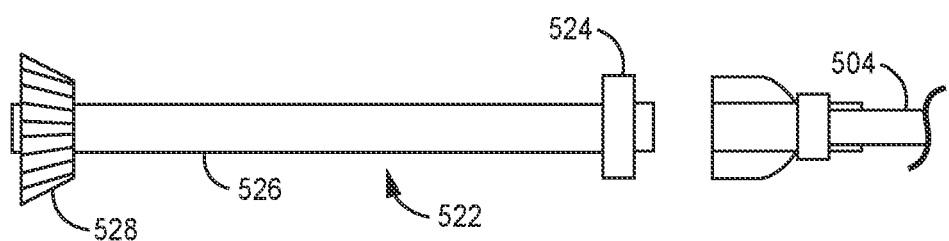
FIG. 24B is a fragmentary side view of a first alternative embodiment with a single non-branched component with a proximal hemostatic valve adjacent a guide catheter, which is suitable for use with a docking branched manifold.
Figure 25:
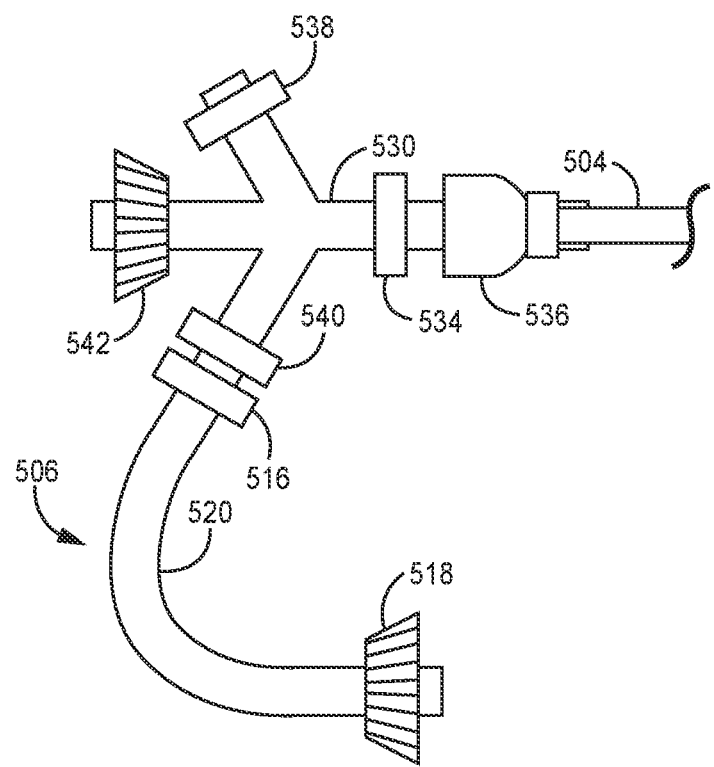
FIG. 25 is a fragmentary side view of another alternative embodiment of proximal fittings attached to a guide catheter with a three branch manifold extending from the guide catheter and an extended hemostatic fitting attached to one branch.
Figure 26:
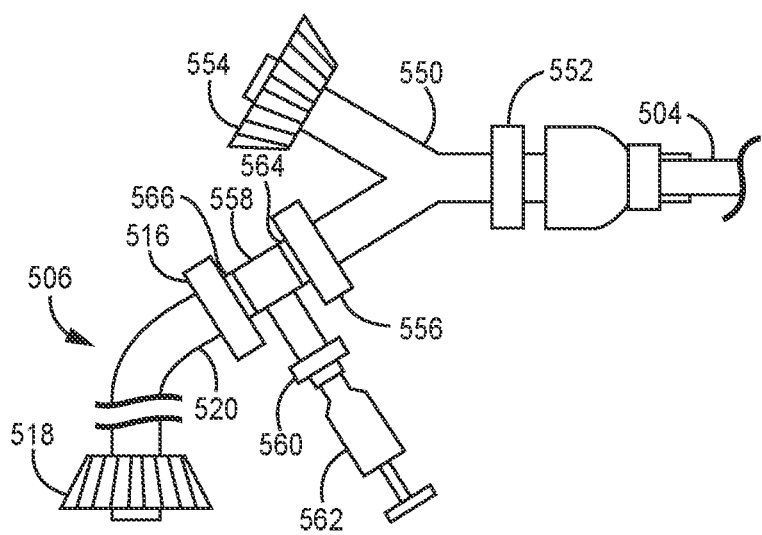
FIG. 26 is a fragmentary side view of a further alternative embodiment of proximal fittings extending from a guide catheter in which the fittings comprise a Y-branch manifold, a T-branch manifold connected to one branch of the Y and an extended hemostatic fitting extending from the straight branch of the T-branch and a negative pressure device attached along the T-branched conduit.

Three representative embodiments for the first fitting element of the proximal fittings providing withdrawal of the suction extension within hemostatic confinement are presented in FIGS. 24-26 in which the devices provide for holding a tubular extension of the suction extension within the manifold sealed behind a hemostatic valve or valves. As shown in FIGS. 24A-26, the proximal fittings are assembled from a plurality of fitting components, and these fittings are designed to allow for aspiration from these first fitting elements. But if desired, one or more of the components can be manufactured as a unitary structure with the corresponding elimination of one or more sets of connectors, and particular configurations can involve various tradeoffs, such as convenience of use, cost, packaging, standards in the art, flexibility of design during use, or the like. As shown in FIGS. 24A and 24B, the components are shown spaced apart, while for contrast, the multiple components are shown connected in FIGS. 25 and 26. Of course, for specific applications, additional components of the overall manifold can be assembled into the ultimate proximal fitting structure. For example, embodiments are shown below providing for attachment of a pressure sensor. Also, as shown below, additional components of the manifold can provide for docking and withdrawal of the suction extension in association with a fitting to provide for clearing of a blockage in the suction extension.

Referring to FIG. 24A, fittings 500 comprises Y-branch manifold 502 suitable for connection with guide catheter 504, and extended hemostatic fitting 506. Guide catheter 504 can be any of the embodiments of guide catheters described above. Y-branch manifold 502 provides for multiple connectors with fluid communication with guide catheter 504. As shown in FIG. 24A, Y-branch manifold 502 comprises three connectors 510, 512, 514, which can be Tuohy-Borst connectors, Luer connectors or other suitable connector. Connector 510 can be selected for connection with guide catheter 504. Connector 512 can be connected to a negative pressure source, such as a pump, or to further branched manifolds to provide for various connections such as for an infusion fluid source, generally with at least one connection to a negative pressure device. Connector 514 is configured to connect with extended hemostatic fitting 506. Extended hemostatic fitting 506 comprises connector 516 for a mated connection with Y-branch manifold 502, hemostatic valve 518 and tubular portion 520 between connector 516 and hemostatic valve fitting 518. Tubular portion 520 can have in some embodiments a suitable length for removing a tubular extension of a suction extension out from guide catheter 504 without passing any portion of the tubular extension or connecting section through the hemostatic valve, although a proximal control structure generally passes through the hemostatic valve, which is the possible configuration through the procedure. FIG. 24B depicts an alternative embodiment of first fitting element without a branch, which is suitable for use with a docking branched manifold configured to deliver aspiration. Unbranched first fitting element 522 comprises connector 524, unbranched tubular element 526 and hemostatic valve 528.

The length of tubular portion 520 can be selected according to the length of the tubular extension as well as potentially if desired a relevant length of Y-branch manifold 502, which collectively can be referred to as a tubular section for placement of the tubular extension with the connecting section in hemostatic isolation outside of the guide catheter. It may or may not be desirable to withdraw the tubular extension fully into tubular portion 520 such that the remaining portions of the manifold are open. With respect to unbranched tubular element 526 of FIG. 24B, this element may or may not have a suitable length for the withdrawal of the tubular extension to be fully isolated within the unbranched tubular element 526. For the range of alternative embodiments considered for the first fitting elements of the proximal fittings of FIGS. 24A and 24B, the dimensions of the tubular section can be appropriately identified in the particular structure. In general, tubular portion 520 of extended hemostatic fitting 506 can have a length from about 8 cm to about 55 cm, in further embodiments from about 9 cm to about 50 cm, and in other embodiments from about 10 cm to about 45 cm. A person of ordinary skill in the art will recognize that additional ranges of lengths within the explicit ranges above are contemplated and are within the present disclosure.

In alternative or additional embodiments, extended hemostatic fitting 506 can comprise a tubular element with two connectors on either end and a separate hemostatic valve with a Luer or other connector on the opposite end that connect to each other to effectively form an equivalent structure to that shown in FIG. 24. Similarly, one or more additional fitting components can be connected using suitable connectors between extended hemostatic fitting 506 and Y-branch manifold 502, such as additional branched elements, and similarly additional fitting components can be connected at connector 512 to provide additional features to the fittings, such as connection of a pressure sensor or other structures. Thus, while providing the ability to withdraw a tubular extension within the closed fittings, the proximal fittings can be adapted with suitable structure to provide desired functionality. While this discussion has focused on the assembly of multiple fitting components to provide an overall fitting structure, one or more of these components can be formed as integral parts of a corresponding unitary structure, such as the integration of Y-branch manifold 502 and extended hemostatic fitting 506 into a unitary structure through the replacement of connectors 514 and 516 with a unitary section of tubing, and similar integration can be performed for adding additional structure. The unitary structure incorporating the features of Y-branch manifold 502 and extended hemostatic fitting 506 comprises a branched manifold with an extended hemostatic valve portion, which can be a suitable alternative to the structure in FIG. 24. Thus, various combinations of connecting elements, redesigning unitary components, and the like can be implemented to form a desired proximal fittings design.

Referring to an alternative configuration of a first fitting element in FIG. 25, a three-branch manifold 530 is connected to guide catheter 504 and extended hemostatic fitting 520 is connected to a connector of one branch of three-branch manifold 530. Three-branch manifold 530 comprises first connector 534 connected to a proximal connector 536 of guide catheter 504, first branch connector 538, second branch connector 540 and hemostatic valve 542. Second branch connector 540 is connected to the extended hemostatic fitting 506, which is described in detail in the context of FIG. 24. First branch connector 536 can be connected to a negative pressure source directly or through a further branched manifold. Hemostatic valve 542 can be used for the introduction of supplemental treatment structures or other desirable devices. Again, the structure shown in FIG. 25 can be further divided into additional components if desired. For example, the three branch manifold can be effectively formed using two sequential Y-branch connectors. Again, additional fitting components can be connected onto the proximal fitting structure in FIG. 25 to provide additional features as described above in the context of FIG.

24. Also similarly, one or more separate components of the proximal fittings can be constructed as a unitary structure. Thus, component accretion and/or combination/joining processes can be combined for designing of a desired proximal fittings configuration.

Referring to FIG. 26, a further embodiment of a first fitting element of the proximal fittings is shown with a symmetric Y-branch structure. As shown in FIG. 26, symmetric Y-branch manifold 550 comprises first connector 552 connected to guide catheter 504, branched hemostatic valve 554 and branched connector 556. Branched connector 556 is connected with T-branch fitting 558. T-branch fitting 558 has a T-connector 560 that is shown connected with negative pressure device 562, such as a syringe or a pump. T-branch connector 556 is further connected with extended hemostatic fitting 506, which is described in detail in the context of FIG. 24 including but not limited to the dimensions of the element. T-branch connector 556 comprises connectors 564, 566 for respective connection with mated connectors 556, 516. The structure shown in FIG. 26 can be formed with multiple components used to form the structure, such as a separate component with hemostatic valve 554 connected with a suitable connector to a mated connector on symmetric Y-branch manifold 550, which is correspondingly modified. Again, additional fitting components can be connected onto the proximal fitting structure in FIG. 26 to provide additional features as described above in the context of FIG. 24. Also similarly, one or more separate components of the proximal fittings can be constructed as a unitary structure. Thus, component accretion and/or combination/joining processes can be combined for designing of a desired proximal fittings configuration.

The proximal fittings including its various potential components can be formed from suitable materials for sterile assembly, which can involve in some embodiments subjecting the components to radiation. The components can be formed in either rigid and/or flexible materials such as polymers provided herein, and the connectors can be formed from suitable combination of materials for the formation of seals, such as elastomers. Rigid components can be formed, for example, from polycarbonate or other suitable polymer. The tubular portion 520 of extended hemostatic fitting 506 can be formed from a more flexible polymer, such as one or more of the polymers described above for the catheter body, for example, polyether-amide block co-polymer (PEBAX®), nylon (polyamides), polyolefins, polytetrafluoroethylene, polyesters, polyurethanes, polycarbonates, polysiloxanes (silicones), polycarbonate urethanes (e.g., ChronoFlex AR®), mixtures thereof, combinations thereof, or other suitable biocompatible polymers. As noted above, the various fitting structures can be assembled from additional components, added onto or subdividing the various components of the embodiments, and/or the components can be formed as integral structures correspondingly molded. Thus, particular designs can be assembled from existing commercially available components or all or a portion of the fittings can be produced specifically for these applications.

The proximal fittings can also be equipped with a pressure sensor to help guide the procedure. If a pump is used to supply negative pressure, the pressure set on the pump establishes a differential pressure limit. If fluid freely flows to the pump, the differential pressure in the conduits leading to the pump can be relatively low. If flow is effectively completely blocked, the gauge pressure in the line can be approximately the pump pressure, which is negative indicating suction. Intermediate pressure levels may be indicative of restrictions of flow due to normal catheter or suction extension configurations that can cause some flow resistance, or of less severe blockages to the flow from various potential sources. In any case, as explained further below, having a measure of the line pressure in the proximal fittings can provide valuable information to assist in the procedure.

Figure 27:
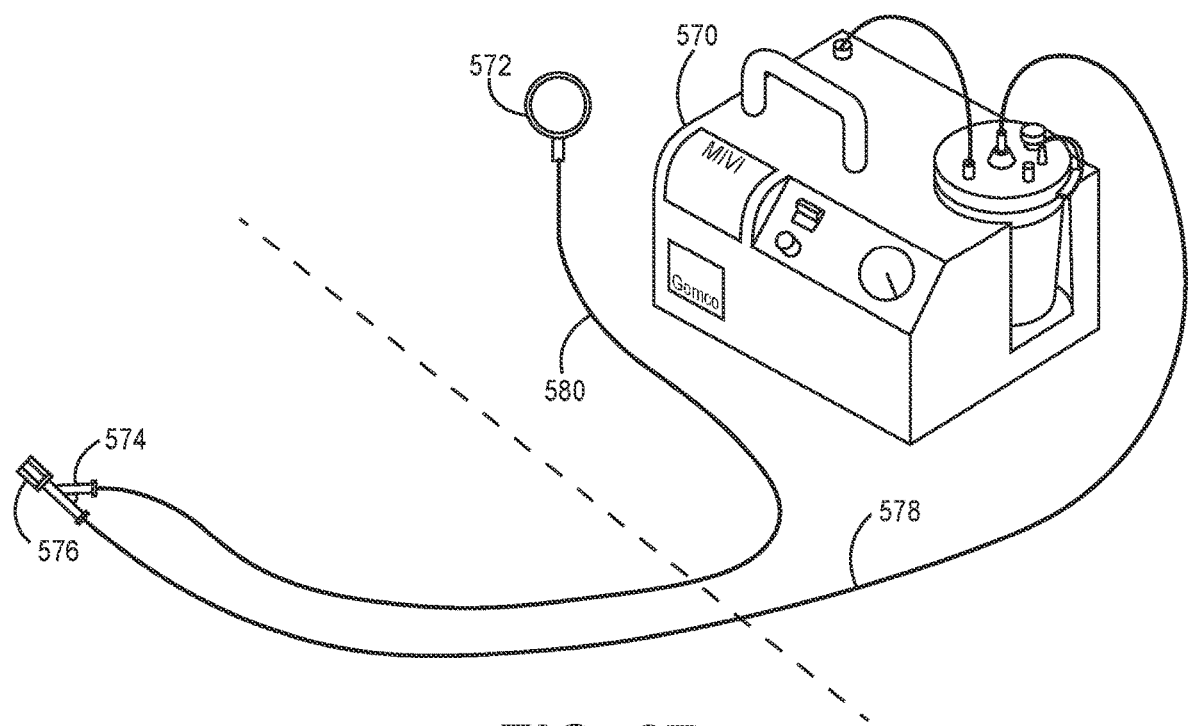
FIG. 27 is a perspective view of a Y-branch manifold adapted for connection with a pump and to a pressure sensor.
Figure 28:
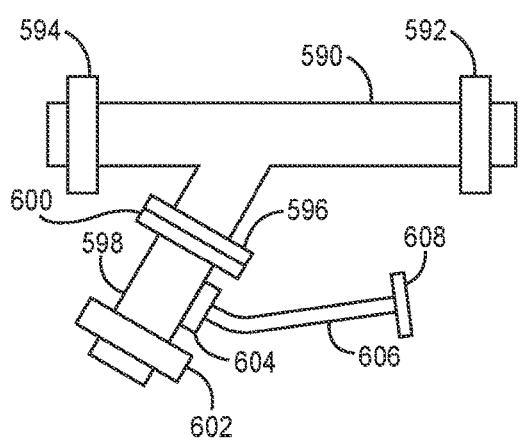
FIG. 28 is a side view of a Y-branch manifold attached to a tubular fitting adapted with a pressure sensor having an electronic connector.
Figure 29:
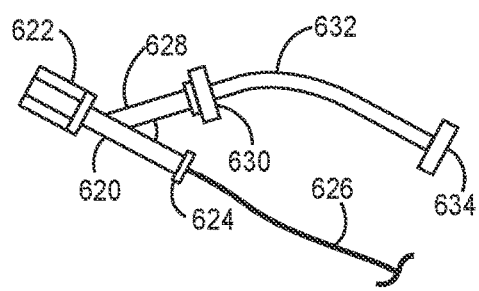
FIG. 29 is a side view of a Y-branch manifold with a terminal pressure sensor along one branch and with an electrical connector for connection with the pressure sensor.

There are various possible configurations for a pressure sensor in association with the proximal fittings, and three representative embodiments are shown in FIGS. 27-29. Referring to FIG. 27, a pump 570 and pressure gauge 572 are connected to a Y-manifold 574 that comprises a connector 576 that can be attached to manifold connectors in the fittings connected to the guide catheter, such as shown in FIGS. 5 and 24-26. Pump 570 and pressure gauge 572 can be connected, respectively, using tubing 578, 580 to Y-manifold 574. The connections of tubing 578, 580 to Y-manifold 574 can be achieved at suitable connectors or they can be formed integral to the component. In this embodiment, pump 570 and optionally pressure gauge 572 may not be sterile, but no flow is intended to go to the patient from these devices. If the non-sterile components are appropriately isolated from the patient's fluids, the configuration can be acceptable even though the devices are not sterile. A selected length, for example 6 feet, dividing line to provide for appropriate sterile isolation is schematically denoted in FIG. 27 with a dashed line noted with an arrow. Commercial aspiration pumps for medical applications, in which some specific pumps are noted above, can operate at gauge pressures from about −1 to about −26 inches of mercury (−25 mmHg to −660 mmHg). High pressure tubing is also available for medical applications, e.g., from MIVI Neuroscience, Inc. or Penumbra, Inc.

A further embodiment of a fitting adapted with a pressure sensor is shown in FIG. 28. The fitting component in FIG. 28 comprises a Y-branch connector 590 with a distal connector 592, a proximal connector 594 and branch connector 596, and a pressure sensor component 598 with a first connector 600 shown connected with branch connector 590 and second connector 602. Pressure sensor component 598 further comprises pressure sensor 604 installed on the side wall of pressure sensor component 598. Electrical wires 606 extend from pressure sensor 604 and terminate at electrical connector 608, which can be a multi-pin clip or other suitable connector configuration. Electrical connector 608 can be suitable for connection to a suitable monitor or display. Commercial pressure sensor components for use as pressure sensor component 598 are commercially available, for example, from PendoTECH, Princeton, N.J., USA. These components can be purchased sterile or they can be sterilized before use using conventional methods, such as using gamma irradiation. A pump or other negative pressure device can be connected to second connector 602 or other appropriate portion of the finally assembled proximal fittings, such as connectors associated with the docking branched manifold.

Another embodiment of a fitting component adapted with a pressure sensor is shown in FIG. 29. In this embodiment, Y-manifold 620 comprises a connector 622 for connection to other components of the proximal fittings and a connector 624 connected to tubing 626 for connection to a pump or the like. Y-manifold 620 further comprises a branch 628 adapted with a pressure sensor 630 at the end of the conduit. Pressure sensor 630 can be adapted on a connector cap or it can be bonded in a sealed configuration with branch 628, or otherwise adapted appropriately with a sealed attachment. Pressure sensor 630 is operably attached to electrical cable 632 which terminates at an electrical connector, such as a multi-pin clip. Pressure sensor dies or assemblies suitable for medical use are commercially available, such as from Merit Medical Systems, Inc. (Merit Sensors), which can be adapted for such connections.

As described above, the proximal fittings can comprise a docking branched manifold to facilitate the process for de-clogging the tubular extension, and two specific embodiments are discussed further to elaborate on some potential features, although as with the first fittings element, a range of component designs can be suitable. A first representative embodiment of a docking branched manifold is shown in FIG. 30. As shown in FIG. 30, the docking branched manifold is shown with a first fluid source, a second fluid source and an aspiration source. In alternative embodiments, only a first fluid source can be used, or only a first fluid sour and an aspiration source can be used. Similarly, only a first fluid source and a second fluid source can be used. In further embodiments, a third or more fluid sources can be introduced. Docking branched manifold 561 comprises tubular body 563, docking inlet tube 565, side port and channel 567, and a proximal hemostatic valve 569 along tubular body 563 proximal to side port and channel 567. Side port and channel 567 connects with valve 571, access manifold 573, first fluid source 575, second fluid source 577, and aspiration source 579. Fluid sources 575 and 577 can comprise a reservoir, a delivery system, such as a syringe, a pump, or the like, and may optionally include a valve. Suitable valves can include, for example, a stopcock, a flow control switch such as available from Merit Medical, various mechanical or powered valves, or the like. Aspiration source can comprise a pump or other negative pressure device along with appropriate pressure tubing, and can optionally further be associated with a separate valve.

A second representative embodiment of a docking branched manifold is depicted in FIGS. 31-34 of a docking branched manifold 601 that may be used to remove a suction extension, clear any thrombus or other matter associated with the suction extension, and return the suction extension into the patient for the collection of additional thrombus. FIG. 31A illustrates a side view of docking branched manifold 601. The docking branched manifold 601 comprises an input tubular segment 603 at a distal end. Proximal to input tubular segment 603 is a first branch 612 with connector 605. In embodiments, source valve 607 is connected to docking branch manifold 601 at connector 605. Source valve 607 has a second port 623. Source valve 607 may be a 2-way valve or it may be a multiple port valve. In some embodiments, source valve 607 is a stopcock, although other flow control elements can be used and may be desirable, such as some valves described above. Source valve 607 may be in fluid communication with a fluid source and configured such that opening source valve 607 permits fluid to flow into docking branched manifold 601 and closing source valve 607 blocks fluid from flowing into docking branched manifold 601. An example of a fluid source such as a positive pressure device, such as a pump or pressurized container, loaded syringe 609 or the like is depicted in FIG. 31B. A branch of docking branched manifold 601 generally comprises a hemostatic valve 611 to allow for passage of a control structure associated with the suction extension.

Docking branched manifold 201 generally comprises a tubular body 613 which can comprise a tapered connector 614 connecting with input tubular segment 603, although the precise configuration of the connecting section is generally not significant. In some embodiments, tubular body 613 of docking branched manifold 601 can comprise a distal section 616 comprised of a material selected for sealing within a hemostatic valve and a proximal section 618 comprising a different material from the distal section that may be molded to further comprise the Y-branch. A connector 625 can be used optionally to join distal section 616 and proximal section 618, and connector 625 can be made of a suitable material. Connector 625 may or may not be visible from the exterior and may or may not alter the external diameter, the internal diameter, or both diameters. If a suitable material is selected, tubular body 613 can be formed from a single material.

Figure 31A:
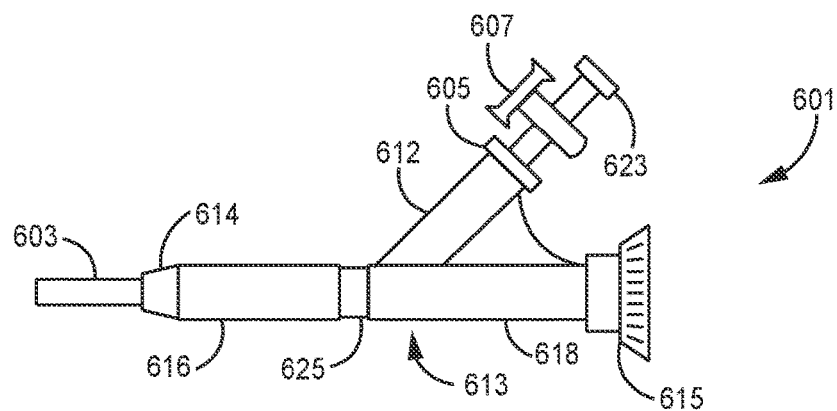
FIG. 31A is a side view of an alternative embodiment of a docking branched manifold with a docking element
Figure 31B:
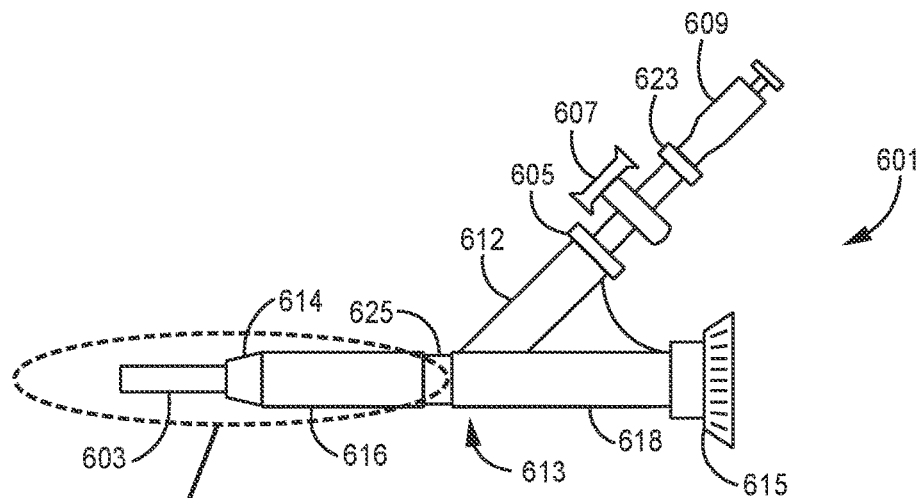
FIG. 31B is a side view of the docking branched manifold of FIG. 31A with a negative pressure device attached to one of the branches of the branched manifold.
Figure 31C:
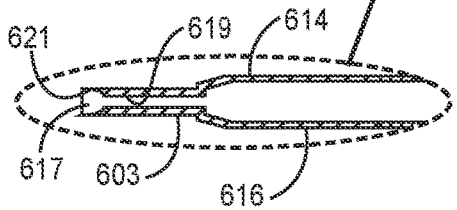
FIG. 31C is a fragmentary sectional view of the docking branched manifold of FIG. 31A showing the distal end with the docking element.

FIG. 31C depicts a fragmentary sectional view of docking branched manifold 601 showing a distal portion of input tubular segment 603 comprises a docking structure 617. Docking structure 617 may be configured to releasably retain a proximal end of a suction extension, such as any of the embodiments described above. For example, docking structure 617 may use an interference fit to secure the proximal end of a connection section of a suction extension. In embodiments, docking structure 617 can be configured with an internal tapering of the internal walls 619 of input tubular segment 603. For example, an interior surface 621 of input tubular segment 603 may taper inwards until an interior diameter of tubular input is less than an outer diameter of the distal end of the suction extension. In additional or alternative embodiments, docking structure 617 may have a flange on interior surface 621 of input tubular segment 603, which can be considered to be an infinitely sharp taper. In embodiments, docking structure 617 may also comprise a structure on an interior surface 621 of tubular input segment 603 configured to interface with a corresponding structure at the proximal end of the connection section of the suction extension. For example, docking structure 617 may include a detent on an interior surface 621 of tubular input segment 603 configured to interface with an indent on an exterior surface of tubular extension. In general though, the docking structure can be any suitable structure, such as a narrowing tubular structure, that provides for an, at least, approximately fluid tight fit of the proximal end of the connection section of the suction extension.

Figure 32:
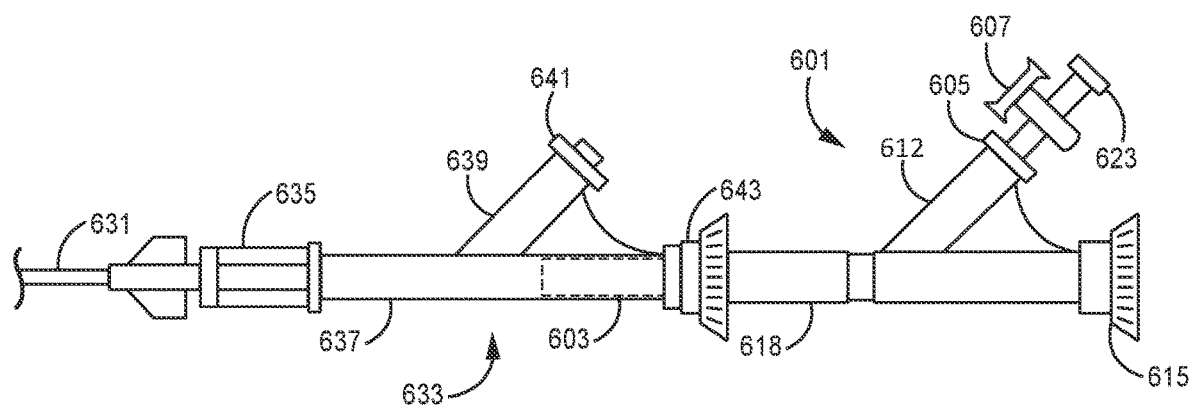
FIG. 32 is a side view of a guide catheter, a first fitting elements with a branched manifold that form part of the proximal fitting for the aspiration system, and a docking branched manifold, in which a hidden docking element is shown in dashed lines.
Figure 33:
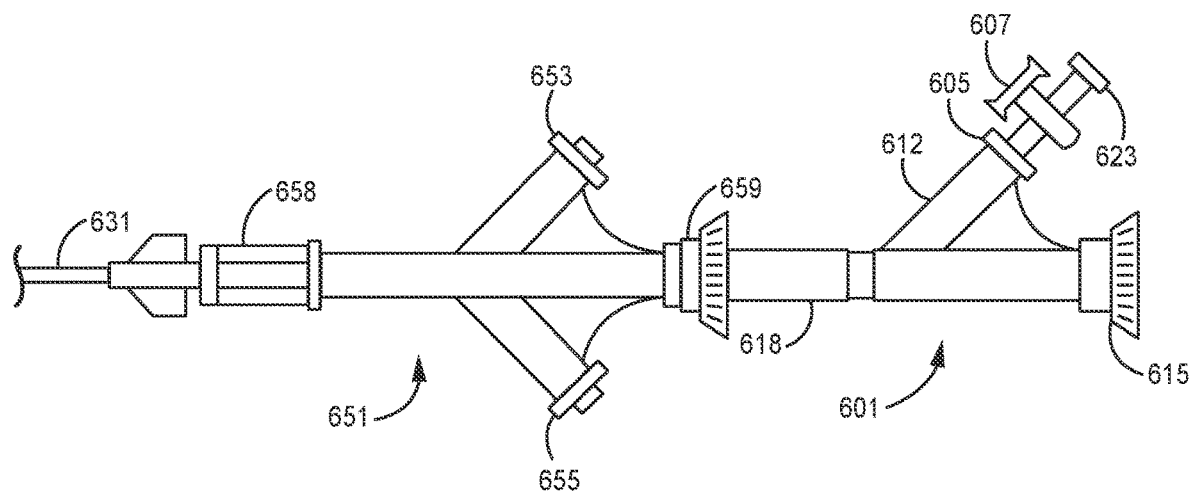
FIG. 33 is a side view of a guide catheter, an alternative embodiment of a first fitting element with a branched manifold with an additional branch, and a docking branched manifold.

As illustrated in the fragmentary view of FIG. 32, a suction catheter system generally comprises a guide catheter 631 and a Y-branch manifold 633 is shown as the first fitting element, and any of the guide catheter embodiments and first fitting elements above can generally be used for this configuration. As depicted in FIG. 32, the docking branched manifold is the structure shown in FIG. 31A, and the alternative structures described in the context of this Fig. apply equally to the embodiment of FIG. 32. First fitting element 633 comprises a connector 635, tubular body 637, branch conduit 639 with a connector 641, and hemostatic valve 643. Similarly, other embodiments of the first fitting elements and docking branched fittings can be adapted into the assembled system. Docking branch manifold 601 can be designed to interface with Y-branch manifold 633 with proximal section 618 inserted through hemostatic valve 643. It should be understood that various manifold configurations are within the scope of this application. For example, the disclosed suction catheter system is not limited to the two pathways available in Y-branch manifold 633. For example, an unbranched first fitting element, as shown in FIG. 24B can be used. For another example, FIG. 33 depicts a suction catheter system including tri-branch manifold 651. Manifolds with additional branches may be used as well. Alternatively, manifolds may be connected to one another creating additional pathways. For example, an additional manifold could be attached at connector 653 or a second connector 655. Tri-branch manifold 651 connects with guide catheter 631 at connector 658. At a proximal end of tri-branch manifold 651, input tubular section 603 is inserted through hemostatic valve 659 to provide for docking with the suction extension within Y-branch manifold 633. Similarly, first fitting elements can comprise an integral structure or a structural component serving as an extended hemostatic fitting, such as shown about in FIGS. 24-26, that provides for removal of the tubular extension of the suction extension out from the guide catheter within a hemostatic environment, and the structures in FIGS. 30-34 can be correspondingly interpreted to include this capability based on an adjustment of structure of dimensions.

FIG. 34A shows the assembled system of FIG. 32 with a suction extension deployed through the components, and control wire 661 is shown extending from hemostatic valve 615. FIG. 34B shows a sectional view of a portion of the suction catheter system depicted in FIG. 34A. Control wire 661 passes through docking branch manifold 601 and is secured to suction extension 663. As noted above, in embodiments in which the docking branched manifold is configured with a connection to a negative pressure device, a first fitting element with a branched manifold can be replaced with a first fitting element that is not branched, if desired, although the system can optionally provide aspiration from a selected connector from a plurality of available connectors or the connection of a manifold of the first fitting element can be used to deliver contrast dye or a therapeutic compound as an alternative to connection to a negative pressure device.

FIG. 34B illustrates suction extension 663 docked in docking structure 617. However, control wire 661 can be manipulated, for example by pushing on it thereby exerting an axial force in the distal direction, to release suction extension 663 from docking structure 617 and reintroduce suction extension 663 into the patient. Conversely, when suction extension 663 is not docked, control wire 661 can be manipulated to draw a proximal end of suction extension 663 into docking structure 617 until the tubular extension of suction extension 663 is secured. For example, control wire 661 could be pulled in the proximal direction until suction extension 663 forms an interference fit with a tapered portion of input tubular section 603. Alternatively, as shown in FIG. 34C, control wire 661 could be extended such that control wire extends entirely through docking structure 617 and thereby the tubular extension of suction extension 663 is distal to docking branched manifold 601.

Once suction extension 663 is docked in docking structure 617, docking branch manifold 601 can be separated from Y-branch manifold 633 such that suction extension 663 is withdrawn proximally through hemostatic valve 635. With the structures separate, source valve 607 may be opened to allow fluid to flow into docking branch manifold 601, through docking structure 617, and subsequently through suction extension 663. The flow of fluid can dislodge a thrombus or other matter trapped within the tubular extension of suction extension 663. Examples of fluids include, for example, sterile water, saline solutions, contrast dye, or other sterile fluids. If the procedure is ongoing, once suction extension 663 is clear of blockage, it may be reinserted through hemostatic valve 635 and into Y-branch manifold 633. Once docking branch manifold 601 is reinserted and secured within Y-branch manifold 633, control wire 661 may be used to disengage suction extension 663 from docking structure 617 and reintroduce the tubular extension of suction extension 663 into the patient for the collection of additional clotting material from the occluded blood vessel.

The particular embodiment of the docking branched manifold in FIGS. 31 to 34 are a representative embodiment, but other embodiments can have more than two branches with appropriate additional connectors, additional flow control elements, different angles for the branches, and the like. In particular, features described in the context of FIG. 30 can be adapted for the second representative structure in FIGS. 31-34. For example, the first branch of the docking branched manifold can comprise a source valve that controls the flow that can originate from a fluid source or flow to an aspiration source, such as a pump, to aspirate fluid from the manifold. Rather than using further branches off of a first branch, additional branches can be provided on the manifold to provide for access to additional fluid sources and/or an aspiration source, which would be similar to the additional branches for the first branched manifold of the proximal fittings shown in FIG. 25. A person of ordinary skill in the art can adjust the design based on the functional constraints based on the teachings herein.

The docking branched manifolds generally have suitable dimensions for convenient handling and manipulation and the interior dimensions are suitable for the handling of the various devices described herein. The components of the docking branched manifold can be formed in either rigid and/or flexible materials such as polymers provided herein, and the connectors can be formed from suitable combination of materials as long as they are suitable for the intended function of the component. Rigid components can be formed, for example, from polycarbonate, polyimides, metal or other suitable polymers. The portion of the docking branched manifold that gets secured in the hemostatic valve of the proximal fittings should have sufficient mechanical strength to avoid getting crushed by the hemostatic valve, which can be accomplished through the appropriate selection of material and wall thickness. In embodiments, tubular portions can be formed from a more flexible polymer, such as one or more of the polymers described above for the catheter body, for example, polyether-amide block co-polymer (PEBAX®), nylon (polyamides), polyolefins, polytetrafluoroethylene, polyesters, polyurethanes, polycarbonates, polysiloxanes (silicones), polycarbonate urethanes (e.g., ChronoFlex AR®), mixtures thereof, combinations thereof, or other suitable biocompatible polymers. As noted above, the various fitting structures can be assembled from additional components, added onto or subdividing the various components of the embodiments, and/or the components can be formed as integral structures correspondingly molded. Thus, particular designs can be assembled from existing commercially available components or all or a portion of the fittings can be produced specifically for these applications. In embodiments, portions of the components may be translucent or transparent. It may be beneficial for a user to be able to visually inspect the internals of the components. In some procedures it may be desirable for the user to visually determine when the suction extension is within a manifold or engaged with a docking structure. Thus, transparency in particular is a consideration for the fittings at the location where the docking structure would be located so that visual examination can help to confirm docking along with physical tactile evaluation. In some procedures, it may be desirable for the user to visually inspect tubular extension for a trapped thrombus or other debris prior to removing the tubular extension from the hemostatic environment.

The use of the aspiration systems described herein involves the manipulation of a control structure, such as a control wire, to move the body of a suction extension within a guide catheter. The movement generally involves extending the tubular extension from the distal end of the guide catheter as well as removing the suction extension from the proximal end of the guide catheter. In some embodiments, the guide catheter does not include a stop or other interfacing structure to engage the connection section of the suction extension to prevent the movement of the connection section of the suction extension from the distal opening of the guide catheter. If the connection section of the suction extension passes through the distal opening of the guide catheter, it may be difficult to recover the procedural objectives without removal of the guide catheter from the patient, which can result in undesirable delays that provide risk to the patient and add to costs associated with procedure times. While markings can be provided on a control structure to instruct the health care professional not to ever insert the control structure, such a system may involve an undesirable level of risk with respect to user error.

A handle can be secured to the control structure at or near the proximal end of the control structure to facilitate gripping the control structure as well as to prevent over insertion of the control structure into the guide catheter. The grip or handle then can have a shape or sufficient thickness orthogonal to the control structure to inhibit insertion of the handle through a hemostatic valve. Various configurations can be suitable for a grip or handle, although generally they should be easily gripped by a heath care professional with one hand for manipulation during a procedure. A handle can be fixedly attached to the control structure, or the grip can be repositionable on the control structure. If the grip is repositionable, the proximal end of the control structure can be bent, tied, twisted, or otherwise altered to make it difficult or impossible to remove the grip without destroying a component. For use, the handle should be appropriately anchored if it is not permanently secured at a particular position. If the handle can be repositioned, for example to allow for use with different fittings or guide catheter embodiments, the securing of the handle can be provided with a screw, a clip, snap, other fastener, or other appropriate structure, which can be engage during manufacture of a product or by the user with appropriate instruction.

Figure 35A:
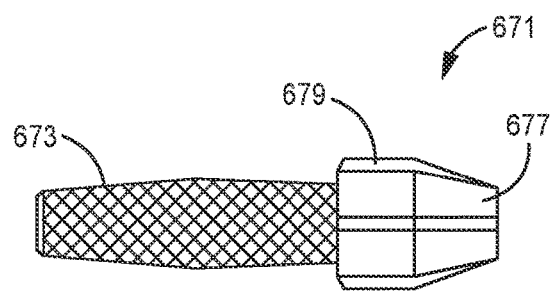
FIG. 35A is a side view of an assembled pin vise handle.
Figure 35B:
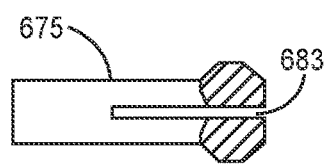
FIG. 35B is a cross-sectional view of a collet separated from the pin vise of FIG. 35A.
Figure 35C:
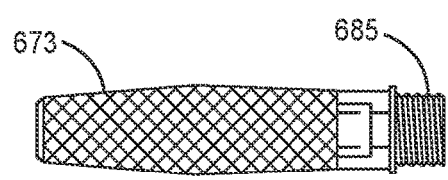
FIG. 35C is a side view of a pin vise with a head removed.
Figure 35D:
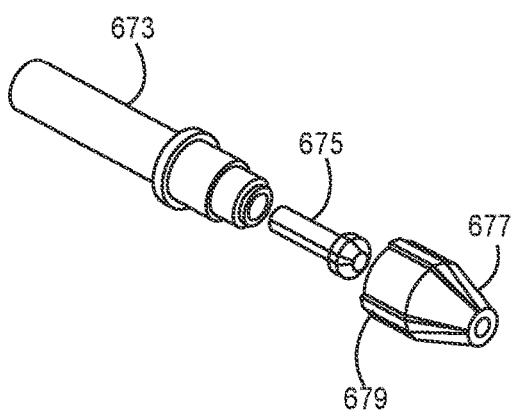
FIG. 35D is an exploded view of the pin vise handle of FIG. 35A with the components separated along the central axis.

In one representative embodiment, a handle is provided by a pin vise. FIGS. 35A-35C illustrate an embodiment of a pin vise 671 with a knurled collet holder 673, a collet 675, and a head 677. In embodiments, head 677 may have one or more ribs 679. Ribs 679 may make it easier to turn head 677 in order to either retain or release control wire 681. Further, ribs 679 may help prevent pin vise 671 from rolling, such as when placed on a surgical tray or table. Collet 675 has a thru hole 683 configured to receive control wire. When control wire is inserted into thru hole 683, rotating head 677 about threads 685 in a first direction causes collet 675 to clamp down on control wire in a vise like grip, and rotating head 677 in an opposite direction causes collet 675 to release control wire. When control wire is secured by collet 675, collet holder 673 may be manipulated to exert control over a control wire and a corresponding suction extension. For example, twisting collet holder 673 may place torque on a control wire. Pulling collet holder 673 axially may withdraw a suction extension from a patient and/or cause suction extension to dock within a docking structure. Similarly, pushing collet holder 673 axially may release a suction extension from a docking structure and/or reposition a suction extension within the vasculature of a patient.

The suction catheter system is generally appropriately sterilized, such as with e-beam or gas sterilization. The suction catheter system components can be packaged together or separately in a sealed package, such as plastic packages known in the art. The package will be appropriately labeled, generally according to FDA or other regulatory agency regulations. The suction catheter system can be packaged with other components, such as a guidewire, filter device, and/or other medical device(s). The packaged system generally is sold with detailed instructions for use according to regulatory requirements.

Procedures Making Use of Treatment Systems

As indicated above, the medical systems comprising a suction catheter system described herein can be used with the suction catheter system as stand-alone treatment device, perhaps with a guidewire and/or other delivery support devices, or used with supplemental medical treatment devices for treatment of ischemic vessel blockage. In particular, in some embodiments, the suction system is used with an embolic protection device, and in additional embodiments, some form of clot engagement device, stent, balloon, atherectomy device or the like may also be used. In any case, a guidewire is generally used to provide access to the treatment site. The guide catheter portion of the suction catheter system may or may not be positioned prior to the introduction of the suction extension. The structures of the particular components are described in detail above, and are not repeated so that this section can focus on the use of the devices. The use of the alternative embodiments of the various fitting components can be adapted by a person of ordinary skill in the art based on the teachings herein.

Figure 36:
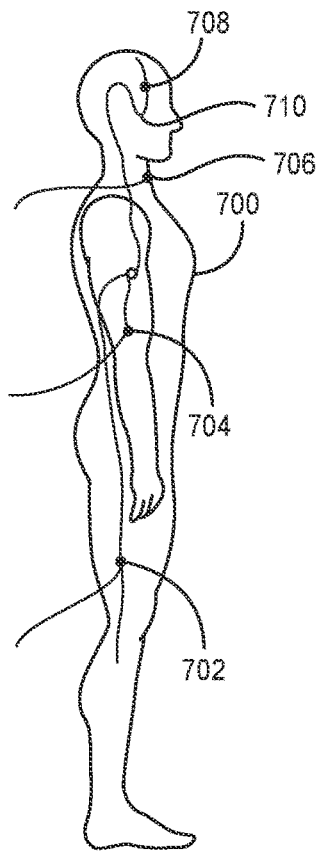
FIG. 36 is a schematic depiction of a human patient with alternative access approaches for directing catheters into the blood vessels of the brain.
Figure 37:
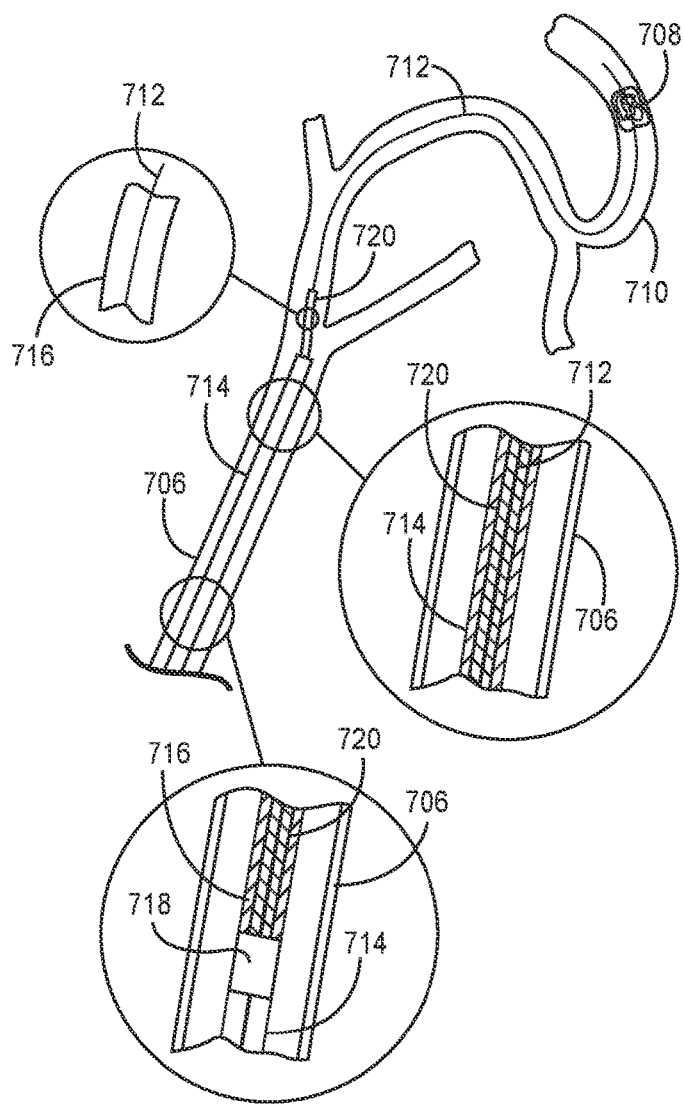
FIG. 37 is a view within a branched blood vessel section showing the delivery of medical devices along a guidewire from a guide catheter to a clot. Inserts show expanded views of two internal sections of the guide catheter.
Figure 38:
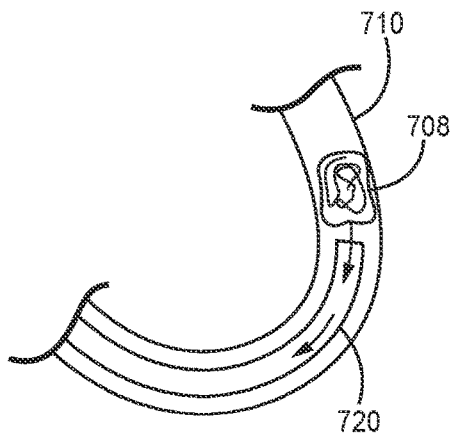
FIG. 38 is a schematic view in a section of blood vessel of a suction system being used to remove a clot.

For the treatment of an acute ischemic stroke condition, referring to FIG. 36, a patient 700 is shown with three alternative access points into the vasculature, femoral artery 702, artery in the arm 704 or carotid artery in the neck 706. Regardless of the access point, the catheter and associated devices are guided to the left or right carotid artery to reach a clot 508 in a cerebral artery 710 of the brain. Referring to the schematic view in FIG. 37, clot 708 is shown in cerebral artery 710 with a guidewire 712 positioned with its distal tip past the clot. Guide catheter 714 is positioned over the guidewire within the carotid artery 706. Suction extension 716 with connecting section 718 within guide catheter 714 and tubular extension 720 extending from guide catheter 714 over guidewire 712. Referring to FIG. 38, tubular extension 720 can be advanced over the guidewire to a position near clot 708. Suction can be applied as shown with the flow arrows in the figure. Guidewire 712 may or may not be removed before suction is applied. Suction catheters have successfully removed clots responsible for ischemic stroke without further medical devices in the intervention. However, for more difficult clots, additional medical treatment devices can be used as described in detail below.

Using the embodiments of proximal fittings, such as shown above, adapted with pressure sensing capability, the initiation of suction as described in the context of FIG. 38 can be checked with respect to its efficacy. If appropriate flow is established since negative pressure is applied to the catheter system, the pressure in the proximal fittings can be in a suitable range. The precise ranges of expected pressures generally are dependent on the specific design of the suction extension, and the acceptable pressure range can be adjusted accordingly. In any case, the pressure can be confirmed in real time during the procedure for comparison with specifications adapted for the specific suction catheter components. If the pressure at the time immediately following the initiation of suction is closer to the negative pressure of the pump than expected based on the set acceptable range, the physician can withdraw the suction extension at least part way from the delivered configuration with or without stopping suction. A partial withdrawal can be used to try to unkink the suction extension without complete removal. As described further below, if proximal fittings are used that allow removal of the tubular extension for the patient without passing through a hemostatic valve, the tubular extension can be visually checked without exposing the tubular extension to the ambient atmosphere. After verifying that the tubular extension is ready for use or after replacing the suction extension, the suction extension can be redelivered.

When using the suction system to clear actual clots associated with acute ischemic stroke events, it is frequently found that the tubular extension becomes clogged itself prior to fully clearing the vessel. Therefore, it can be desirable to clear the clot form the tubular extension and reintroduce the suction extension back into the cerebral vessel to remove additional thrombus. The clearing and reintroduction can be repeated as necessary. The fittings described herein can facilitate this process, and the use of these fittings to effectuate this process are described further below. The desire to clear clots form the suction extension and reintroducing the suction extension may also be performed with the use of additional treatment structures as described in the following.

Figure 39:
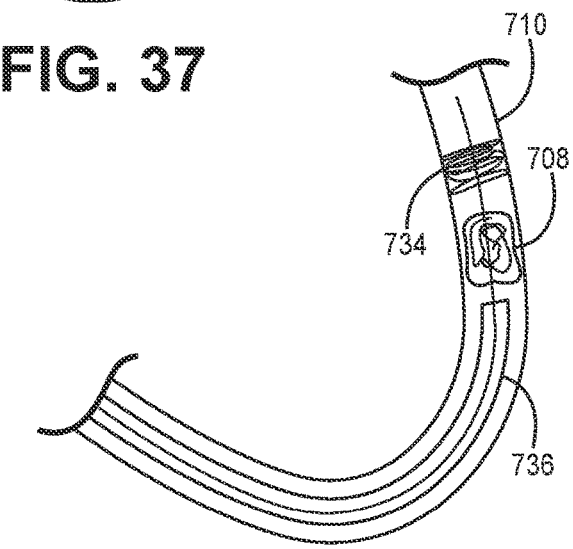
FIG. 39 is a schematic view in a section of blood vessel with a suction system positioned upstream from a clot and a fiber based filter deployed downstream from the clot.
Figure 40:
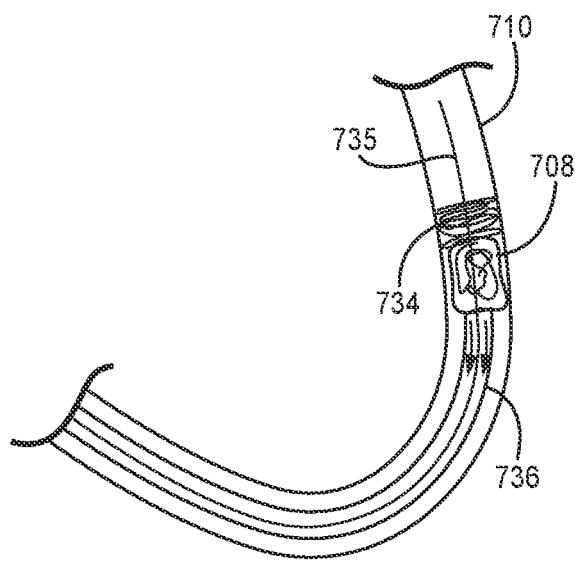
FIG. 40 is a schematic view of the section of blood vessel of FIG. 39 with the fiber based filter being drawn toward the suction tip to draw the clot to the tip for facilitating removal of the clot.

Referring to FIGS. 39 and 40, the use of a fiber-based filter device is shown in use along with the suction catheter system. As shown in FIG. 39, clot 708 is shown in cerebral artery 710 with a deployed fiber-based filter 734 supported on a guidewire 736 positioned with the filter deployed past the clot. Fiber-based filter 734 can have fiber elements extending essentially to the wall of the vessel, cerebral artery 710. Tubular extension 736 can be positioned with its distal tip just proximal to the clot, and the remaining portions of the suction catheter system are not shown in this view. Referring to FIG. 40, fiber-based filter 734 can be pulled toward tubular extension 736 with suction being applied to facilitate removal of clot 730. Clot 708 can be broken up and removed by suction, and/or all or a portion of clot 708 can be pulled into tubular extension 736 optionally along with all or part of the fiber-based filter, and/or all or a portion of clot 708 can be held to the opening of tubular extension 736 with the fiber-based filter holding the clot. In any case, once the clot is appropriately stabilized, the devices and any clot still within the vessel or catheter can be removed from the patient. The removal of the devices is described further below.

Figure 41:
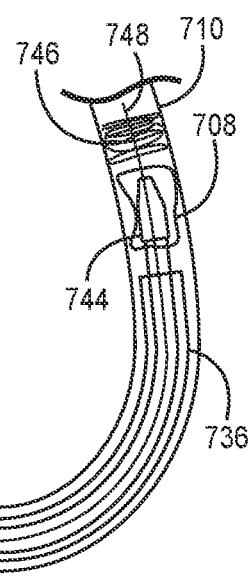
FIG. 41 is a schematic view of a section of blood vessel with a suction system positioned upstream from a clot, a fiber based filter deployed downstream from the clot and another medical device positioned at the clot.
Figure 42:
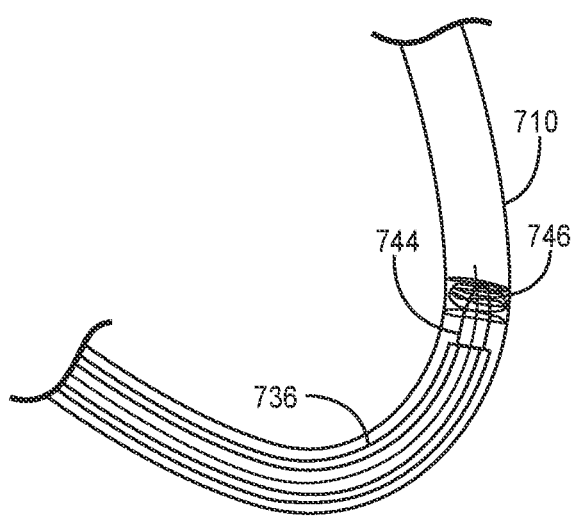
FIG. 42 is a schematic view of the section of blood vessel of FIG. 41 with the various medical devices being used in concert for the removal of the clot.

The further use of an additional medical device to facilitate clot removal is shown in FIGS. 41 and 42. As shown in FIG. 41, clot 708 is shown in cerebral artery 710 with a medical treatment device 754 positioned at the clot and deployed fiber-based filter 756 supported on a guidewire 758 positioned with the filter deployed past the clot. Suitable medical treatment devices for clot engagement are described above. The selected medical treatment device is deployed generally with protection from the deployed fiber-based filter and optionally with suction. Once the clot is engaged with the medical treatment device, the recovery of the remaining portions of the clot and the medical treatment devices can be removed as shown in FIG. 42, similarly to the process shown in FIG. 41. In particular, the medical treatment device can be removed, although portions such as a stent may be left behind, and the removal can precede or be done in conjunction with removal of a filter and/or remaining fragments of clot. All or a portion of clot 708, if not already broken up and removed with suction can be pulled into tubular extension 736 optionally along with all or part of the fiber-based filter, and/or all or a portion of clot 708 can be held to the distal opening of tubular extension 736 with the fiber-based filter holding the clot. Again, once the clot is appropriately stabilized, the devices and any clot still within the vessel or catheter can be removed from the patient. The use of a plurality of additional medical treatment devices can be performed through extension of the procedure outlined above to repeat steps involving the additional medical device.

Also, for the embodiments in FIGS. 37-42, a pressure sensor connected to the proximal fittings can be used to guide the procedures. If the pressure in the proximal fittings increases to a pressure outside of a target range when negative pressure is initiated, appropriate remedial attention can be applied to remove a kink, or replace/clear the suction extension, or other appropriate attention. Also, after suction is applied and the clot seems to have been addressed, the pressure in the proximal fittings can be checked to evaluate the status of the clot and the catheter, such as whether or not the clot is trapped at the distal end of the suction extension. Appropriate care can be taken based on the pressure in the proximal fittings.

Figure 43:
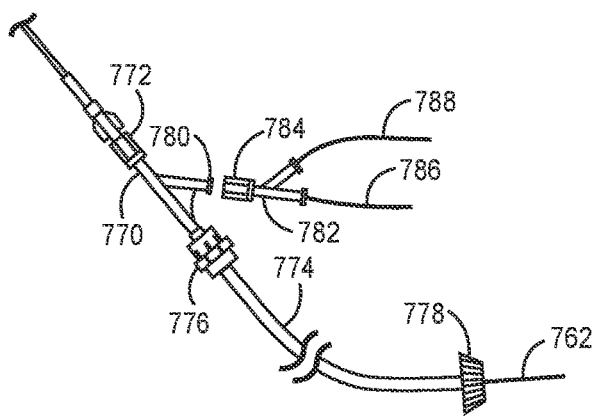
FIG. 43 is a fragmentary view of a treatment system extending from a position in the neuro-vasculature to the proximal fittings shown following application of suction and optionally other procedural steps to remove a clot, with an insert in the figure showing a sectional view of a tubular extension within a guide catheter.

FIG. 43 depicts the suction treatment system following treatment of a clot in cerebral artery 750. Tubular extension 752 is positioned with its distal tip in cerebral artery 750 and thrombus 754 may or may not be present at the opening. Guide catheter 756 is located with its distal end in carotid artery 758. A section of the interior of guide catheter 756 is shown in a balloon insert of FIG. 43. Connecting section 760 of suction extension 752 is within guide catheter 756 with control wire 762 extending in a proximal direction. The patient's leg 764 is shown with an introducer sheath 766 extending from the leg with a hemostatic valve 768. Guide catheter 756 extends out from hemostatic valve 768. Y-branch manifold 770 is connected to the distal end of guide catheter 756 at connector 772. Extended hemostatic fitting 774 is connected with Y-branch manifold 770 at connector 776, and terminates with a hemostatic valve 778. Control wire 762 extends from hemostatic valve 778. Y-branch manifold 770 has a connector 780 that can be connected to a further Y-branch manifold 782 with connector 784 for connection to connector 780. Y-branch manifold can be connected to a negative pressure line 786 that can be connected to a pump or other negative pressure device, and to a pressure sensor line 788 that can be connected to an appropriate pressure sensor such as those of FIGS. 27-29. The fittings of FIG. 43 can be combined with a docking branched manifold at hemostatic valve 778, and suitable embodiments of a docking branched manifold are described above. The combination of Y-branched manifold 770 and extended hemostatic fitting 774 can be considered components of the first fitting elements.

Figure 44:
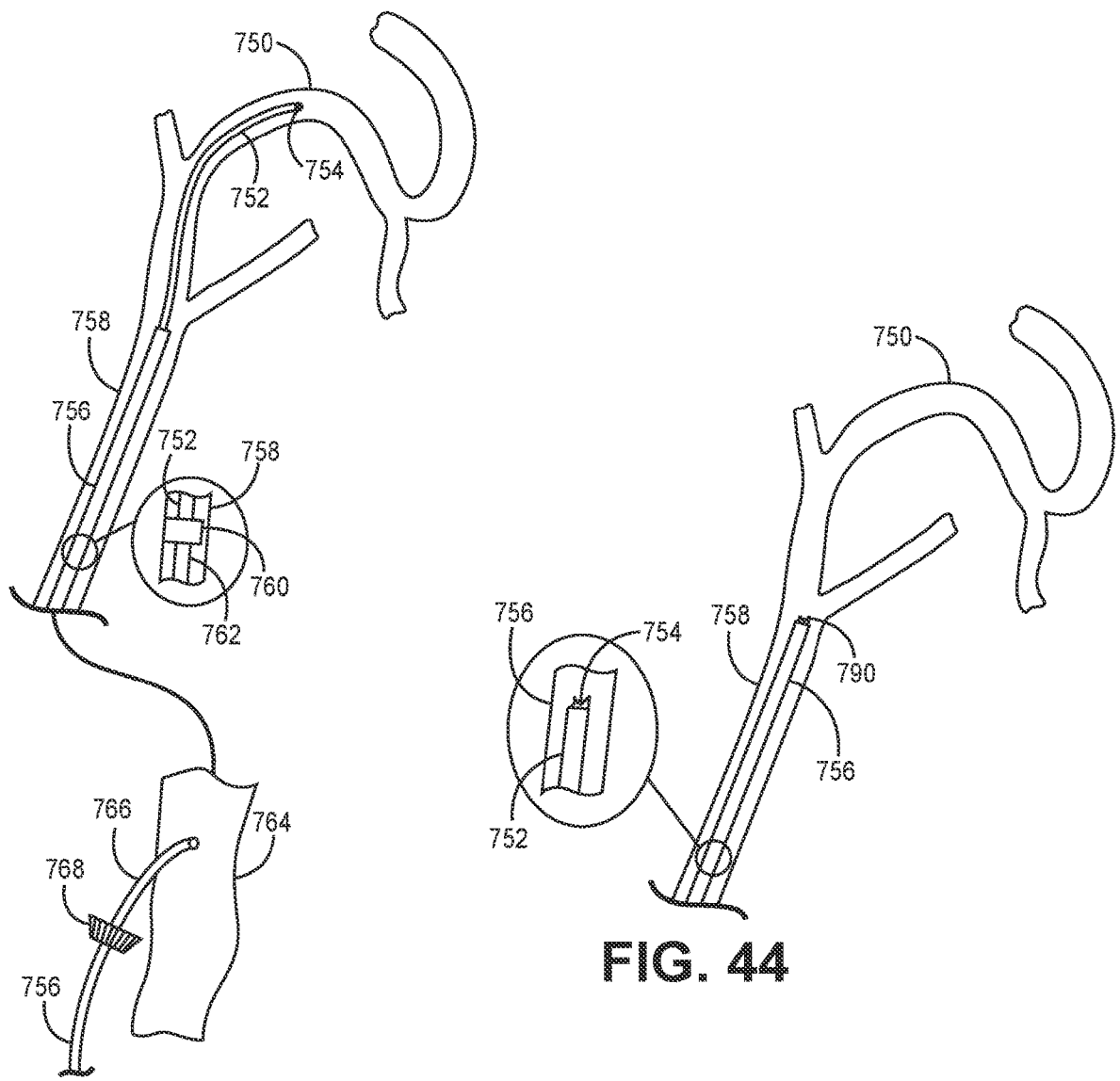
FIG. 44 is a fragmentary view of the distal portion of the treatment system of FIG. 43 in which the tubular extension is withdrawn into the guide catheter, with an insert of the figure showing sectional view of the distal end of the tubular extension within the guide catheter.
Figure 45:
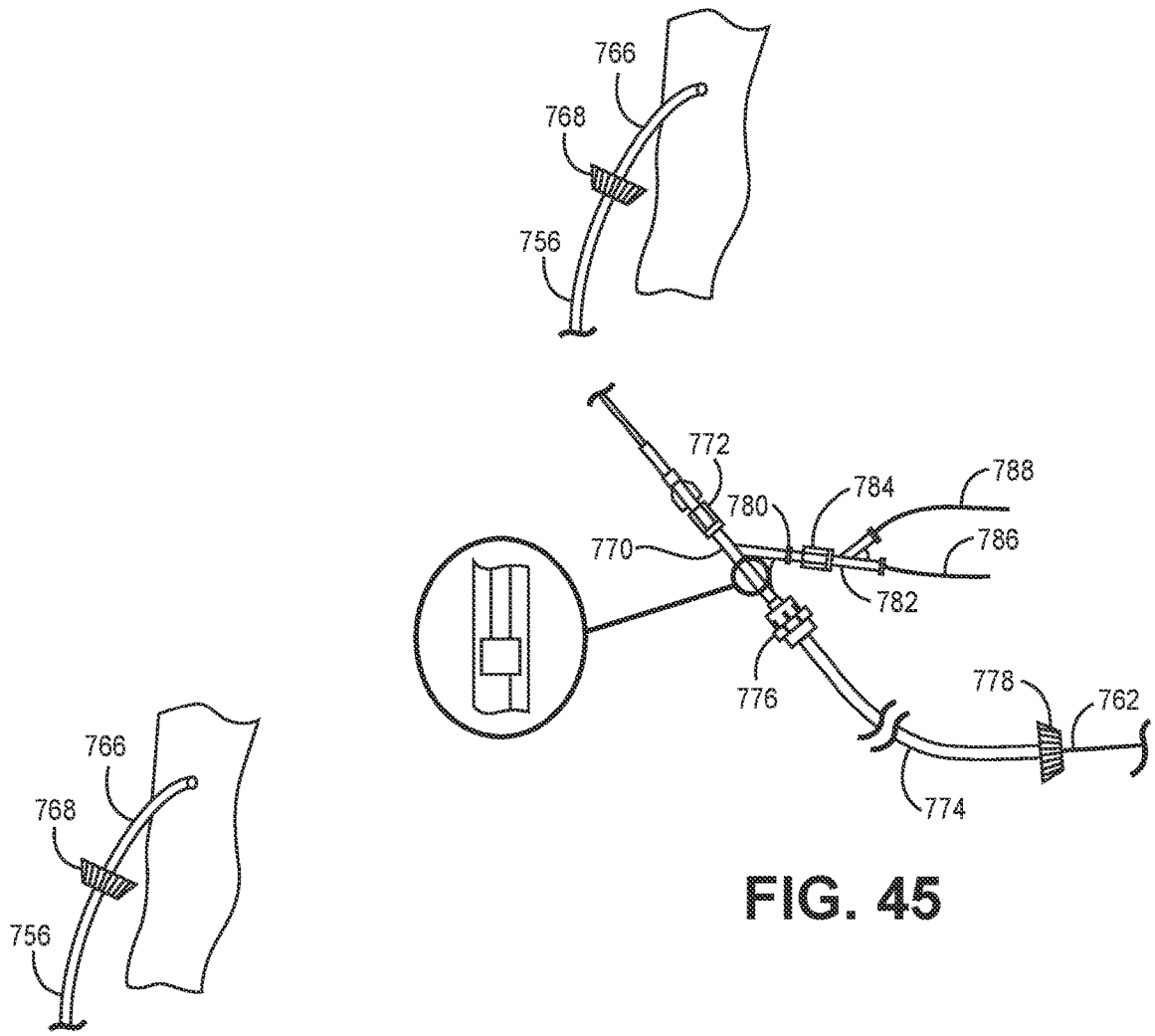
FIG. 45 is a fragmentary view of the proximal end of the treatment system of FIG. 43 in which the tubular extension is withdrawn sufficiently such that a connection section of the suction extension is within proximal fittings external to the guide catheter as shown in the sectional view of the figure insert.
Figure 46:
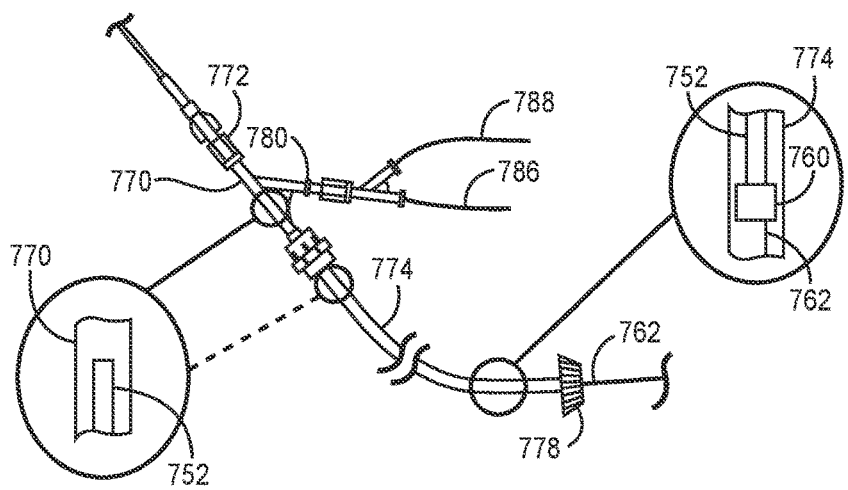
FIG. 46 is a fragmentary view of the proximal end of the treatment system of FIG. 43 in which the tubular extension is withdrawn from the guide catheter but remains enclosed in the proximal fittings with sealed hemostatic valves, with a left figure insert showing a sectional view of the distal end of tubular extension within a Y-branch manifold (and an alternative placement of the distal extension within extended hemostatic fitting noted with a dashed line) and a right figure insert showing the connection section of the suction extension within an extended hemostatic fitting with a control wire extending through a hemostatic valve.
Figure 47:
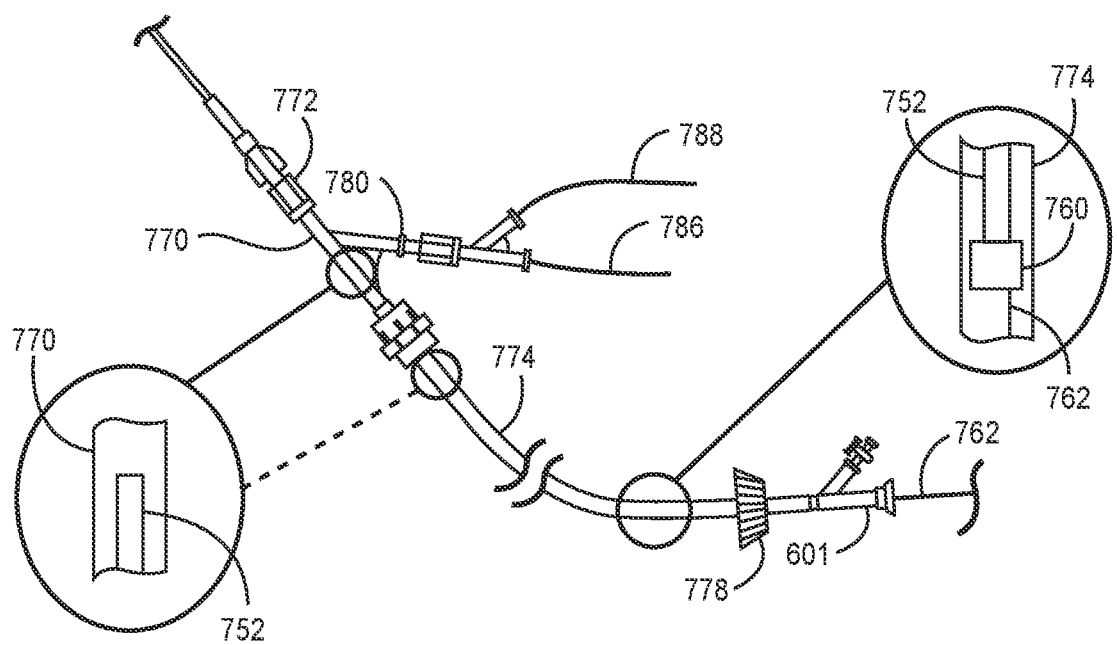
FIG. 47 is a fragmentary view of the proximal end of the treatment system of FIG. 43 in which the tubular extension is withdrawn from the guide catheter but remains enclosed in the proximal fittings with sealed hemostatic valves, with a left figure insert showing a sectional view of the distal end of tubular extension within a Y-branch manifold (and an alternative placement of the distal extension within extended hemostatic fitting noted with a dashed line) and a right figure insert showing the connection section of the suction extension within an extended hemostatic fitting with a branched manifold connecting to the hemostatic valve and a control wire extending through a hemostatic valve of the branched manifold.
Figure 48:
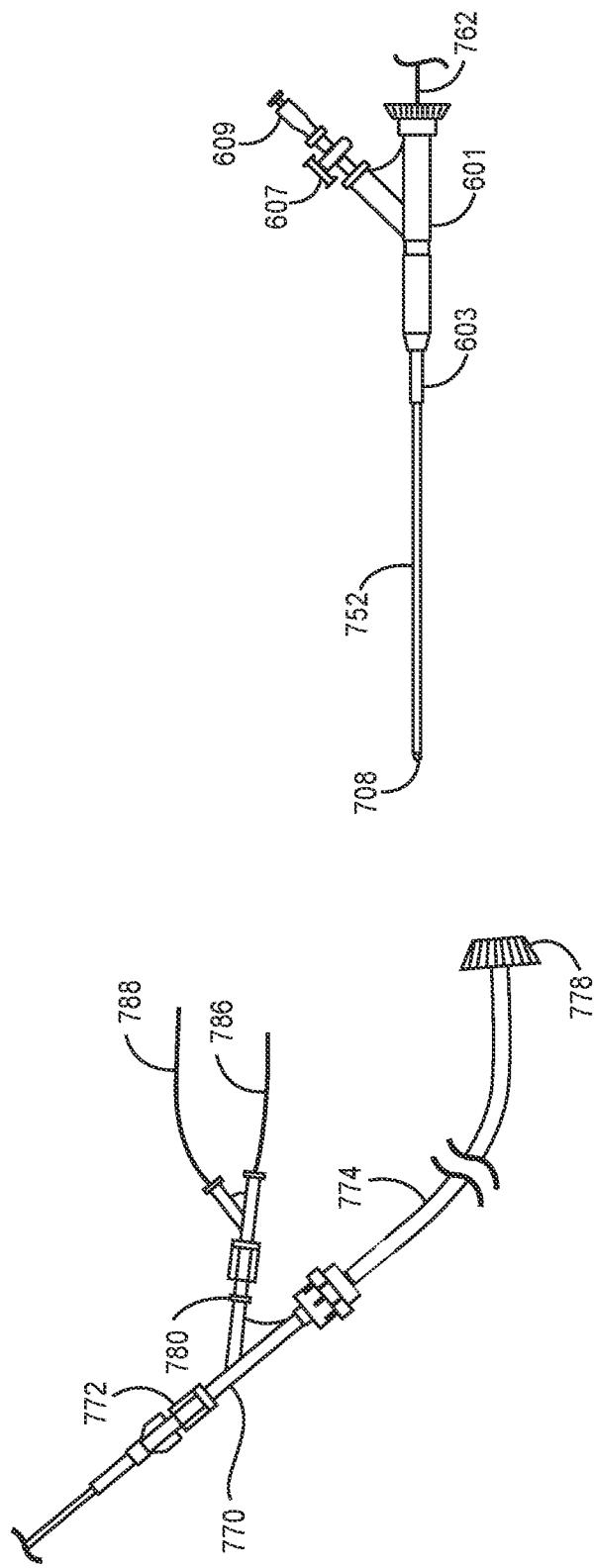
FIG. 48 is a fragmentary view of the proximal end of the treatment system of FIG. 43 in which the tubular extension having at least a portion of a clot at the distal end is docked in a branched manifold and is fully withdrawn from the sealed hemostatic valve of the treatment system.

At the stage of the procedure shown in FIGS. 38 (assuming thrombus is removed to the extent desired) and 43, procedural steps can be initiated for gradual removal of the devices from the patient. FIGS. 44-46 show the removal process using extended fittings that provide for the removal of the suction extension completely form the guide catheter behind a hemostatic valve. FIGS. 47 and 48 depict the use of the docking Y-fitting providing for the efficient clearing and reintroduction of the suction extension. It can be advantageous to maintain the guide catheter in position while removing the other components and verifying the success of the procedure. Generally, it is desired to keep the guide catheter in place until the procedure is to be completely ended since the guide catheter placement involves significant effort. As noted above, the suction extension may be removed, cleared of clots, and reintroduced for additional thrombus removal prior to termination of the overall procedure. This removal and reintroduction of the suction extension can be performed with the guide catheter fixed in place.

Pressure readings at the proximal fittings can provide useful information regarding the status of potential blockages of flow into suction extension 752, although other more qualitative evaluations can be performed such as the termination of fluid flow into the pump.

Referring to FIG. 44, guide catheter 756 is still in place in carotid artery 758 and cerebral artery 750 is clear of devices and clot. Referring to the balloon figure insert associated with FIG. 44, a further enlarged sectional view shows the distal end of suction extension 752 within the interior of guide catheter 756. Thrombus may or may not be associated with the distal end of guide catheter 756 (thrombus 790), which can be deposited there when suction extension 752 is withdrawn into guide catheter 756, and/or at the distal end of suction extension 752 (thrombus 754). Again, a pressure reading in the proximal fittings can provide useful information on potential thrombus blocking flow through the catheter system to the negative pressure device, such as a pump.

Referring to FIG. 45, upon further withdrawal of suction extension 752 from the patient, a balloon figure insert shows a further enlarged section view with connecting section 760 of suction extension 752 within T-branch manifold 770. With this configuration, a continuation of application of negative pressure would draw fluid from guide catheter 756 rather than through suction extension 752. Whether or not suction extension 752 is plugged, this configuration can provide addition possibility of removal of thrombus 790 at the end of guide catheter 756, and the suction can further stabilize thrombus 790, if any, for further portions of the procedure. At this stage of the procedure, the pressure in the proximal fittings can provide information on the flow of liquid into guide catheter 756.

The complete removal of suction extension 752 from guide catheter 756 is shown in FIG. 46. A distal balloon figure insert in FIG. 46 shows a further expanded section view with the distal end of suction extension 752 within T-branch manifold 770, although the distal end of suction extension 752 can be withdrawn fully into extended hemostatic fitting 774 as noted by the dashed line connected to the balloon figure insert. A proximal balloon figure insert in FIG. 46 shown a further expanded sectional view with connection section 760 within extended hemostatic fitting 774 in a position distal to hemostatic valve 778. Again, pressure within proximal fittings can be useful to provide information during this part of the procedure.

While guide catheter 756 can be removed from the patient following treatment of the clot, it can be desirable to at least partially remove suction extension 752 relative to its deployed location with the guide catheter in position to reduce the risk of embolization of thrombus that may be trapped in association with the aspiration system components but not yet fully removed from the patient. FIGS. 44-46 depict three stages of suction extension removal at which time it can be selected to remove guide catheter 756 from the patient, generally through hemostatic valve 768 of introducer 766. With the distal end of suction extension 752 within guide catheter 756, as shown in FIG. 44, any thrombus associated with suction extension 752 is within guide catheter 756 so that it is less likely to involve embolization. Referring to FIG. 45, as noted above, connection section 760 within Y-branch manifold 770, suction is applied directly to guide catheter 756 lumen regardless of whether or not suction extension 752 is clogged, and this direct application of suction to guide catheter 756 provides an added degree of safety with respect to reducing chances of embolization. Furthermore, complete removal of suction extension 752 from guide catheter 756, as shown in FIG. 46, provides additional safety against embolization of thrombus associated with suction extension 752. As shown in FIG. 46, suction extension 752 remains in isolation behind a hemostatic valve 778, and this configuration provides for desirable control of pressures within guide catheter 756 that further reduces risk of embolization as well as contamination.

FIG. 47 shows a docking branched manifold 601 with a distal end inserted through hemostatic valve 778 and control wire 762 extending proximally. As discussed above, the use of docking branch manifold 601 permits efficient clearing and reintroduction of the suction extension. As shown in FIG. 47, suction extension 752 is removed from guide catheter 756 but still remains in isolation behind hemostatic valve 778. When suction extension 752 is clogged, the configuration shown provides added safety against embolization of thrombus. However, to safely reintroduce suction extension 752 into a patient, clogs should first be cleared from suction extension 752. As discussed above, control wire 762 may be used to dock suction extension 752 in docking branch manifold 601.

FIG. 48 shows both docking branch manifold 601 and suction extension 752 fully withdrawn from isolation behind hemostatic valve 778. In this configuration, a proximal end of suction extension 752 is docked within input tubular segment 603. Further, at least a portion of clot 708 is shown clogging a distal end of suction extension 752. Reintroduction of suction extension 752 into a patient while clot 708 is clogging a portion of suction extension 752 could be unsafe. Accordingly, with suction extension 752 fully removed from hemostatic valve 778, valve 607 may be opened so that a positive pressure device such as syringe 609 may inject fluid to flush clot 708 from suction extension 752. Once suction extension 752 is cleared, suction extension 752 may be reinserted through hemostatic valve 778. Sterile procedures can be used to maintain suction extension 752 in a sterile condition for reintroduction into the patient. In some procedures, cleared suction extension 752 may be fully reintroduced into a patient for retrieval of additional emboli. As noted above, the docking manifold can be configured to deliver aspiration, contrast fluid or other fluids to facilitate performance of the procedure. For these additional or alternative embodiments, the procedures can be straightforwardly revised.

Bench testing and calculations were performed to evaluate the general suction performance of the use of a suction extension interfaced with a guide catheter and for other commercial suction catheters. These results are described in the '938 application, and are incorporated herein by reference.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein. To the extent that specific structures, compositions and/or processes are described herein with components, elements, ingredients or other partitions, it is to be understood that the disclosure herein covers the specific embodiments, embodiments comprising the specific components, elements, ingredients, other partitions or combinations thereof as well as embodiments consisting essentially of such specific components, ingredients or other partitions or combinations thereof that can include additional features that do not change the fundamental nature of the subject matter, as suggested in the discussion, unless otherwise specifically indicated.

What is claimed is:

1. A suction catheter system comprising:
   a guide catheter comprising a tubular shaft with a central lumen having a proximal end and a distal opening;
   a suction extension catheter comprising a connecting section with a central lumen, a tubular extension comprising a tube that is connected with the connecting section and extends from the connecting section in a distal direction to form a continuous lumen through the central lumen of the connecting section through the tube of the tubular extension, and a control structure comprising an elongated structure extending from the connecting section in a proximal direction, wherein the connecting section is configured to slide within at least a portion of the central lumen of the guide catheter to change the relative position of the connecting section within the central lumen and provide for at least a portion of tubular extension to extend outward from the distal opening of the tubular shaft at appropriate configurations of the connecting section; and
   proximal fittings connected to the proximal end of the guide catheter, the proximal fittings comprising a first fitting element with a tubular body having a distal connector connected to the proximal end of the guide catheter and a first hemostatic valve wherein the suction extension catheter is configured to pass through the first hemostatic valve, and a docking branched manifold comprising an input tubular segment connected with a first branch having a valve and terminating with a connector, and a second branch having a hemostatic valve, wherein the input tubular segment comprises a docking structure to engage the proximal end of the connection section of the suction extension catheter at a position distal to the first branch to form a continuous fluid channel from the central lumen into the docking branched manifold and wherein at least a portion of the input tubular segment is configured for insertion through and securing within the first hemostatic valve.

2. The suction catheter system of claim 1 wherein a port of the valve of the first branch of the docking branched manifold is connected to a fluid source and wherein the valve is configured to move between an open configuration permitting the flow of fluid from the fluid source into the docking branched manifold and a closed position configured to prevent the flow of fluid into the docking branched manifold.

3. The suction catheter system of claim 2 wherein the fluid source comprises sterile saline or contrast dye.

4. The suction catheter system of claim 1 wherein the docking branched manifold comprises a connection to an aspiration source that is configured to deliver suction to the input tubular segment.

5. The suction catheter system of claim 1 wherein the first fitting element comprises a branch that is connected to a negative pressure source.

6. The suction catheter system of claim 1 wherein the docking structure of the input tubular segment comprises a narrowing of an inner diameter of the docking structure in the proximal direction.

7. The suction catheter system of claim 6 wherein the docking structure of the input tubular segment comprises an elastomeric polymer configured to engage the proximal end of the connection section to form the continuous fluid channel.

8. The suction catheter system of claim 1 wherein the input tubular segment comprises an engagement section with an outer surface suitable for engagement with the first hemostatic valve to provide a hemostatic seal.

9. The suction catheter system of claim 1 wherein the first fitting element further comprises a first tubular segment providing a length between the first hemostatic valve and the proximal end of the tubular shaft of the guide catheter that is at least as long as the length of the tube of the suction extension catheter.

10. A method of using a suction catheter system of claim 1, the method comprising:
    manipulating the control structure until the suction extension catheter is docked at a docked position within the input tubular segment of the docking branched manifold;
    separating the docking branched manifold from the first fitting element through the first hemostatic valve;
    delivering fluid through the valve into the docking branched manifold to clear debris from the suction extension catheter in the docked position; and
    reinserting the suction extension catheter through the first hemostatic valve into the patient's vessel.

11. A method for using a suction catheter system for removal of thrombus from the vasculature of a patient, the suction catheter system comprising a guide catheter having a lumen, a suction extension catheter having a tubular portion with a distal opening and a control structure, proximal fittings connected at the proximal end of the guide catheter with a first fitting element having a first hemostatic valve configured to provide access into the lumen of the first fitting element, and a docking branched manifold comprising a distal portion that can insert partially through the first hemostatic valve with a hemostatic seal, a first branch with a second hemostatic valve, and a second branch connected to a flush fluid source, wherein with the proximal end of the suction extension catheter within the lumen of the guide catheter, a suction lumen extends from the negative pressure device to a distal opening of a tubular section of the suction catheter extension and wherein the proximal end of the tubular section of the suction extension catheter can dock in the distal portion of the docking manifold to form a fluid channel from the second branch through the suction extension catheter, the method comprising
    aspirating fluid from the vasculature of a patient into the distal opening of the suction extension catheter;
    withdrawing the tubular portion of the suction extension catheter using the control structure to dock the proximal end of the tubular portion in the distal section of the docking branched manifold;
    removing the docking branched manifold and the suction extension catheter from the proximal fitting through the first hemostatic valve; and
    flushing the suction extension catheter to remove debris from the suction extension catheter.

12. The method of claim 11 further comprising:
    after flushing the suction extension catheter, reinserting the suction extension catheter into the proximal fittings through the first hemostatic valve and the distal portion of the docking branched manifold into the first hemostatic valve; and tightening the first hemostatic valve onto the distal portion.

13. The method of claim 12 further comprising:
    using the control structure to place the suction extension catheter within the vasculature of the patient; and
    applying negative pressure to attract thrombus into the suction extension catheter.

14. The method of claim 13 wherein the docking branched manifold comprises at least one branch having a hemostatic valve through which the control structure extends.

15. The method of claim 13 wherein the flush fluid source comprises sterile saline or imaging contrast fluid.

16. The method of claim 13 wherein the steps of withdrawing, removing and flushing are repeated a second time.

17. The method of claim 16 further comprising:
after repeating the flushing of the suction extension catheter, reinserting again the suction extension catheter into the proximal fittings through the first hemostatic valve and the distal portion of the docking branched manifold into the first hemostatic valve; and tightening the first hemostatic valve onto the distal portion;
using the control structure to place the suction extension catheter within the vasculature of the patient; and
applying negative pressure to attract thrombus into the suction extension catheter.

18. The method of claim 11 wherein the proximal fittings further comprise a first tubular segment providing a length between the first hemostatic valve and the proximal end of the tubular shaft of the guide catheter that is at least as long as the length of the tube of the suction extension, and the method further comprising withdrawing the tubular portion of the suction extension catheter into the first tubular segment and checking the patient's blood vessel to verify whether or not the vessel flow has been restored.

19. The suction catheter system of claim 1 wherein the first fitting element further comprise comprises an extended hemostatic fitting.

20. The suction catheter system of claim 19 wherein the extended hemostatic fitting is connected with the tubular body at a connector.

21. The suction extension system of claim 1 wherein the control structure extends through the first hemostatic valve, and wherein a continuous lumen is formed from the proximal fittings to the distal opening of the suction extension.

22. The suction extension system of claim 1 wherein the control structure comprises a handle secured near a proximal end of the control structure.

23. The suction extension system of claim 1 wherein at least a portion of the connecting section has a non-cylindrical cross section with a major outer diameter and a minor outer diameter smaller than the major outer diameter.

* * * * *